(12) United States Patent
Kapeller-Libermann et al.

(10) Patent No.: US 6,911,335 B2
(45) Date of Patent: Jun. 28, 2005

(54) 57316 AND 33338, HUMAN UBIQUITIN CARBOXYL TERMINAL HYDROLASES AND USES THEREFOR

(75) Inventors: Rosana Kapeller-Libermann, Chestnut Hill, MA (US); Rajasekhar Bandaru, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 434 days.

(21) Appl. No.: 10/098,108

(22) Filed: Mar. 13, 2002

(65) Prior Publication Data

US 2003/0166244 A1 Sep. 4, 2003

Related U.S. Application Data

(60) Provisional application No. 60/276,395, filed on Mar. 16, 2001.

(51) Int. Cl.[7] .......................... C12N 9/64; C12N 15/57; C12Q 1/68
(52) U.S. Cl. ......................... 435/226; 435/325; 435/6; 536/23.2
(58) Field of Search ............................... 435/226, 325, 435/6; 536/23.2

(56) References Cited

FOREIGN PATENT DOCUMENTS

| | | |
|---|---|---|
| EP | 1 074 617 A2 | 2/2001 |
| WO | WO 00/55177 A2 | 9/2000 |
| WO | WO 01/23409 A2 | 4/2001 |
| WO | WO 01/83775 A2 | 11/2001 |
| WO | WO 02/00860 A2 | 1/2002 |

*Primary Examiner*—Charles L. Patterson, Jr.
(74) *Attorney, Agent, or Firm*—Millennium Pharmaceuticals, Inc.

(57) ABSTRACT

The invention provides isolated nucleic acids molecules, designated 57316 or 33338 nucleic acid molecules, which encode ubiquitin carboxyl terminal hydrolase proteins. The invention also provides antisense nucleic acid molecules, recombinant expression vectors containing 57316 or 33338 nucleic acid molecules, host cells into which the expression vectors have been introduced, and non-human transgenic animals in which a 57316 or 33338 gene has been introduced or disrupted. The invention still further provides isolated 57316 or 33338 proteins, fusion proteins, antigenic peptides and anti-57316 or 33338 antibodies. Diagnostic and therapeutic methods utilizing compositions of the invention are also provided.

13 Claims, 1 Drawing Sheet

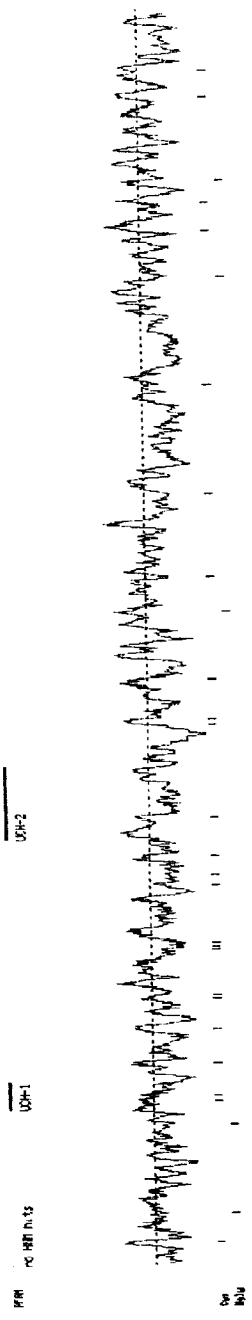
57316, A Human Ubiquitin Carboxyl Terminal Hydrolase
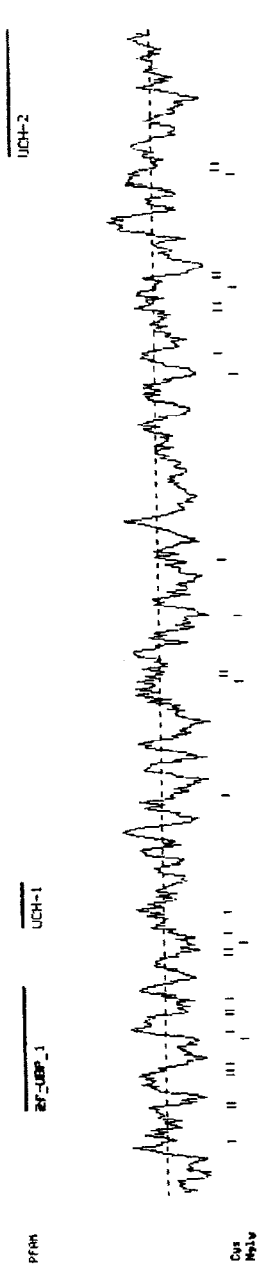
33338, A Human Ubiquitin Carboxyl Terminal Hydrolase

SEQUENCE LISTING

```
<160> NUMBER OF SEQ ID NOS: 11

<210> SEQ ID NO 1
<211> LENGTH: 4541
<212> TYPE: DNA
<213> ORGANISM: Homo sapiens
<220> FEATURE:
<221> NAME/KEY: CDS
<222> LOCATION: (192)...(4250)
<220> FEATURE:
<221> NAME/KEY: misc_feature
<222> LOCATION: (1)...(4541)
<223> OTHER INFORMATION: n = A,T,C or G

<400> SEQUENCE: 1
ggcggcggcg gcggagccct ggngtcggtg tctgcgcgct ggtgtctgag gcccaggctg        60
aggcctccgc tattgctgga gcgcaggcgg cggagaggat gactgccgct gccattctct       120
cttgagctag cgagccgccg ccaccctcca ccctcccccg gcagggcgga gaggagcggc       180
cggagtcagc g atg gtg ccc ggc gag gag aac caa ctg gtc ccg aaa gag       230
            Met Val Pro Gly Glu Glu Asn Gln Leu Val Pro Lys Glu
              1               5                  10 ata gaa aat gct gct gaa gaa cct aga gtc tta tgt att ata caa gat       278
Ile Glu Asn Ala Ala Glu Glu Pro Arg Val Leu Cys Ile Ile Gln Asp
     15                  20                  25
```

-continued

| | | |
|---|---|---|
| act act aat tca aag aca gtg aat gaa cgg atc act tta aat tta cca<br>Thr Thr Asn Ser Lys Thr Val Asn Glu Arg Ile Thr Leu Asn Leu Pro<br>30                 35               40                 45 | 326 |
| gca tct act cca gtc aga aag ctc ttt gaa gat gtg gcc aac aaa gta<br>Ala Ser Thr Pro Val Arg Lys Leu Phe Glu Asp Val Ala Asn Lys Val<br>                50                55               60 | 374 |
| ggc tac ata aat gga acc ttt gac ttg gtg tgg gga aat gga atc aat<br>Gly Tyr Ile Asn Gly Thr Phe Asp Leu Val Trp Gly Asn Gly Ile Asn<br>              65                70               75 | 422 |
| act gct gat atg gca cca ctg gat cat acc agt gac aag tca ctt ctc<br>Thr Ala Asp Met Ala Pro Leu Asp His Thr Ser Asp Lys Ser Leu Leu<br>        80                85               90 | 470 |
| gac gct aat ttt gag cca gga aag aag aac ttt ctg cat ttg aca gat<br>Asp Ala Asn Phe Glu Pro Gly Lys Lys Asn Phe Leu His Leu Thr Asp<br>        95              100              105 | 518 |
| aaa gat ggt gaa caa cct caa ata ctg ctg gag gat tcc agt gct ggg<br>Lys Asp Gly Glu Gln Pro Gln Ile Leu Leu Glu Asp Ser Ser Ala Gly<br>110                 115               120               125 | 566 |
| gaa gac agt gtt cat gac agg ttt ata ggt ccg ctt cca aga gaa ggt<br>Glu Asp Ser Val His Asp Arg Phe Ile Gly Pro Leu Pro Arg Glu Gly<br>                130              135              140 | 614 |
| tct gtg ggt tct acc agt gat tat gtc agc caa agc tac tcc tac tca<br>Ser Val Gly Ser Thr Ser Asp Tyr Val Ser Gln Ser Tyr Ser Tyr Ser<br>              145               150              155 | 662 |
| tct att ttg aat aaa tca gaa act gga tat gtg gga cta gta aac caa<br>Ser Ile Leu Asn Lys Ser Glu Thr Gly Tyr Val Gly Leu Val Asn Gln<br>        160                165              170 | 710 |
| gca atg act tgc tat ttg aat agc ctt tgc aaa cac ttt tta act cct<br>Ala Met Thr Cys Tyr Leu Asn Ser Leu Cys Lys His Phe Leu Thr Pro<br>175                 180               185 | 758 |
| gaa ttt agg aat gca tta tat aag tgg gaa ttt gaa gaa tct gaa gaa<br>Glu Phe Arg Asn Ala Leu Tyr Lys Trp Glu Phe Glu Glu Ser Glu Glu<br>190                 195               200              205 | 806 |
| gat cca gtg aca agt att cca tac caa ctt caa agg ctt tgt ttg tta<br>Asp Pro Val Thr Ser Ile Pro Tyr Gln Leu Gln Arg Leu Cys Leu Leu<br>                210              215              220 | 854 |
| caa acc agc aaa aag aga gca att gaa acc aca gat gtt aca agg agc<br>Gln Thr Ser Lys Lys Arg Ala Ile Glu Thr Thr Asp Val Thr Arg Ser<br>              225               230              235 | 902 |
| ttt gga tgg gat agt agt gag gct tgg cag cag cat gat gta caa gaa<br>Phe Gly Trp Asp Ser Ser Glu Ala Trp Gln Gln His Asp Val Gln Glu<br>        240                245              250 | 950 |
| cta tgc aga gtc atg ttt gat gct ttg gaa cag aaa tgg aag caa aca<br>Leu Cys Arg Val Met Phe Asp Ala Leu Glu Gln Lys Trp Lys Gln Thr<br>255                 260               265 | 998 |
| gaa cag gct gat ctt ata aat gag cta tat caa ggc aag ctg aag gac<br>Glu Gln Ala Asp Leu Ile Asn Glu Leu Tyr Gln Gly Lys Leu Lys Asp<br>270                 275               280              285 | 1046 |
| tac gtg aga tgt ctg gaa tgt ggt tat gag ggc tgg cga atc gac aca<br>Tyr Val Arg Cys Leu Glu Cys Gly Tyr Glu Gly Trp Arg Ile Asp Thr<br>                290              295              300 | 1094 |
| tat ctt gat att cca ttg gtc atc cga cct tat ggg tcc agc caa gca<br>Tyr Leu Asp Ile Pro Leu Val Ile Arg Pro Tyr Gly Ser Ser Gln Ala<br>              305               310              315 | 1142 |
| ttt gct agt gtg gaa gaa gca ttg cat gca ttt att cag cca gag att<br>Phe Ala Ser Val Glu Glu Ala Leu His Ala Phe Ile Gln Pro Glu Ile<br>        320                325              330 | 1190 |
| ctg gat ggc cca aat cag tat ttt tgt gaa cgt tgt aag aag aag tgt<br>Leu Asp Gly Pro Asn Gln Tyr Phe Cys Glu Arg Cys Lys Lys Lys Cys | 1238 |

```
                335                 340                 345
gat gca cgg aag ggc ctt cgg ttt ttg cat ttt cct tat ctg ctg acc     1286
Asp Ala Arg Lys Gly Leu Arg Phe Leu His Phe Pro Tyr Leu Leu Thr
350                 355                 360                 365 tta cag ctg aaa aga ttc gat ttt gat tat aca acc atg cat agg att     1334
Leu Gln Leu Lys Arg Phe Asp Phe Asp Tyr Thr Thr Met His Arg Ile
                370                 375                 380 aaa ctg aat gat cga atg aca ttt ccc gag gaa cta gat atg agt act     1382
Lys Leu Asn Asp Arg Met Thr Phe Pro Glu Glu Leu Asp Met Ser Thr
            385                 390                 395 ttt att gat gtt gaa gat gag aaa tct cct cag act gaa agt tgc act     1430
Phe Ile Asp Val Glu Asp Glu Lys Ser Pro Gln Thr Glu Ser Cys Thr
        400                 405                 410 gac agt gga gca gaa aat gaa ggt agt tgt cac agt gat cag atg agc     1478
Asp Ser Gly Ala Glu Asn Glu Gly Ser Cys His Ser Asp Gln Met Ser
    415                 420                 425 aac gat ttc tcc aat gat gat ggt gtt gat gaa gga atc tgt ctt gaa     1526
Asn Asp Phe Ser Asn Asp Asp Gly Val Asp Glu Gly Ile Cys Leu Glu
430                 435                 440                 445 acc aat agt gga act gaa aag atc tca aaa tct gga ctt gaa aag aat     1574
Thr Asn Ser Gly Thr Glu Lys Ile Ser Lys Ser Gly Leu Glu Lys Asn
                450                 455                 460 tcc ttg atc tat gaa ctt ttc tct gtt atg gtt cat tct ggg agc gct     1622
Ser Leu Ile Tyr Glu Leu Phe Ser Val Met Val His Ser Gly Ser Ala
            465                 470                 475 gct ggt ggt cat tat tat gca tgt ata aag tca ttc agt gat gag cag     1670
Ala Gly Gly His Tyr Tyr Ala Cys Ile Lys Ser Phe Ser Asp Glu Gln
        480                 485                 490 tgg tac agc ttc aat gat caa cat gtc agc agg ata aca caa gag gac     1718
Trp Tyr Ser Phe Asn Asp Gln His Val Ser Arg Ile Thr Gln Glu Asp
    495                 500                 505 att aag aaa aca cat ggt gga tct tca gga agc aga gga tat tat tct     1766
Ile Lys Lys Thr His Gly Gly Ser Ser Gly Ser Arg Gly Tyr Tyr Ser
510                 515                 520                 525 agt gct ttc gca agt tcc aca aat gca tat atg ctg atc tat aga ctg     1814
Ser Ala Phe Ala Ser Ser Thr Asn Ala Tyr Met Leu Ile Tyr Arg Leu
                530                 535                 540 aag gat cca gcc aga aat gca aaa ttt cta gaa gtg gat gaa tac cca     1862
Lys Asp Pro Ala Arg Asn Ala Lys Phe Leu Glu Val Asp Glu Tyr Pro
            545                 550                 555 gaa cat att aaa aac ttg gtg cag aaa gag aga gag ttg gaa gaa caa     1910
Glu His Ile Lys Asn Leu Val Gln Lys Glu Arg Glu Leu Glu Glu Gln
        560                 565                 570 gaa aag aga caa cga gaa att gag cgc aat aca tgc aag ata aaa tta     1958
Glu Lys Arg Gln Arg Glu Ile Glu Arg Asn Thr Cys Lys Ile Lys Leu
    575                 580                 585 ttc tgt ttg cat cct aca aaa caa gta atg atg gaa aat aaa ttg gag     2006
Phe Cys Leu His Pro Thr Lys Gln Val Met Met Glu Asn Lys Leu Glu
590                 595                 600                 605 gtt cat aag gat aag aca tta aag gaa gca gta gaa atg gct tat aag     2054
Val His Lys Asp Lys Thr Leu Lys Glu Ala Val Glu Met Ala Tyr Lys
                610                 615                 620 atg atg gat tta gaa gag gta ata ccc ctg gat tgc tgt cgc ctt gtt     2102
Met Met Asp Leu Glu Glu Val Ile Pro Leu Asp Cys Cys Arg Leu Val
            625                 630                 635 aaa tat gat gag ttt cat gat tat cta gaa cgg tca tat gaa gga gaa     2150
Lys Tyr Asp Glu Phe His Asp Tyr Leu Glu Arg Ser Tyr Glu Gly Glu
        640                 645                 650 gaa gat aca cca atg ggg ctt cta cta ggt ggc gtc aag tca aca tat     2198
```

```
                Glu Asp Thr Pro Met Gly Leu Leu Gly Gly Val Lys Ser Thr Tyr
                    655                 660                 665 atg ttt gat ctg ctg ttg gag acg aga aag cct gat cag gtt ttc caa              2246
Met Phe Asp Leu Leu Leu Glu Thr Arg Lys Pro Asp Gln Val Phe Gln
670                 675                 680                 685 tct tat aaa cct gga gaa gtg atg gtg aaa gtt cat gtt gtt gat cta              2294
Ser Tyr Lys Pro Gly Glu Val Met Val Lys Val His Val Val Asp Leu
                    690                 695                 700 aag gca gaa tct gta gct gct cct ata act gtt cgt gct tac tta aat              2342
Lys Ala Glu Ser Val Ala Ala Pro Ile Thr Val Arg Ala Tyr Leu Asn
            705                 710                 715 cag aca gtt aca gaa ttc aaa caa ctg att tca aag gcc atc cat tta              2390
Gln Thr Val Thr Glu Phe Lys Gln Leu Ile Ser Lys Ala Ile His Leu
        720                 725                 730 cct gct gaa aca atg aga ata gtg ctg gaa cgc tgc tac aat gat ttg              2438
Pro Ala Glu Thr Met Arg Ile Val Leu Glu Arg Cys Tyr Asn Asp Leu
735                 740                 745 cgt ctt ctc agt gtc tcc agt aaa acc ctg aaa gct gaa gga ttt ttt              2486
Arg Leu Leu Ser Val Ser Ser Lys Thr Leu Lys Ala Glu Gly Phe Phe
750                 755                 760                 765 aga agt aac aag gtg ttt gtt gaa agc tcc gag act ttg gat tac cag              2534
Arg Ser Asn Lys Val Phe Val Glu Ser Ser Glu Thr Leu Asp Tyr Gln
                    770                 775                 780 atg gcc ttt gca gac tct cat tta tgg aaa ctc ctg gat cgg cat gca              2582
Met Ala Phe Ala Asp Ser His Leu Trp Lys Leu Leu Asp Arg His Ala
            785                 790                 795 aat aca atc aga tta ttt gtt ttg cta cct gaa caa tcc cca gta tct              2630
Asn Thr Ile Arg Leu Phe Val Leu Leu Pro Glu Gln Ser Pro Val Ser
        800                 805                 810 tat tcc aaa agg aca gca tac cag aaa gct gga ggc gat tct ggt aat              2678
Tyr Ser Lys Arg Thr Ala Tyr Gln Lys Ala Gly Gly Asp Ser Gly Asn
815                 820                 825 gtg gat gat gac tgt gaa aga gtc aaa gga cct gta gga agc cta aag              2726
Val Asp Asp Asp Cys Glu Arg Val Lys Gly Pro Val Gly Ser Leu Lys
830                 835                 840                 845 tct gtg gaa gct att cta gaa gaa agc act gaa aaa ctc aaa agc ttg              2774
Ser Val Glu Ala Ile Leu Glu Glu Ser Thr Glu Lys Leu Lys Ser Leu
                    850                 855                 860 tca ctg cag caa cag cag gat gga gat aat ggg gac agc agc aaa agt              2822
Ser Leu Gln Gln Gln Gln Asp Gly Asp Asn Gly Asp Ser Ser Lys Ser
            865                 870                 875 act gag aca agt gac ttt gaa aac atc gaa tca cct ctc aat gag agg              2870
Thr Glu Thr Ser Asp Phe Glu Asn Ile Glu Ser Pro Leu Asn Glu Arg
        880                 885                 890 gac tct tca gca tca gtg gat aat aga gaa ctt gaa cag cat att cag              2918
Asp Ser Ser Ala Ser Val Asp Asn Arg Glu Leu Glu Gln His Ile Gln
895                 900                 905 act tct gat cca gaa aat ttt cag tct gaa gaa cga tca gac tca gat              2966
Thr Ser Asp Pro Glu Asn Phe Gln Ser Glu Glu Arg Ser Asp Ser Asp
910                 915                 920                 925 gtg aat aat gac agg agt aca agt tca gtg gac agt gat att ctt agc              3014
Val Asn Asn Asp Arg Ser Thr Ser Ser Val Asp Ser Asp Ile Leu Ser
                    930                 935                 940 tcc agt cat agc agt gat act ttg tgc aat gca gac aat gct cag atc              3062
Ser Ser His Ser Ser Asp Thr Leu Cys Asn Ala Asp Asn Ala Gln Ile
            945                 950                 955 cct ttg gct aat gga ctt gac tct cac agt atc aca agt agt aga aga              3110
Pro Leu Ala Asn Gly Leu Asp Ser His Ser Ile Thr Ser Ser Arg Arg
        960                 965                 970
```

-continued

| | | |
|---|---|---|
| acg aaa gca aat gaa ggg aaa aaa gaa aca tgg gat aca gca gaa gaa<br>Thr Lys Ala Asn Glu Gly Lys Lys Glu Thr Trp Asp Thr Ala Glu Glu<br>975 980 985 | | 3158 |
| gac tct gga act gat agt gaa tat gat gag agt ggc aag agt agg gga<br>Asp Ser Gly Thr Asp Ser Glu Tyr Asp Glu Ser Gly Lys Ser Arg Gly<br>990 995 1000 1005 | | 3206 |
| gaa atg cag tac atg tat ttc aaa gct gaa cct tat gct gca gat gaa<br>Glu Met Gln Tyr Met Tyr Phe Lys Ala Glu Pro Tyr Ala Ala Asp Glu<br>1010 1015 1020 | | 3254 |
| ggt tct ggg gaa gga cat aaa tgg ttg atg gtg cat gtt gat aaa aga<br>Gly Ser Gly Glu Gly His Lys Trp Leu Met Val His Val Asp Lys Arg<br>1025 1030 1035 | | 3302 |
| att act ctg gca gct ttc aaa caa cat tta gag ccc ttt gtt gga gtt<br>Ile Thr Leu Ala Ala Phe Lys Gln His Leu Glu Pro Phe Val Gly Val<br>1040 1045 1050 | | 3350 |
| ttg tcc tct cac ttc aag gtc ttt cga gtg tat gcc agc aat caa gag<br>Leu Ser Ser His Phe Lys Val Phe Arg Val Tyr Ala Ser Asn Gln Glu<br>1055 1060 1065 | | 3398 |
| ttt gag agc gtc cgg ctg aat gag aca ctt tca tca ttt tct gat gac<br>Phe Glu Ser Val Arg Leu Asn Glu Thr Leu Ser Ser Phe Ser Asp Asp<br>1070 1075 1080 1085 | | 3446 |
| aat aag att aca att aga ctg ggg aga gca ctt aaa aaa gga gaa tac<br>Asn Lys Ile Thr Ile Arg Leu Gly Arg Ala Leu Lys Lys Gly Glu Tyr<br>1090 1095 1100 | | 3494 |
| aga gtt aaa gta tac cag ctt ttg gtc aat gaa caa gag cca tgc aag<br>Arg Val Lys Val Tyr Gln Leu Leu Val Asn Glu Gln Glu Pro Cys Lys<br>1105 1110 1115 | | 3542 |
| ttt ctg cta gat gct gtg ttt gct aaa gga atg act gta cgg caa tca<br>Phe Leu Leu Asp Ala Val Phe Ala Lys Gly Met Thr Val Arg Gln Ser<br>1120 1125 1130 | | 3590 |
| aaa gag gaa tta att cct cag ctc agg gag caa tgt ggt tta gag ctc<br>Lys Glu Glu Leu Ile Pro Gln Leu Arg Glu Gln Cys Gly Leu Glu Leu<br>1135 1140 1145 | | 3638 |
| agt att gac agg ttt cgt cta agg aaa aaa aca tgg aag aat cct ggc<br>Ser Ile Asp Arg Phe Arg Leu Arg Lys Lys Thr Trp Lys Asn Pro Gly<br>1150 1155 1160 1165 | | 3686 |
| act gtc ttt ttg gat tat cat att tat gaa gaa gat att aat att tcc<br>Thr Val Phe Leu Asp Tyr His Ile Tyr Glu Glu Asp Ile Asn Ile Ser<br>1170 1175 1180 | | 3734 |
| agc aac tgg gag gtt ttc ctt gaa gtt ctt gat ggg gta gag aag atg<br>Ser Asn Trp Glu Val Phe Leu Glu Val Leu Asp Gly Val Glu Lys Met<br>1185 1190 1195 | | 3782 |
| aag tcc atg tca cag ctt gca gtt ttg tca aga cgg tgg aag cct tca<br>Lys Ser Met Ser Gln Leu Ala Val Leu Ser Arg Arg Trp Lys Pro Ser<br>1200 1205 1210 | | 3830 |
| gag atg aag ttg gat ccc ttc cag gag gtt gta ttg gaa agc agt agt<br>Glu Met Lys Leu Asp Pro Phe Gln Glu Val Val Leu Glu Ser Ser Ser<br>1215 1220 1225 | | 3878 |
| gtg gac gaa ttg cga gag aag ctt agt gaa atc agt ggg att cct ttg<br>Val Asp Glu Leu Arg Glu Lys Leu Ser Glu Ile Ser Gly Ile Pro Leu<br>1230 1235 1240 1245 | | 3926 |
| gat gat att gaa ttt gct aag ggt aga gga aca ttt ccc tgt gat att<br>Asp Asp Ile Glu Phe Ala Lys Gly Arg Gly Thr Phe Pro Cys Asp Ile<br>1250 1255 1260 | | 3974 |
| tct gtc ctt gat att cat caa gat tta gac tgg aat cct aaa gtt tct<br>Ser Val Leu Asp Ile His Gln Asp Leu Asp Trp Asn Pro Lys Val Ser<br>1265 1270 1275 | | 4022 |
| acc ctg aat gtc tgg cct ctt tat atc tgt gat gat ggt gcg gtc ata<br>Thr Leu Asn Val Trp Pro Leu Tyr Ile Cys Asp Asp Gly Ala Val Ile<br>1280 1285 1290 | | 4070 |

-continued

```
ttt tat agg gat aaa aca gaa gaa tta atg gaa ttg aca gat gag caa      4118
Phe Tyr Arg Asp Lys Thr Glu Glu Leu Met Glu Leu Thr Asp Glu Gln
    1295                1300                1305 aga aat gaa ctg atg aaa aaa gaa agc agt cga ctc cag aag act gga      4166
Arg Asn Glu Leu Met Lys Lys Glu Ser Ser Arg Leu Gln Lys Thr Gly
1310                1315                1320                1325 cat cgt gta aca tac tca cct cgt aaa gag aaa gca cta aaa ata tat      4214
His Arg Val Thr Tyr Ser Pro Arg Lys Glu Lys Ala Leu Lys Ile Tyr
                1330                1335                1340 ctg gat gga gca cca aat aaa gat ctg act caa gac tgactctgat           4260
Leu Asp Gly Ala Pro Asn Lys Asp Leu Thr Gln Asp
            1345                1350 agtgtagcat ttccctggg ggagttttgg ttttaattag atggttcact accactgggt     4320
agtgccattt tggccggaca tggttggggt aacccagtga caccagcact gattggactg    4380
ccctacacca atcagaagct cagtgcccaa tgggccactg ttttgactcg gaatcatgtt    4440
gtgcactata gtcaaatgta ctgtaaagtg aaaagggatg tgcaaaaaaa aaaaaaaaa     4500 agrcaaaaaa agctaacctt ctattagaaa aggggacagg g                        4541
```

<210> SEQ ID NO 2
<211> LENGTH: 1353
<212> TYPE: PRT
<213> ORGANISM: Homo sapiens

<400> SEQUENCE: 2

```
Met Val Pro Gly Glu Glu Asn Gln Leu Val Pro Lys Glu Ile Glu Asn
1               5                   10                  15

Ala Ala Glu Glu Pro Arg Val Leu Cys Ile Ile Gln Asp Thr Thr Asn
                20                  25                  30

Ser Lys Thr Val Asn Glu Arg Ile Thr Leu Asn Leu Pro Ala Ser Thr
            35                  40                  45

Pro Val Arg Lys Leu Phe Glu Asp Val Ala Asn Lys Val Gly Tyr Ile
        50                  55                  60

Asn Gly Thr Phe Asp Leu Val Trp Gly Asn Gly Ile Asn Thr Ala Asp
65                  70                  75                  80

Met Ala Pro Leu Asp His Thr Ser Asp Lys Ser Leu Leu Asp Ala Asn
                85                  90                  95

Phe Glu Pro Gly Lys Lys Asn Phe Leu His Leu Thr Asp Lys Asp Gly
                100                 105                 110

Glu Gln Pro Gln Ile Leu Leu Glu Asp Ser Ser Ala Gly Glu Asp Ser
            115                 120                 125

Val His Asp Arg Phe Ile Gly Pro Leu Pro Arg Glu Gly Ser Val Gly
        130                 135                 140

Ser Thr Ser Asp Tyr Val Ser Gln Ser Tyr Ser Ser Ile Leu
145                 150                 155                 160

Asn Lys Ser Glu Thr Gly Tyr Val Gly Leu Val Asn Gln Ala Met Thr
                165                 170                 175

Cys Tyr Leu Asn Ser Leu Cys Lys His Phe Leu Thr Pro Glu Phe Arg
            180                 185                 190

Asn Ala Leu Tyr Lys Trp Glu Phe Glu Glu Ser Glu Glu Asp Pro Val
        195                 200                 205

Thr Ser Ile Pro Tyr Gln Leu Gln Arg Leu Cys Leu Leu Gln Thr Ser
    210                 215                 220

Lys Lys Arg Ala Ile Glu Thr Thr Asp Val Thr Arg Ser Phe Gly Trp
225                 230                 235                 240
```

-continued

```
Asp Ser Ser Glu Ala Trp Gln Gln His Asp Val Gln Glu Leu Cys Arg
            245                 250                 255

Val Met Phe Asp Ala Leu Glu Gln Lys Trp Lys Gln Thr Glu Gln Ala
            260                 265                 270

Asp Leu Ile Asn Glu Leu Tyr Gln Gly Lys Leu Lys Asp Tyr Val Arg
            275                 280                 285

Cys Leu Glu Cys Gly Tyr Glu Gly Trp Arg Ile Asp Thr Tyr Leu Asp
            290                 295                 300

Ile Pro Leu Val Ile Arg Pro Tyr Gly Ser Ser Gln Ala Phe Ala Ser
305                 310                 315                 320

Val Glu Glu Ala Leu His Ala Phe Ile Gln Pro Glu Ile Leu Asp Gly
                    325                 330                 335

Pro Asn Gln Tyr Phe Cys Glu Arg Cys Lys Lys Cys Asp Ala Arg
                340                 345                 350

Lys Gly Leu Arg Phe Leu His Phe Pro Tyr Leu Leu Thr Leu Gln Leu
                355                 360                 365

Lys Arg Phe Asp Phe Asp Tyr Thr Thr Met His Arg Ile Lys Leu Asn
            370                 375                 380

Asp Arg Met Thr Phe Pro Glu Glu Leu Asp Met Ser Thr Phe Ile Asp
385                 390                 395                 400

Val Glu Asp Glu Lys Ser Pro Gln Thr Glu Ser Cys Thr Asp Ser Gly
                    405                 410                 415

Ala Glu Asn Glu Gly Ser Cys His Ser Asp Gln Met Ser Asn Asp Phe
                420                 425                 430

Ser Asn Asp Asp Gly Val Asp Glu Gly Ile Cys Leu Glu Thr Asn Ser
                435                 440                 445

Gly Thr Glu Lys Ile Ser Lys Ser Gly Leu Glu Lys Asn Ser Leu Ile
            450                 455                 460

Tyr Glu Leu Phe Ser Val Met Val His Ser Gly Ser Ala Ala Gly Gly
465                 470                 475                 480

His Tyr Tyr Ala Cys Ile Lys Ser Phe Ser Asp Glu Gln Trp Tyr Ser
                    485                 490                 495

Phe Asn Asp Gln His Val Ser Arg Ile Thr Gln Glu Asp Ile Lys Lys
                500                 505                 510

Thr His Gly Gly Ser Ser Gly Ser Arg Gly Tyr Tyr Ser Ser Ala Phe
            515                 520                 525

Ala Ser Ser Thr Asn Ala Tyr Met Leu Ile Tyr Arg Leu Lys Asp Pro
530                 535                 540

Ala Arg Asn Ala Lys Phe Leu Glu Val Asp Glu Tyr Pro Glu His Ile
545                 550                 555                 560

Lys Asn Leu Val Gln Lys Glu Arg Glu Leu Glu Gln Glu Lys Arg
                565                 570                 575

Gln Arg Glu Ile Glu Arg Asn Thr Cys Lys Ile Lys Leu Phe Cys Leu
            580                 585                 590

His Pro Thr Lys Gln Val Met Met Glu Asn Lys Leu Glu Val His Lys
            595                 600                 605

Asp Lys Thr Leu Lys Glu Ala Val Glu Met Ala Tyr Lys Met Met Asp
            610                 615                 620

Leu Glu Glu Val Ile Pro Leu Asp Cys Cys Arg Leu Val Lys Tyr Asp
625                 630                 635                 640

Glu Phe His Asp Tyr Leu Glu Arg Ser Tyr Glu Gly Glu Glu Asp Thr
                    645                 650                 655
```

```
Pro Met Gly Leu Leu Gly Gly Val Lys Ser Thr Tyr Met Phe Asp
        660             665             670
Leu Leu Leu Glu Thr Arg Lys Pro Asp Gln Val Phe Gln Ser Tyr Lys
            675             680             685
Pro Gly Glu Val Met Val Lys Val His Val Val Asp Leu Lys Ala Glu
        690             695             700
Ser Val Ala Ala Pro Ile Thr Val Arg Ala Tyr Leu Asn Gln Thr Val
705             710             715             720
Thr Glu Phe Lys Gln Leu Ile Ser Lys Ala Ile His Leu Pro Ala Glu
            725             730             735
Thr Met Arg Ile Val Leu Glu Arg Cys Tyr Asn Asp Leu Arg Leu Leu
        740             745             750
Ser Val Ser Ser Lys Thr Leu Lys Ala Glu Gly Phe Phe Arg Ser Asn
        755             760             765
Lys Val Phe Val Glu Ser Ser Glu Thr Leu Asp Tyr Gln Met Ala Phe
770             775             780
Ala Asp Ser His Leu Trp Lys Leu Leu Asp Arg His Ala Asn Thr Ile
785             790             795             800
Arg Leu Phe Val Leu Leu Pro Glu Gln Ser Pro Val Ser Tyr Ser Lys
            805             810             815
Arg Thr Ala Tyr Gln Lys Ala Gly Gly Asp Ser Gly Asn Val Asp Asp
        820             825             830
Asp Cys Glu Arg Val Lys Gly Pro Val Gly Ser Leu Lys Ser Val Glu
        835             840             845
Ala Ile Leu Glu Glu Ser Thr Glu Lys Leu Lys Ser Leu Ser Leu Gln
    850             855             860
Gln Gln Gln Asp Gly Asp Asn Gly Asp Ser Ser Lys Ser Thr Glu Thr
865             870             875             880
Ser Asp Phe Glu Asn Ile Glu Ser Pro Leu Asn Glu Arg Asp Ser Ser
            885             890             895
Ala Ser Val Asp Asn Arg Glu Leu Glu Gln His Ile Gln Thr Ser Asp
            900             905             910
Pro Glu Asn Phe Gln Ser Glu Arg Ser Asp Ser Asp Val Asn Asn
            915             920             925
Asp Arg Ser Thr Ser Ser Val Asp Ser Asp Ile Leu Ser Ser Ser His
        930             935             940
Ser Ser Asp Thr Leu Cys Asn Ala Asp Asn Ala Gln Ile Pro Leu Ala
945             950             955             960
Asn Gly Leu Asp Ser His Ser Ile Thr Ser Arg Arg Thr Lys Ala
            965             970             975
Asn Glu Gly Lys Lys Glu Thr Trp Asp Thr Ala Glu Glu Asp Ser Gly
            980             985             990
Thr Asp Ser Glu Tyr Asp Glu Ser Gly Lys Ser Arg Gly Glu Met Gln
        995             1000            1005
Tyr Met Tyr Phe Lys Ala Glu Pro Tyr Ala Ala Asp Glu Gly Ser Gly
    1010            1015            1020
Glu Gly His Lys Trp Leu Met Val His Val Asp Lys Arg Ile Thr Leu
1025            1030            1035            1040
Ala Ala Phe Lys Gln His Leu Glu Pro Phe Val Gly Val Leu Ser Ser
            1045            1050            1055
His Phe Lys Val Phe Arg Val Tyr Ala Ser Asn Gln Glu Phe Glu Ser
            1060            1065            1070
Val Arg Leu Asn Glu Thr Leu Ser Ser Phe Ser Asp Asp Asn Lys Ile
```

-continued

```
                  1075                1080                1085
Thr Ile Arg Leu Gly Arg Ala Leu Lys Lys Gly Glu Tyr Arg Val Lys
    1090                1095                1100

Val Tyr Gln Leu Leu Val Asn Glu Gln Glu Pro Cys Lys Phe Leu Leu
1105                1110                1115                1120

Asp Ala Val Phe Ala Lys Gly Met Thr Val Arg Gln Ser Lys Glu Glu
                1125                1130                1135

Leu Ile Pro Gln Leu Arg Glu Gln Cys Gly Leu Glu Leu Ser Ile Asp
                1140                1145                1150

Arg Phe Arg Leu Arg Lys Thr Trp Lys Asn Pro Gly Thr Val Phe
                1155                1160                1165

Leu Asp Tyr His Ile Tyr Glu Glu Asp Ile Asn Ile Ser Ser Asn Trp
    1170                1175                1180

Glu Val Phe Leu Glu Val Leu Asp Gly Val Glu Lys Met Lys Ser Met
1185                1190                1195                1200

Ser Gln Leu Ala Val Leu Ser Arg Arg Trp Lys Pro Ser Glu Met Lys
                1205                1210                1215

Leu Asp Pro Phe Gln Glu Val Val Leu Glu Ser Ser Val Asp Glu
                1220                1225                1230

Leu Arg Glu Lys Leu Ser Glu Ile Ser Gly Ile Pro Leu Asp Asp Ile
                1235                1240                1245

Glu Phe Ala Lys Gly Arg Gly Thr Phe Pro Cys Asp Ile Ser Val Leu
    1250                1255                1260

Asp Ile His Gln Asp Leu Asp Trp Asn Pro Lys Val Ser Thr Leu Asn
1265                1270                1275                1280

Val Trp Pro Leu Tyr Ile Cys Asp Asp Gly Ala Val Ile Phe Tyr Arg
                1285                1290                1295

Asp Lys Thr Glu Glu Leu Met Glu Leu Thr Asp Glu Gln Arg Asn Glu
                1300                1305                1310

Leu Met Lys Lys Glu Ser Ser Arg Leu Gln Lys Thr Gly His Arg Val
    1315                1320                1325

Thr Tyr Ser Pro Arg Lys Glu Lys Ala Leu Lys Ile Tyr Leu Asp Gly
    1330                1335                1340

Ala Pro Asn Lys Asp Leu Thr Gln Asp
1345                1350

<210> SEQ ID NO 3
<211> LENGTH: 4059
<212> TYPE: DNA
<213> ORGANISM: Homo sapiens
<220> FEATURE:
<221> NAME/KEY: CDS
<222> LOCATION: (1)...(4359)

<400> SEQUENCE: 3 atg gtg ccc ggc gag gag aac caa ctg gtc ccg aaa gag ata gaa aat      48
Met Val Pro Gly Glu Glu Asn Gln Leu Val Pro Lys Glu Ile Glu Asn
 1               5                  10                  15 gct gct gaa gaa cct aga gtc tta tgt att ata caa gat act act aat      96
Ala Ala Glu Glu Pro Arg Val Leu Cys Ile Ile Gln Asp Thr Thr Asn
            20                  25                  30 tca aag aca gtg aat gaa cgg atc act tta aat tta cca gca tct act     144
Ser Lys Thr Val Asn Glu Arg Ile Thr Leu Asn Leu Pro Ala Ser Thr
        35                  40                  45 cca gtc aga aag ctc ttt gaa gat gtg gcc aac aaa gta ggc tac ata     192
Pro Val Arg Lys Leu Phe Glu Asp Val Ala Asn Lys Val Gly Tyr Ile
    50                  55                  60
```

```
aat gga acc ttt gac ttg gtg tgg gga aat gga atc aat act gct gat       240
Asn Gly Thr Phe Asp Leu Val Trp Gly Asn Gly Ile Asn Thr Ala Asp
 65                  70                  75                  80 atg gca cca ctg gat cat acc agt gac aag tca ctt ctc gac gct aat       288
Met Ala Pro Leu Asp His Thr Ser Asp Lys Ser Leu Leu Asp Ala Asn
                 85                  90                  95 ttt gag cca gga aag aag aac ttt ctg cat ttg aca gat aaa gat ggt       336
Phe Glu Pro Gly Lys Lys Asn Phe Leu His Leu Thr Asp Lys Asp Gly
            100                 105                 110 gaa caa cct caa ata ctg ctg gag gat tcc agt gct ggg gaa gac agt       384
Glu Gln Pro Gln Ile Leu Leu Glu Asp Ser Ser Ala Gly Glu Asp Ser
        115                 120                 125 gtt cat gac agg ttt ata ggt ccg ctt cca aga gaa ggt tct gtg ggt       432
Val His Asp Arg Phe Ile Gly Pro Leu Pro Arg Glu Gly Ser Val Gly
130                 135                 140 tct acc agt gat tat gtc agc caa agc tac tcc tac tca tct att ttg       480
Ser Thr Ser Asp Tyr Val Ser Gln Ser Tyr Ser Tyr Ser Ser Ile Leu
145                 150                 155                 160 aat aaa tca gaa act gga tat gtg gga cta gta aac caa gca atg act       528
Asn Lys Ser Glu Thr Gly Tyr Val Gly Leu Val Asn Gln Ala Met Thr
                165                 170                 175 tgc tat ttg aat agc ctt tgc aaa cac ttt tta act cct gaa ttt agg       576
Cys Tyr Leu Asn Ser Leu Cys Lys His Phe Leu Thr Pro Glu Phe Arg
            180                 185                 190 aat gca tta tat aag tgg gaa ttt gaa gaa tct gaa gaa gat cca gtg       624
Asn Ala Leu Tyr Lys Trp Glu Phe Glu Glu Ser Glu Glu Asp Pro Val
        195                 200                 205 aca agt att cca tac caa ctt caa agg ctt tgt ttg tta caa acc agc       672
Thr Ser Ile Pro Tyr Gln Leu Gln Arg Leu Cys Leu Leu Gln Thr Ser
210                 215                 220 aaa aag aga gca att gaa acc aca gat gtt aca agg agc ttt gga tgg       720
Lys Lys Arg Ala Ile Glu Thr Thr Asp Val Thr Arg Ser Phe Gly Trp
225                 230                 235                 240 gat agt agt gag gct tgg cag cag cat gat gta caa gaa cta tgc aga       768
Asp Ser Ser Glu Ala Trp Gln Gln His Asp Val Gln Glu Leu Cys Arg
                245                 250                 255 gtc atg ttt gat gct ttg gaa cag aaa tgg aag caa aca gaa cag gct       816
Val Met Phe Asp Ala Leu Glu Gln Lys Trp Lys Gln Thr Glu Gln Ala
            260                 265                 270 gat ctt ata aat gag cta tat caa ggc aag ctg aag gac tac gtg aga       864
Asp Leu Ile Asn Glu Leu Tyr Gln Gly Lys Leu Lys Asp Tyr Val Arg
        275                 280                 285 tgt ctg gaa tgt ggt tat gag ggc tgg cga atc gac aca tat ctt gat       912
Cys Leu Glu Cys Gly Tyr Glu Gly Trp Arg Ile Asp Thr Tyr Leu Asp
290                 295                 300 att cca ttg gtc atc cga cct tat ggg tcc agc caa gca ttt gct agt       960
Ile Pro Leu Val Ile Arg Pro Tyr Gly Ser Ser Gln Ala Phe Ala Ser
305                 310                 315                 320 gtg gaa gaa gca ttg cat gca ttt att cag cca gag att ctg gat ggc      1008
Val Glu Glu Ala Leu His Ala Phe Ile Gln Pro Glu Ile Leu Asp Gly
                325                 330                 335 cca aat cag tat ttt tgt gaa cgt tgt aag aag aag tgt gat gca cgg      1056
Pro Asn Gln Tyr Phe Cys Glu Arg Cys Lys Lys Lys Cys Asp Ala Arg
            340                 345                 350 aag ggc ctt cgg ttt ttg cat ttt cct tat ctg ctg acc tta cag ctg      1104
Lys Gly Leu Arg Phe Leu His Phe Pro Tyr Leu Leu Thr Leu Gln Leu
        355                 360                 365 aaa aga ttc gat ttt gat tat aca acc atg cat agg att aaa ctg aat      1152
Lys Arg Phe Asp Phe Asp Tyr Thr Thr Met His Arg Ile Lys Leu Asn
```

```
                  370                 375                 380
gat cga atg aca ttt ccc gag gaa cta gat atg agt act ttt att gat     1200
Asp Arg Met Thr Phe Pro Glu Glu Leu Asp Met Ser Thr Phe Ile Asp
385                 390                 395                 400 gtt gaa gat gag aaa tct cct cag act gaa agt tgc act gac agt gga     1248
Val Glu Asp Glu Lys Ser Pro Gln Thr Glu Ser Cys Thr Asp Ser Gly
                405                 410                 415 gca gaa aat gaa ggt agt tgt cac agt gat cag atg agc aac gat ttc     1296
Ala Glu Asn Glu Gly Ser Cys His Ser Asp Gln Met Ser Asn Asp Phe
            420                 425                 430 tcc aat gat gat ggt gtt gat gaa gga atc tgt ctt gaa acc aat agt     1344
Ser Asn Asp Asp Gly Val Asp Glu Gly Ile Cys Leu Glu Thr Asn Ser
        435                 440                 445 gga act gaa aag atc tca aaa tct gga ctt gaa aag aat tcc ttg atc     1392
Gly Thr Glu Lys Ile Ser Lys Ser Gly Leu Glu Lys Asn Ser Leu Ile
450                 455                 460 tat gaa ctt ttc tct gtt atg gtt cat tct ggg agc gct gct ggt ggt     1440
Tyr Glu Leu Phe Ser Val Met Val His Ser Gly Ser Ala Ala Gly Gly
465                 470                 475                 480 cat tat tat gca tgt ata aag tca ttc agt gat gag cag tgg tac agc     1488
His Tyr Tyr Ala Cys Ile Lys Ser Phe Ser Asp Glu Gln Trp Tyr Ser
                485                 490                 495 ttc aat gat caa cat gtc agc agg ata aca caa gag gac att aag aaa     1536
Phe Asn Asp Gln His Val Ser Arg Ile Thr Gln Glu Asp Ile Lys Lys
            500                 505                 510 aca cat ggt gga tct tca gga agc aga gga tat tat tct agt gct ttc     1584
Thr His Gly Gly Ser Ser Gly Ser Arg Gly Tyr Tyr Ser Ser Ala Phe
        515                 520                 525 gca agt tcc aca aat gca tat atg ctg atc tat aga ctg aag gat cca     1632
Ala Ser Ser Thr Asn Ala Tyr Met Leu Ile Tyr Arg Leu Lys Asp Pro
530                 535                 540 gcc aga aat gca aaa ttt cta gaa gtg gat gaa tac cca gaa cat att     1680
Ala Arg Asn Ala Lys Phe Leu Glu Val Asp Glu Tyr Pro Glu His Ile
545                 550                 555                 560 aaa aac ttg gtg cag aaa gag aga gag ttg gaa gaa caa gaa aag aga     1728
Lys Asn Leu Val Gln Lys Glu Arg Glu Leu Glu Glu Gln Glu Lys Arg
                565                 570                 575 caa cga gaa att gag cgc aat aca tgc aag ata aaa tta ttc tgt ttg     1776
Gln Arg Glu Ile Glu Arg Asn Thr Cys Lys Ile Lys Leu Phe Cys Leu
            580                 585                 590 cat cct aca aaa caa gta atg atg gaa aat aaa ttg gag gtt cat aag     1824
His Pro Thr Lys Gln Val Met Met Glu Asn Lys Leu Glu Val His Lys
        595                 600                 605 gat aag aca tta aag gaa gca gta gaa atg gct tat aag atg atg gat     1872
Asp Lys Thr Leu Lys Glu Ala Val Glu Met Ala Tyr Lys Met Met Asp
610                 615                 620 tta gaa gag gta ata ccc ctg gat tgc tgt cgc ctt gtt aaa tat gat     1920
Leu Glu Glu Val Ile Pro Leu Asp Cys Cys Arg Leu Val Lys Tyr Asp
625                 630                 635                 640 gag ttt cat gat tat cta gaa cgg tca tat gaa gga gaa gaa gat aca     1968
Glu Phe His Asp Tyr Leu Glu Arg Ser Tyr Glu Gly Glu Glu Asp Thr
                645                 650                 655 cca atg ggg ctt cta cta ggt ggc gtc aag tca aca tat atg ttt gat     2016
Pro Met Gly Leu Leu Leu Gly Gly Val Lys Ser Thr Tyr Met Phe Asp
            660                 665                 670 ctg ctg ttg gag acg aga aag cct gat cag gtt ttc caa tct tat aaa     2064
Leu Leu Leu Glu Thr Arg Lys Pro Asp Gln Val Phe Gln Ser Tyr Lys
        675                 680                 685 cct gga gaa gtg atg gtg aaa gtt cat gtt gtt gat cta aag gca gaa     2112
```

|  |  |
|---|---|
| Pro Gly Glu Val Met Val Lys Val His Val Val Asp Leu Lys Ala Glu<br>    690                        695                        700 |  |
| tct gta gct gct cct ata act gtt cgt gct tac tta aat cag aca gtt<br>Ser Val Ala Ala Pro Ile Thr Val Arg Ala Tyr Leu Asn Gln Thr Val<br>705                   710                     715                    720 | 2160 |
| aca gaa ttc aaa caa ctg att tca aag gcc atc cat tta cct gct gaa<br>Thr Glu Phe Lys Gln Leu Ile Ser Lys Ala Ile His Leu Pro Ala Glu<br>                   725                     730                    735 | 2208 |
| aca atg aga ata gtg ctg gaa cgc tgc tac aat gat ttg cgt ctt ctc<br>Thr Met Arg Ile Val Leu Glu Arg Cys Tyr Asn Asp Leu Arg Leu Leu<br>              740                     745                    750 | 2256 |
| agt gtc tcc agt aaa acc ctg aaa gct gaa gga ttt ttt aga agt aac<br>Ser Val Ser Ser Lys Thr Leu Lys Ala Glu Gly Phe Phe Arg Ser Asn<br>         755                     760                    765 | 2304 |
| aag gtg ttt gtt gaa agc tcc gag act ttg gat tac cag atg gcc ttt<br>Lys Val Phe Val Glu Ser Ser Glu Thr Leu Asp Tyr Gln Met Ala Phe<br>770                   775                     780 | 2352 |
| gca gac tct cat tta tgg aaa ctc ctg gat cgg cat gca aat aca atc<br>Ala Asp Ser His Leu Trp Lys Leu Leu Asp Arg His Ala Asn Thr Ile<br>785                   790                     795                    800 | 2400 |
| aga tta ttt gtt ttg cta cct gaa caa tcc cca gta tct tat tcc aaa<br>Arg Leu Phe Val Leu Leu Pro Glu Gln Ser Pro Val Ser Tyr Ser Lys<br>                   805                     810                    815 | 2448 |
| agg aca gca tac cag aaa gct gga ggc gat tct ggt aat gtg gat gat<br>Arg Thr Ala Tyr Gln Lys Ala Gly Gly Asp Ser Gly Asn Val Asp Asp<br>              820                     825                    830 | 2496 |
| gac tgt gaa aga gtc aaa gga cct gta gga agc cta aag tct gtg gaa<br>Asp Cys Glu Arg Val Lys Gly Pro Val Gly Ser Leu Lys Ser Val Glu<br>         835                     840                    845 | 2544 |
| gct att cta gaa gaa agc act gaa aaa ctc aaa agc ttg tca ctg cag<br>Ala Ile Leu Glu Glu Ser Thr Glu Lys Leu Lys Ser Leu Ser Leu Gln<br>850                   855                     860 | 2592 |
| caa cag cag gat gga gat aat ggg gac agc agc aaa agt act gag aca<br>Gln Gln Gln Asp Gly Asp Asn Gly Asp Ser Ser Lys Ser Thr Glu Thr<br>865                   870                     875                    880 | 2640 |
| agt gac ttt gaa aac atc gaa tca cct ctc aat gag agg gac tct tca<br>Ser Asp Phe Glu Asn Ile Glu Ser Pro Leu Asn Glu Arg Asp Ser Ser<br>                   885                     890                    895 | 2688 |
| gca tca gtg gat aat aga gaa ctt gaa cag cat att cag act tct gat<br>Ala Ser Val Asp Asn Arg Glu Leu Glu Gln His Ile Gln Thr Ser Asp<br>              900                     905                    910 | 2736 |
| cca gaa aat ttt cag tct gaa gaa cga tca gac tca gat gtg aat aat<br>Pro Glu Asn Phe Gln Ser Glu Glu Arg Ser Asp Ser Asp Val Asn Asn<br>         915                     920                    925 | 2784 |
| gac agg agt aca agt tca gtg gac agt gat att ctt agc tcc agt cat<br>Asp Arg Ser Thr Ser Ser Val Asp Ser Asp Ile Leu Ser Ser Ser His<br>930                   935                     940 | 2832 |
| agc agt gat act ttg tgc aat gca gac aat gct cag atc cct ttg gct<br>Ser Ser Asp Thr Leu Cys Asn Ala Asp Asn Ala Gln Ile Pro Leu Ala<br>945                   950                     955                    960 | 2880 |
| aat gga ctt gac tct cac agt atc aca agt agt aga aga acg aaa gca<br>Asn Gly Leu Asp Ser His Ser Ile Thr Ser Ser Arg Arg Thr Lys Ala<br>                   965                     970                    975 | 2928 |
| aat gaa ggg aaa aaa gaa aca tgg gat aca gca gaa gaa gac tct gga<br>Asn Glu Gly Lys Lys Glu Thr Trp Asp Thr Ala Glu Glu Asp Ser Gly<br>              980                     985                    990 | 2976 |
| act gat agt gaa tat gat gag agt ggc aag agt agg gga gaa atg cag<br>Thr Asp Ser Glu Tyr Asp Glu Ser Gly Lys Ser Arg Gly Glu Met Gln<br>         995                     1000                 1005 | 3024 |

```
tac atg tat ttc aaa gct gaa cct tat gct gca gat gaa ggt tct ggg    3072
Tyr Met Tyr Phe Lys Ala Glu Pro Tyr Ala Ala Asp Glu Gly Ser Gly
    1010                1015                1020 gaa gga cat aaa tgg ttg atg gtg cat gtt gat aaa aga att act ctg    3120
Glu Gly His Lys Trp Leu Met Val His Val Asp Lys Arg Ile Thr Leu
1025            1030                1035                1040 gca gct ttc aaa caa cat tta gag ccc ttt gtt gga gtt ttg tcc tct    3168
Ala Ala Phe Lys Gln His Leu Glu Pro Phe Val Gly Val Leu Ser Ser
                1045                1050                1055 cac ttc aag gtc ttt cga gtg tat gcc agc aat caa gag ttt gag agc    3216
His Phe Lys Val Phe Arg Val Tyr Ala Ser Asn Gln Glu Phe Glu Ser
            1060                1065                1070 gtc cgg ctg aat gag aca ctt tca tca ttt tct gat gac aat aag att    3264
Val Arg Leu Asn Glu Thr Leu Ser Ser Phe Ser Asp Asp Asn Lys Ile
        1075                1080                1085 aca att aga ctg ggg aga gca ctt aaa aaa gga gaa tac aga gtt aaa    3312
Thr Ile Arg Leu Gly Arg Ala Leu Lys Lys Gly Glu Tyr Arg Val Lys
    1090                1095                1100 gta tac cag ctt ttg gtc aat gaa caa gag cca tgc aag ttt ctg cta    3360
Val Tyr Gln Leu Leu Val Asn Glu Gln Glu Pro Cys Lys Phe Leu Leu
1105            1110                1115                1120 gat gct gtg ttt gct aaa gga atg act gta cgg caa tca aaa gag gaa    3408
Asp Ala Val Phe Ala Lys Gly Met Thr Val Arg Gln Ser Lys Glu Glu
                1125                1130                1135 tta att cct cag ctc agg gag caa tgt ggt tta gag ctc agt att gac    3456
Leu Ile Pro Gln Leu Arg Glu Gln Cys Gly Leu Glu Leu Ser Ile Asp
            1140                1145                1150 agg ttt cgt cta agg aaa aaa aca tgg aag aat cct ggc act gtc ttt    3504
Arg Phe Arg Leu Arg Lys Lys Thr Trp Lys Asn Pro Gly Thr Val Phe
        1155                1160                1165 ttg gat tat cat att tat gaa gaa gat att aat att tcc agc aac tgg    3552
Leu Asp Tyr His Ile Tyr Glu Glu Asp Ile Asn Ile Ser Ser Asn Trp
    1170                1175                1180 gag gtt ttc ctt gaa gtt ctt gat ggg gta gag aag atg aag tcc atg    3600
Glu Val Phe Leu Glu Val Leu Asp Gly Val Glu Lys Met Lys Ser Met
1185            1190                1195                1200 tca cag ctt gca gtt ttg tca aga cgg tgg aag cct tca gag atg aag    3648
Ser Gln Leu Ala Val Leu Ser Arg Arg Trp Lys Pro Ser Glu Met Lys
                1205                1210                1215 ttg gat ccc ttc cag gag gtt gta ttg gaa agc agt agt gtg gac gaa    3696
Leu Asp Pro Phe Gln Glu Val Val Leu Glu Ser Ser Ser Val Asp Glu
            1220                1225                1230 ttg cga gag aag ctt agt gaa atc agt ggg att cct ttg gat gat att    3744
Leu Arg Glu Lys Leu Ser Glu Ile Ser Gly Ile Pro Leu Asp Asp Ile
        1235                1240                1245 gaa ttt gct aag ggt aga gga aca ttt ccc tgt gat att tct gtc ctt    3792
Glu Phe Ala Lys Gly Arg Gly Thr Phe Pro Cys Asp Ile Ser Val Leu
    1250                1255                1260 gat att cat caa gat tta gac tgg aat cct aaa gtt tct acc ctg aat    3840
Asp Ile His Gln Asp Leu Asp Trp Asn Pro Lys Val Ser Thr Leu Asn
1265            1270                1275                1280 gtc tgg cct ctt tat atc tgt gat gat ggt gcg gtc ata ttt tat agg    3888
Val Trp Pro Leu Tyr Ile Cys Asp Asp Gly Ala Val Ile Phe Tyr Arg
                1285                1290                1295 gat aaa aca gaa gaa tta atg gaa tta aca gat gag caa aga aat gaa    3936
Asp Lys Thr Glu Glu Leu Met Glu Leu Thr Asp Glu Gln Arg Asn Glu
            1300                1305                1310 ctg atg aaa aaa gaa agc agt cga ctc cag aag act gga cat cgt gta    3984
Leu Met Lys Lys Glu Ser Ser Arg Leu Gln Lys Thr Gly His Arg Val
        1315                1320                1325
```

```
aca tac tca cct cgt aaa gag aaa gca cta aaa ata tat ctg gat gga    4032
Thr Tyr Ser Pro Arg Lys Glu Lys Ala Leu Lys Ile Tyr Leu Asp Gly
    1330                1335                1340 gca cca aat aaa gat ctg act caa gac                                 4059
Ala Pro Asn Lys Asp Leu Thr Gln Asp Asp Asp Asp Asp Asp Asp
1345                1350                1355                1360

Asp Asp Asp Asp Asp Asp Asp Asp Asp Asp Asp Asp Asp                 4059
            1365                1370                1375

Asp Asp Asp Asp Asp Asp Asp Asp Asp Asp Asp Asp                     4059
        1380                1385                1390

Asp Asp Asp Asp Asp Asp Asp Asp Asp Asp Asp Asp                     4059
        1395                1400                1405

Asp Asp Asp Asp Asp Asp Asp Asp Asp Asp Asp Asp                     4059
        1410                1415                1420

Asp Asp Asp Asp Asp Asp Asp Asp Asp Asp Asp Asp                     4059
1425                1430                1435                1440

Asp Asp Asp Asp Asp Asp Asp Asp Asp Asp
            1445                1450
```

```
<210> SEQ ID NO 4
<211> LENGTH: 32
<212> TYPE: PRT
<213> ORGANISM: Artificial Sequence
<220> FEATURE:
<223> OTHER INFORMATION: Consensus

<400> SEQUENCE: 4

Thr Gly Leu Ile Asn Leu Gly Asn Thr Cys Tyr Met Asn Ser Val Leu
 1               5                  10                  15

Gln Cys Leu Phe Ser Ile Pro Pro Leu Arg Asp Tyr Leu Leu Asp Ile
            20                  25                  30

<210> SEQ ID NO 5
<211> LENGTH: 69
<212> TYPE: PRT
<213> ORGANISM: Artificial Sequence
<220> FEATURE:
<223> OTHER INFORMATION: Consensus

<400> SEQUENCE: 5

Gly Pro Gly Lys Tyr Glu Leu Tyr Ala Val Val His Ser Gly Ser
 1               5                  10                  15

Ser Leu Ser Gly Gly His Tyr Thr Ala Tyr Val Lys Lys Glu Asn Trp
            20                  25                  30

Tyr Lys Phe Asp Asp Asp Lys Val Ser Arg Val Thr Glu Glu Glu Val
        35                  40                  45

Leu Lys Glu Ser Gly Gly Glu Ser Gly Asp Thr Ser Ser Ala Tyr Ile
    50                  55                  60

Leu Phe Tyr Glu Arg
65

<210> SEQ ID NO 6
<211> LENGTH: 2736
<212> TYPE: DNA
<213> ORGANISM: Homo sapiens
<220> FEATURE:
<221> NAME/KEY: CDS
<222> LOCATION: (50)...(2491)

<400> SEQUENCE: 6
```

-continued

```
tagtccacgc gtccgcggac gcgtgggcgg cccggcgggt aaataacag atg cgg gtg      58
                                                      Met Arg Val
                                                        1 aaa gat cca act aaa gct tta cct gag aaa gcc aaa aga agt aaa agg      106
Lys Asp Pro Thr Lys Ala Leu Pro Glu Lys Ala Lys Arg Ser Lys Arg
  5              10                  15 cct act gta cct cat gat gaa gac tct tca gat gat att gct gta ggt      154
Pro Thr Val Pro His Asp Glu Asp Ser Ser Asp Asp Ile Ala Val Gly
 20              25                  30                  35 tta act tgc caa cat gta agt cat gct atc agc gtg aat cat gta aag      202
Leu Thr Cys Gln His Val Ser His Ala Ile Ser Val Asn His Val Lys
                 40                  45                  50 aga gca ata gct gag aat ctg tgg tca gtt tgc tca gaa tgt tta aaa      250
Arg Ala Ile Ala Glu Asn Leu Trp Ser Val Cys Ser Glu Cys Leu Lys
             55                  60                  65 gaa aga aga ttc tat gat ggg cag cta gta ctt act tct gat att tgg      298
Glu Arg Arg Phe Tyr Asp Gly Gln Leu Val Leu Thr Ser Asp Ile Trp
         70                  75                  80 ttg tgc ctc aag tgt ggc ttc cag gga tgt ggt aaa aac tca gaa agc      346
Leu Cys Leu Lys Cys Gly Phe Gln Gly Cys Gly Lys Asn Ser Glu Ser
     85                  90                  95 caa cat tca ttg aag cac ttt aag agt tcc aga aca gag ccc cat tgt      394
Gln His Ser Leu Lys His Phe Lys Ser Ser Arg Thr Glu Pro His Cys
100             105                 110                 115 att ata att aat ctg agc aca tgg att ata tgg tgt tat gaa tgt gat      442
Ile Ile Ile Asn Leu Ser Thr Trp Ile Ile Trp Cys Tyr Glu Cys Asp
                120                 125                 130 gaa aaa tta tca acg cat tgt aat aag aag gtt ttg gct cag ata gtt      490
Glu Lys Leu Ser Thr His Cys Asn Lys Lys Val Leu Ala Gln Ile Val
            135                 140                 145 gat ttt ctc cag aaa cat gct tct aaa aca caa aca agt gca ttt tct      538
Asp Phe Leu Gln Lys His Ala Ser Lys Thr Gln Thr Ser Ala Phe Ser
        150                 155                 160 aga atc atg aaa ctt tgt gaa gaa aaa tgt gaa aca gat gaa ata cag      586
Arg Ile Met Lys Leu Cys Glu Glu Lys Cys Glu Thr Asp Glu Ile Gln
    165                 170                 175 aag gga gga aaa tgc aga aat tta tct gta aga gga att aca aat tta      634
Lys Gly Gly Lys Cys Arg Asn Leu Ser Val Arg Gly Ile Thr Asn Leu
180                 185                 190                 195 gga aat act tgc ttt ttt aat gca gtc atg cag aac ttg gca cag act      682
Gly Asn Thr Cys Phe Phe Asn Ala Val Met Gln Asn Leu Ala Gln Thr
                200                 205                 210 tat act ctt act gat ctg atg aat gag atc aaa gaa agt agt aca aaa      730
Tyr Thr Leu Thr Asp Leu Met Asn Glu Ile Lys Glu Ser Ser Thr Lys
            215                 220                 225 ctc aag att ttt cct tcc tca gac tct cag ctg gac cca ttg gtg gtg      778
Leu Lys Ile Phe Pro Ser Ser Asp Ser Gln Leu Asp Pro Leu Val Val
        230                 235                 240 gaa ctt tca agg cct gga cca ctg acc tca gcc ttg ttc ctg ttt ctt      826
Glu Leu Ser Arg Pro Gly Pro Leu Thr Ser Ala Leu Phe Leu Phe Leu
    245                 250                 255 cac agc atg aag gag act gaa aaa gga cca ctt tct cct aaa gtt ctt      874
His Ser Met Lys Glu Thr Glu Lys Gly Pro Leu Ser Pro Lys Val Leu
260                 265                 270                 275 ttt aat cag ctt tgt cag aag gca cct cga ttt aaa gat ttc cag caa      922
Phe Asn Gln Leu Cys Gln Lys Ala Pro Arg Phe Lys Asp Phe Gln Gln
                280                 285                 290 cag gac agt cag gag ctt ctt cat tat ctt ctg gat gca gtg agg aca      970
Gln Asp Ser Gln Glu Leu Leu His Tyr Leu Leu Asp Ala Val Arg Thr
            295                 300                 305
```

-continued

```
gaa gaa aca aag cga ata caa gct agc att cta aaa gca ttt aac aac      1018
Glu Glu Thr Lys Arg Ile Gln Ala Ser Ile Leu Lys Ala Phe Asn Asn
        310                 315                 320 cca act act aaa act gct gat gat gaa act aga aaa aaa gtc aaa gca      1066
Pro Thr Thr Lys Thr Ala Asp Asp Glu Thr Arg Lys Lys Val Lys Ala
325                 330                 335 tat gga aaa gaa ggt gtg aaa atg aac ttc ata gat cgg atc ttt att      1114
Tyr Gly Lys Glu Gly Val Lys Met Asn Phe Ile Asp Arg Ile Phe Ile
340                 345                 350                 355 ggt gaa tta act agc acg gtc atg tgt gaa gaa tgt gca aat atc tcc      1162
Gly Glu Leu Thr Ser Thr Val Met Cys Glu Glu Cys Ala Asn Ile Ser
                360                 365                 370 acg gtg aaa gat cca ttc att gat att tca ctt cct ata ata gaa gaa      1210
Thr Val Lys Asp Pro Phe Ile Asp Ile Ser Leu Pro Ile Ile Glu Glu
            375                 380                 385 agg gtt tca aaa cct tta ctt tgg gga aga atg aat aaa tat aga agt      1258
Arg Val Ser Lys Pro Leu Leu Trp Gly Arg Met Asn Lys Tyr Arg Ser
        390                 395                 400 tta cgg gag aca gat cat gat cga tac agt ggc aat gtt act ata gaa      1306
Leu Arg Glu Thr Asp His Asp Arg Tyr Ser Gly Asn Val Thr Ile Glu
405                 410                 415 aat att cat caa cct aga gct gcc aag aag cat tct tca tct aaa gat      1354
Asn Ile His Gln Pro Arg Ala Ala Lys Lys His Ser Ser Ser Lys Asp
420                 425                 430                 435 aag aga caa cta att cat gac cga aaa tgt att aga aaa ttg tca tct      1402
Lys Arg Gln Leu Ile His Asp Arg Lys Cys Ile Arg Lys Leu Ser Ser
                440                 445                 450 gga gaa act gtc aca tac cag aaa aat gaa aac ctt gaa atg aat ggg      1450
Gly Glu Thr Val Thr Tyr Gln Lys Asn Glu Asn Leu Glu Met Asn Gly
            455                 460                 465 gat tct tta atg ttt gcc agc ctc atg aat tct gag tca cgt ctg aat      1498
Asp Ser Leu Met Phe Ala Ser Leu Met Asn Ser Glu Ser Arg Leu Asn
        470                 475                 480 gaa agc cct act gat gac agt gaa aaa gaa gcc agc cat tct gaa agc      1546
Glu Ser Pro Thr Asp Asp Ser Glu Lys Glu Ala Ser His Ser Glu Ser
485                 490                 495 aat gtt gat gct gac agt gag cct tca gaa tct gaa agt gct tca aag      1594
Asn Val Asp Ala Asp Ser Glu Pro Ser Glu Ser Glu Ser Ala Ser Lys
500                 505                 510                 515 cag act ggg ctg ttc aga tcc agt agt gga tcc ggt gtg cag cca gat      1642
Gln Thr Gly Leu Phe Arg Ser Ser Ser Gly Ser Gly Val Gln Pro Asp
                520                 525                 530 gga ccc ctt tac cct ctg tca gca ggt aaa ctg ctg tac acc aag gag      1690
Gly Pro Leu Tyr Pro Leu Ser Ala Gly Lys Leu Leu Tyr Thr Lys Glu
            535                 540                 545 act gac agt ggt gat aag gaa atg gca gaa gct att tct gaa ctt cgt      1738
Thr Asp Ser Gly Asp Lys Glu Met Ala Glu Ala Ile Ser Glu Leu Arg
        550                 555                 560 ttg agc agc act gta act ggg gat caa gat ttt gac aga gaa aat cag      1786
Leu Ser Ser Thr Val Thr Gly Asp Gln Asp Phe Asp Arg Glu Asn Gln
565                 570                 575 cca cta aat att tca aat aat tta tgt ttt tta gag ggg aag cat ttg      1834
Pro Leu Asn Ile Ser Asn Asn Leu Cys Phe Leu Glu Gly Lys His Leu
580                 585                 590                 595 agg tct tat agt ccc caa aat gct ttt cag acc ctt tct cag agc tat      1882
Arg Ser Tyr Ser Pro Gln Asn Ala Phe Gln Thr Leu Ser Gln Ser Tyr
                600                 605                 610 ata act act tct aaa gaa tgt tca att cag tcc tgt ctc tac cag ttt      1930
Ile Thr Thr Ser Lys Glu Cys Ser Ile Gln Ser Cys Leu Tyr Gln Phe
```

-continued

```
           615                 620                 625
aca tct atg gaa tta cta atg ggg aat aat aag ctt cta tgt gag aat    1978
Thr Ser Met Glu Leu Leu Met Gly Asn Asn Lys Leu Leu Cys Glu Asn
        630                 635                 640 tgt act aaa aac aaa cag aag tac caa gaa gaa acc agt ttt gca gaa    2026
Cys Thr Lys Asn Lys Gln Lys Tyr Gln Glu Glu Thr Ser Phe Ala Glu
    645                 650                 655 aag aaa gta gaa gga gtt tat act aat gcc agg aag caa ttg ctc att    2074
Lys Lys Val Glu Gly Val Tyr Thr Asn Ala Arg Lys Gln Leu Leu Ile
660                 665                 670                 675 tct gct gtt cca gct gtc cta att ctc cac ctg aaa aga ttt cat cag    2122
Ser Ala Val Pro Ala Val Leu Ile Leu His Leu Lys Arg Phe His Gln
                680                 685                 690 gct ggc ttg agt ctt cgt aaa gta aac aga cat gta gat ttt cca ctt    2170
Ala Gly Leu Ser Leu Arg Lys Val Asn Arg His Val Asp Phe Pro Leu
            695                 700                 705 atg ctc gat tta gca cca ttc tgc tct gct act tgt aag aat gca agt    2218
Met Leu Asp Leu Ala Pro Phe Cys Ser Ala Thr Cys Lys Asn Ala Ser
        710                 715                 720 gtg gga gat aaa gtt ctc tac ggt ctc tat ggc ata gtg gaa cat agt    2266
Val Gly Asp Lys Val Leu Tyr Gly Leu Tyr Gly Ile Val Glu His Ser
    725                 730                 735 ggc tcg atg aga gaa ggc cac tac act gct tat gtg aaa gtg aga aca    2314
Gly Ser Met Arg Glu Gly His Tyr Thr Ala Tyr Val Lys Val Arg Thr
740                 745                 750                 755 ccc tcc agg aaa tta tcg gaa cat aac act aaa aag aaa aat gtg cct    2362
Pro Ser Arg Lys Leu Ser Glu His Asn Thr Lys Lys Lys Asn Val Pro
                760                 765                 770 ggt ttg aaa gcg gct gat agt gaa tca gca ggc cag tgg gtc cat gtt    2410
Gly Leu Lys Ala Ala Asp Ser Glu Ser Ala Gly Gln Trp Val His Val
            775                 780                 785 agt gac act tac tta cag gtg gtt cca gaa tca aga gca ctt agt gca    2458
Ser Asp Thr Tyr Leu Gln Val Val Pro Glu Ser Arg Ala Leu Ser Ala
        790                 795                 800 caa gcc tac ctt ctt ttc tat gaa aga gta tta taactattaa tggtaatgat    2511
Gln Ala Tyr Leu Leu Phe Tyr Glu Arg Val Leu
    805                 810 tatttaggtc atttgttttt gaatgccaca gtgataacta taatatataa tgtgcctttc    2571
tagtcttccc tcttctgtag gaatagcatg ttcctcaaat ggtcctgaac ttttcacca    2631 ttttggtgaa ccctttaaa gtaaatttac tcatgcttta aaattcatag tcttaaaata    2691
aatgtgaatt ttgtttccag gtatttattc tggggtacct gcccg                  2736
```

<210> SEQ ID NO 7
<211> LENGTH: 814
<212> TYPE: PRT
<213> ORGANISM: Homo sapiens

<400> SEQUENCE: 7

```
Met Arg Val Lys Asp Pro Thr Lys Ala Leu Pro Glu Lys Ala Lys Arg
 1               5                   10                  15

Ser Lys Arg Pro Thr Val Pro His Asp Glu Asp Ser Ser Asp Asp Ile
            20                  25                  30

Ala Val Gly Leu Thr Cys Gln His Val Ser His Ala Ile Ser Val Asn
        35                  40                  45

His Val Lys Arg Ala Ile Ala Glu Asn Leu Trp Ser Val Cys Ser Glu
    50                  55                  60

Cys Leu Lys Glu Arg Arg Phe Tyr Asp Gly Gln Leu Val Leu Thr Ser
```

```
65                  70                  75                  80
Asp Ile Trp Leu Cys Leu Lys Cys Gly Phe Gln Gly Cys Gly Lys Asn
                85                  90                  95
Ser Glu Ser Gln His Ser Leu Lys His Phe Lys Ser Ser Arg Thr Glu
            100                 105                 110
Pro His Cys Ile Ile Ile Asn Leu Ser Thr Trp Ile Ile Trp Cys Tyr
            115                 120                 125
Glu Cys Asp Glu Lys Leu Ser Thr His Cys Asn Lys Lys Val Leu Ala
        130                 135                 140
Gln Ile Val Asp Phe Leu Gln Lys His Ala Ser Lys Thr Gln Thr Ser
145                 150                 155                 160
Ala Phe Ser Arg Ile Met Lys Leu Cys Glu Glu Lys Cys Glu Thr Asp
                165                 170                 175
Glu Ile Gln Lys Gly Gly Lys Cys Arg Asn Leu Ser Val Arg Gly Ile
            180                 185                 190
Thr Asn Leu Gly Asn Thr Cys Phe Phe Asn Ala Val Met Gln Asn Leu
        195                 200                 205
Ala Gln Thr Tyr Thr Leu Thr Asp Leu Met Asn Glu Ile Lys Glu Ser
210                 215                 220
Ser Thr Lys Leu Lys Ile Phe Pro Ser Ser Asp Ser Gln Leu Asp Pro
225                 230                 235                 240
Leu Val Val Glu Leu Ser Arg Pro Gly Pro Leu Thr Ser Ala Leu Phe
                245                 250                 255
Leu Phe Leu His Ser Met Lys Glu Thr Glu Lys Gly Pro Leu Ser Pro
            260                 265                 270
Lys Val Leu Phe Asn Gln Leu Cys Gln Lys Ala Pro Arg Phe Lys Asp
            275                 280                 285
Phe Gln Gln Gln Asp Ser Gln Glu Leu Leu His Tyr Leu Leu Asp Ala
        290                 295                 300
Val Arg Thr Glu Glu Thr Lys Arg Ile Gln Ala Ser Ile Leu Lys Ala
305                 310                 315                 320
Phe Asn Asn Pro Thr Thr Lys Thr Ala Asp Asp Glu Thr Arg Lys Lys
                325                 330                 335
Val Lys Ala Tyr Gly Lys Glu Gly Val Lys Met Asn Phe Ile Asp Arg
            340                 345                 350
Ile Phe Ile Gly Glu Leu Thr Ser Thr Val Met Cys Glu Glu Cys Ala
        355                 360                 365
Asn Ile Ser Thr Val Lys Asp Pro Phe Ile Asp Ile Ser Leu Pro Ile
    370                 375                 380
Ile Glu Glu Arg Val Ser Lys Pro Leu Leu Trp Gly Arg Met Asn Lys
385                 390                 395                 400
Tyr Arg Ser Leu Arg Glu Thr Asp His Asp Arg Tyr Ser Gly Asn Val
                405                 410                 415
Thr Ile Glu Asn Ile His Gln Pro Arg Ala Ala Lys Lys His Ser Ser
            420                 425                 430
Ser Lys Asp Lys Arg Gln Leu Ile His Asp Arg Lys Cys Ile Arg Lys
        435                 440                 445
Leu Ser Ser Gly Glu Thr Val Thr Tyr Gln Lys Asn Glu Asn Leu Glu
    450                 455                 460
Met Asn Gly Asp Ser Leu Met Phe Ala Ser Leu Met Asn Ser Glu Ser
465                 470                 475                 480
Arg Leu Asn Glu Ser Pro Thr Asp Asp Ser Glu Lys Glu Ala Ser His
                485                 490                 495
```

-continued

```
Ser Glu Ser Asn Val Asp Ala Asp Ser Glu Pro Ser Glu Ser Glu Ser
            500                 505                 510

Ala Ser Lys Gln Thr Gly Leu Phe Arg Ser Ser Gly Ser Gly Val
        515                 520                 525

Gln Pro Asp Gly Pro Leu Tyr Pro Leu Ser Ala Gly Lys Leu Leu Tyr
        530                 535                 540

Thr Lys Glu Thr Asp Ser Gly Asp Lys Glu Met Ala Glu Ala Ile Ser
545                 550                 555                 560

Glu Leu Arg Leu Ser Ser Thr Val Thr Gly Asp Gln Asp Phe Asp Arg
                565                 570                 575

Glu Asn Gln Pro Leu Asn Ile Ser Asn Asn Leu Cys Phe Leu Glu Gly
            580                 585                 590

Lys His Leu Arg Ser Tyr Ser Pro Gln Asn Ala Phe Gln Thr Leu Ser
        595                 600                 605

Gln Ser Tyr Ile Thr Thr Ser Lys Glu Cys Ser Ile Gln Ser Cys Leu
    610                 615                 620

Tyr Gln Phe Thr Ser Met Glu Leu Leu Met Gly Asn Asn Lys Leu Leu
625                 630                 635                 640

Cys Glu Asn Cys Thr Lys Asn Lys Gln Lys Tyr Gln Glu Thr Ser
                645                 650                 655

Phe Ala Glu Lys Lys Val Glu Gly Val Tyr Thr Asn Ala Arg Lys Gln
            660                 665                 670

Leu Leu Ile Ser Ala Val Pro Ala Val Leu Ile Leu His Leu Lys Arg
        675                 680                 685

Phe His Gln Ala Gly Leu Ser Leu Arg Lys Val Asn Arg His Val Asp
    690                 695                 700

Phe Pro Leu Met Leu Asp Leu Ala Pro Phe Cys Ser Ala Thr Cys Lys
705                 710                 715                 720

Asn Ala Ser Val Gly Asp Lys Val Leu Tyr Gly Leu Tyr Gly Ile Val
                725                 730                 735

Glu His Ser Gly Ser Met Arg Glu Gly His Tyr Thr Ala Tyr Val Lys
            740                 745                 750

Val Arg Thr Pro Ser Arg Lys Leu Ser Glu His Asn Thr Lys Lys Lys
        755                 760                 765

Asn Val Pro Gly Leu Lys Ala Ala Asp Ser Glu Ser Ala Gly Gln Trp
    770                 775                 780

Val His Val Ser Asp Thr Tyr Leu Gln Val Val Pro Glu Ser Arg Ala
785                 790                 795                 800

Leu Ser Ala Gln Ala Tyr Leu Leu Phe Tyr Glu Arg Val Leu
                805                 810

<210> SEQ ID NO 8
<211> LENGTH: 2442
<212> TYPE: DNA
<213> ORGANISM: Homo sapiens
<220> FEATURE:
<221> NAME/KEY: CDS
<222> LOCATION: (1)...(2442)

<400> SEQUENCE: 8 atg cgg gtg aaa gat cca act aaa gct tta cct gag aaa gcc aaa aga      48
Met Arg Val Lys Asp Pro Thr Lys Ala Leu Pro Glu Lys Ala Lys Arg
  1               5                  10                  15 agt aaa agg cct act gta cct cat gat gaa gac tct tca gat gat att      96
Ser Lys Arg Pro Thr Val Pro His Asp Glu Asp Ser Ser Asp Asp Ile
             20                  25                  30
```

```
gct gta ggt tta act tgc caa cat gta agt cat gct atc agc gtg aat    144
Ala Val Gly Leu Thr Cys Gln His Val Ser His Ala Ile Ser Val Asn
         35                  40                  45 cat gta aag aga gca ata gct gag aat ctg tgg tca gtt tgc tca gaa    192
His Val Lys Arg Ala Ile Ala Glu Asn Leu Trp Ser Val Cys Ser Glu
 50                  55                  60 tgt tta aaa gaa aga aga ttc tat gat ggg cag cta gta ctt act tct    240
Cys Leu Lys Glu Arg Arg Phe Tyr Asp Gly Gln Leu Val Leu Thr Ser
 65                  70                  75                  80 gat att tgg ttg tgc ctc aag tgt ggc ttc cag gga tgt ggt aaa aac    288
Asp Ile Trp Leu Cys Leu Lys Cys Gly Phe Gln Gly Cys Gly Lys Asn
                 85                  90                  95 tca gaa agc caa cat tca ttg aag cac ttt aag agt tcc aga aca gag    336
Ser Glu Ser Gln His Ser Leu Lys His Phe Lys Ser Ser Arg Thr Glu
            100                 105                 110 ccc cat tgt att ata att aat ctg agc aca tgg att ata tgg tgt tat    384
Pro His Cys Ile Ile Ile Asn Leu Ser Thr Trp Ile Ile Trp Cys Tyr
        115                 120                 125 gaa tgt gat gaa aaa tta tca acg cat tgt aat aag aag gtt ttg gct    432
Glu Cys Asp Glu Lys Leu Ser Thr His Cys Asn Lys Lys Val Leu Ala
130                 135                 140 cag ata gtt gat ttt ctc cag aaa cat gct tct aaa aca caa aca agt    480
Gln Ile Val Asp Phe Leu Gln Lys His Ala Ser Lys Thr Gln Thr Ser
145                 150                 155                 160 gca ttt tct aga atc atg aaa ctt tgt gaa gaa aaa tgt gaa aca gat    528
Ala Phe Ser Arg Ile Met Lys Leu Cys Glu Glu Lys Cys Glu Thr Asp
                165                 170                 175 gaa ata cag aag gga gga aaa tgc aga aat tta tct gta aga gga att    576
Glu Ile Gln Lys Gly Gly Lys Cys Arg Asn Leu Ser Val Arg Gly Ile
            180                 185                 190 aca aat tta gga aat act tgc ttt ttt aat gca gtc atg cag aac ttg    624
Thr Asn Leu Gly Asn Thr Cys Phe Phe Asn Ala Val Met Gln Asn Leu
        195                 200                 205 gca cag act tat act ctt act gat ctg atg aat gag atc aaa gaa agt    672
Ala Gln Thr Tyr Thr Leu Thr Asp Leu Met Asn Glu Ile Lys Glu Ser
    210                 215                 220 agt aca aaa ctc aag att ttt cct tcc tca gac tct cag ctg gac cca    720
Ser Thr Lys Leu Lys Ile Phe Pro Ser Ser Asp Ser Gln Leu Asp Pro
225                 230                 235                 240 ttg gtg gtg gaa ctt tca agg cct gga cca ctg acc tca gcc ttg ttc    768
Leu Val Val Glu Leu Ser Arg Pro Gly Pro Leu Thr Ser Ala Leu Phe
                245                 250                 255 ctg ttt ctt cac agc atg aag gag act gaa aaa gga cca ctt tct cct    816
Leu Phe Leu His Ser Met Lys Glu Thr Glu Lys Gly Pro Leu Ser Pro
            260                 265                 270 aaa gtt ctt ttt aat cag ctt tgt cag aag gca cct cga ttt aaa gat    864
Lys Val Leu Phe Asn Gln Leu Cys Gln Lys Ala Pro Arg Phe Lys Asp
        275                 280                 285 ttc cag caa cag gac agt cag gag ctt ctt cat tat ctt ctg gat gca    912
Phe Gln Gln Gln Asp Ser Gln Glu Leu Leu His Tyr Leu Leu Asp Ala
    290                 295                 300 gtg agg aca gaa gaa aca aag cga ata caa gct agc att cta aaa gca    960
Val Arg Thr Glu Glu Thr Lys Arg Ile Gln Ala Ser Ile Leu Lys Ala
305                 310                 315                 320 ttt aac aac cca act act aaa act gct gat gat gaa act aga aaa aaa    1008
Phe Asn Asn Pro Thr Thr Lys Thr Ala Asp Asp Glu Thr Arg Lys Lys
                325                 330                 335 gtc aaa gca tat gga aaa gaa ggt gtg aaa atg aac ttc ata gat cgg    1056
Val Lys Ala Tyr Gly Lys Glu Gly Val Lys Met Asn Phe Ile Asp Arg
```

-continued

```
             340                 345                 350
atc ttt att ggt gaa tta act agc acg gtc atg tgt gaa gaa tgt gca     1104
Ile Phe Ile Gly Glu Leu Thr Ser Thr Val Met Cys Glu Glu Cys Ala
        355                 360                 365 aat atc tcc acg gtg aaa gat cca ttc att gat att tca ctt cct ata     1152
Asn Ile Ser Thr Val Lys Asp Pro Phe Ile Asp Ile Ser Leu Pro Ile
    370                 375                 380 ata gaa gaa agg gtt tca aaa cct tta ctt tgg gga aga atg aat aaa     1200
Ile Glu Glu Arg Val Ser Lys Pro Leu Leu Trp Gly Arg Met Asn Lys
385                 390                 395                 400 tat aga agt tta cgg gag aca gat cat gat cga tac agt ggc aat gtt     1248
Tyr Arg Ser Leu Arg Glu Thr Asp His Asp Arg Tyr Ser Gly Asn Val
                405                 410                 415 act ata gaa aat att cat caa cct aga gct gcc aag aag cat tct tca     1296
Thr Ile Glu Asn Ile His Gln Pro Arg Ala Ala Lys Lys His Ser Ser
            420                 425                 430 tct aaa gat aag aga caa cta att cat gac cga aaa tgt att aga aaa     1344
Ser Lys Asp Lys Arg Gln Leu Ile His Asp Arg Lys Cys Ile Arg Lys
        435                 440                 445 ttg tca tct gga gaa act gtc aca tac cag aaa aat gaa aac ctt gaa     1392
Leu Ser Ser Gly Glu Thr Val Thr Tyr Gln Lys Asn Glu Asn Leu Glu
    450                 455                 460 atg aat ggg gat tct tta atg ttt gcc agc ctc atg aat tct gag tca     1440
Met Asn Gly Asp Ser Leu Met Phe Ala Ser Leu Met Asn Ser Glu Ser
465                 470                 475                 480 cgt ctg aat gaa agc cct act gat gac agt gaa aaa gaa gcc agc cat     1488
Arg Leu Asn Glu Ser Pro Thr Asp Asp Ser Glu Lys Glu Ala Ser His
                485                 490                 495 tct gaa agc aat gtt gat gct gac agt gag cct tca gaa tct gaa agt     1536
Ser Glu Ser Asn Val Asp Ala Asp Ser Glu Pro Ser Glu Ser Glu Ser
            500                 505                 510 gct tca aag cag act ggg ctg ttc aga tcc agt agt gga tcc ggt gtg     1584
Ala Ser Lys Gln Thr Gly Leu Phe Arg Ser Ser Ser Gly Ser Gly Val
        515                 520                 525 cag cca gat gga ccc ctt tac cct ctg tca gca ggt aaa ctg ctg tac     1632
Gln Pro Asp Gly Pro Leu Tyr Pro Leu Ser Ala Gly Lys Leu Leu Tyr
    530                 535                 540 acc aag gag act gac agt ggt gat aag gaa atg gca gaa gct att tct     1680
Thr Lys Glu Thr Asp Ser Gly Asp Lys Glu Met Ala Glu Ala Ile Ser
545                 550                 555                 560 gaa ctt cgt ttg agc agc act gta act ggg gat caa gat ttt gac aga     1728
Glu Leu Arg Leu Ser Ser Thr Val Thr Gly Asp Gln Asp Phe Asp Arg
                565                 570                 575 gaa aat cag cca cta aat att tca aat aat tta tgt ttt tta gag ggg     1776
Glu Asn Gln Pro Leu Asn Ile Ser Asn Asn Leu Cys Phe Leu Glu Gly
            580                 585                 590 aag cat ttg agg tct tat agt ccc caa aat gct ttt cag acc ctt tct     1824
Lys His Leu Arg Ser Tyr Ser Pro Gln Asn Ala Phe Gln Thr Leu Ser
        595                 600                 605 cag agc tat ata act act tct aaa gaa tgt tca att cag tcc tgt ctc     1872
Gln Ser Tyr Ile Thr Thr Ser Lys Glu Cys Ser Ile Gln Ser Cys Leu
    610                 615                 620 tac cag ttt aca tct atg gaa tta cta atg ggg aat aat aag ctt cta     1920
Tyr Gln Phe Thr Ser Met Glu Leu Leu Met Gly Asn Asn Lys Leu Leu
625                 630                 635                 640 tgt gag aat tgt act aaa aac aaa cag aag tac caa gaa gaa acc agt     1968
Cys Glu Asn Cys Thr Lys Asn Lys Gln Lys Tyr Gln Glu Glu Thr Ser
                645                 650                 655 ttt gca gaa aag aaa gta gaa gga gtt tat act aat gcc agg aag caa     2016
```

```
Phe Ala Glu Lys Lys Val Glu Gly Val Tyr Thr Asn Ala Arg Lys Gln
            660                 665                 670 ttg ctc att tct gct gtt cca gct gtc cta att ctc cac ctg aaa aga      2064
Leu Leu Ile Ser Ala Val Pro Ala Val Leu Ile Leu His Leu Lys Arg
            675                 680                 685 ttt cat cag gct ggc ttg agt ctt cgt aaa gta aac aga cat gta gat      2112
Phe His Gln Ala Gly Leu Ser Leu Arg Lys Val Asn Arg His Val Asp
        690                 695                 700 ttt cca ctt atg ctc gat tta gca cca ttc tgc tct gct act tgt aag      2160
Phe Pro Leu Met Leu Asp Leu Ala Pro Phe Cys Ser Ala Thr Cys Lys
705                 710                 715                 720 aat gca agt gtg gga gat aaa gtt ctc tac ggt ctc tat ggc ata gtg      2208
Asn Ala Ser Val Gly Asp Lys Val Leu Tyr Gly Leu Tyr Gly Ile Val
                725                 730                 735 gaa cat agt ggc tcg atg aga gaa ggc cac tac act gct tat gtg aaa      2256
Glu His Ser Gly Ser Met Arg Glu Gly His Tyr Thr Ala Tyr Val Lys
            740                 745                 750 gtg aga aca ccc tcc agg aaa tta tcg gaa cat aac act aaa aag aaa      2304
Val Arg Thr Pro Ser Arg Lys Leu Ser Glu His Asn Thr Lys Lys Lys
            755                 760                 765 aat gtg cct ggt ttg aaa gcg gct gat agt gaa tca gca ggc cag tgg      2352
Asn Val Pro Gly Leu Lys Ala Ala Asp Ser Glu Ser Ala Gly Gln Trp
        770                 775                 780 gtc cat gtt agt gac act tac tta cag gtg gtt cca gaa tca aga gca      2400
Val His Val Ser Asp Thr Tyr Leu Gln Val Val Pro Glu Ser Arg Ala
785                 790                 795                 800 ctt agt gca caa gcc tac ctt ctt ttc tat gaa aga gta tta              2442
Leu Ser Ala Gln Ala Tyr Leu Leu Phe Tyr Glu Arg Val Leu
                805                 810
```

<210> SEQ ID NO 9
<211> LENGTH: 82
<212> TYPE: PRT
<213> ORGANISM: Artificial Sequence
<220> FEATURE:
<223> OTHER INFORMATION: Consensus

<400> SEQUENCE: 9

```
Cys Val Ser Thr Cys Gly Leu Thr Glu Asn Leu Trp Leu Cys Leu Thr
1               5                   10                  15

Cys Gly Gln Val Gly Cys Gly Arg Tyr Gln Tyr Asp Gly Asp Gly Gly
            20                  25                  30

Asn Gly His Ala Leu Glu His Tyr Glu Glu Thr Gly His Pro Leu Ala
        35                  40                  45

Val Lys Leu Lys Thr Gln Ser Val Trp Asp Tyr Ala Ala Asp Asn Tyr
    50                  55                  60

Val His Arg Glu Asp Ser Glu Asp Ala Leu Asp Gly Lys Tyr Leu
65                  70                  75                  80

Val Asp
```

<210> SEQ ID NO 10
<211> LENGTH: 16
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: The amino acid at position 2 can be I or V or
      M or F or Y
<220> FEATURE:
<221> NAME/KEY: VARIANT
<222> LOCATION: (6)...(6)

```
<223> OTHER INFORMATION: The amino acids from position 3 to 5 can be
      any amino acid
<220> FEATURE:
<221> NAME/KEY: VARIANT
<222> LOCATION: (7)...(7)
<223> OTHER INFORMATION: The amino acid at position 6 can be G or C
<223> OTHER INFORMATION: The amino acid at position 7 can be A or S or M
<220> FEATURE:
<221> NAME/KEY: VARIANT
<222> LOCATION: (10)...(10)
<223> OTHER INFORMATION: The amino acid at position 8 can be any amino
      acid
<220> FEATURE:
<221> NAME/KEY: VARIANT
<222> LOCATION: (11)...(11)
<223> OTHER INFORMATION: The amino acid at position 10 can be Y or W
<220> FEATURE:
<221> NAME/KEY: VARIANT
<222> LOCATION: (12)...(12)
<223> OTHER INFORMATION: The amino acid at position 11 can be I or V or
      M or F or C
<220> FEATURE:
<221> NAME/KEY: VARIANT
<222> LOCATION: (13)...(13)
<223> OTHER INFORMATION: The amino acid at position 12 can be S or T
<223> OTHER INFORMATION: The amino acid at position 13 can be A or C or
      V
<220> FEATURE:
<221> NAME/KEY: VARIANT
<222> LOCATION: (15)...(15)
<223> OTHER INFORMATION: The amino acid at position 14 can be any amino
      acid
<220> FEATURE:
<223> OTHER INFORMATION: The amino acid at position 15 can be I or V or
      M or S

<400> SEQUENCE: 10

Gly Leu Xaa Xaa Xaa Ala Asn Xaa Cys Phe Leu Asn Ser Xaa Leu Gln
 1               5                  10                  15

<210> SEQ ID NO 11
<211> LENGTH: 19
<212> TYPE: PRT
<213> ORGANISM: Artificial Sequence
<220> FEATURE:
<223> OTHER INFORMATION: Consensus
<223> OTHER INFORMATION: The amino acid at position 2 can be any amino
      acid
<220> FEATURE:
<221> NAME/KEY: VARIANT
<222> LOCATION: (5)...(5)
<223> OTHER INFORMATION: The amino acid at position 4 can be any amino
      acid
<220> FEATURE:
<221> NAME/KEY: VARIANT
<222> LOCATION: (6)...(6)
<223> OTHER INFORMATION: The amino acid at position 5 can be A or G
<223> OTHER INFORMATION: The amino acid at position 6 can be I or V or
      M or F or T
<223> OTHER INFORMATION: The amino acid at position 7 can be any amino
      acid
<223> OTHER INFORMATION: The amino acid at position 8 can be any amino
      acid
<223> OTHER INFORMATION: The amino acid at position 10 can be any amino
      acid
<223> OTHER INFORMATION: The amino acid at position 12 can be any amino
      acid
<223> OTHER INFORMATION: The amino acid at position 13 can be any amino
      acid
<223> OTHER INFORMATION: The amino acid at position 14 can be any amino
      acid
<223> OTHER INFORMATION: The amino acid at position 15 can be any amino
      acid
<220> FEATURE:
<223> OTHER INFORMATION: The amino acid at position 16 may or may not be
      present. It can be any amino acid
```

```
<400> SEQUENCE: 11

Tyr Xaa Leu Xaa Ser Leu Xaa Xaa His Xaa Gly Xaa Xaa Xaa Xaa
1               5                   10                  15

Gly His Tyr
```

US 6,911,335 B2

57316 AND 33338, HUMAN UBIQUITIN CARBOXYL TERMINAL HYDROLASES AND USES THEREFOR

CROSS-REFERENCES TO RELATED APPLICATIONS

This application claims the benefit of U.S. Provisional Application No. 60/276,395 filed Mar. 16, 2001, the contents of which are incorporated herein by this reference.

BACKGROUND OF THE INVENTION

Living cells are capable of modulating the levels of proteins that they express. A variety of different mechanisms exist through which protein levels can be modulated. The ubiquitin pathway is one example of a post-translational mechanism used to regulate protein levels. Ubiquitin is a highly conserved polypeptide expressed in all eukaryotic cells that marks proteins for degradation. Ubiquitin is attached as a single molecule or as a conjugated form to lysine residue(s) of proteins via formation of an isopeptide bond at the C-terminal glycine residue. Most ubiquitinated proteins are subsequently targeted to the 26S proteasome, a multicatalytic protease, which cleaves the marked protein into peptide fragments.

Only the protein conjugated to ubiquitin is degraded via the proteasome; ubiquitin itself is recycled by ubiquitin carboxy-terminal hydrolases (UCH; sometimes abbreviated UCTH), which cleave the bond between ubiquitin and the protein targeted for degradation. These enzymes constitute a family of thiol proteases, and homologues have been found in, for example, yeast (Miller et al., *BioTechnology* 7:698–704, 1989; Tobias and Varshavsky, *J. Biol. Chem.* 266:12021–12028, 1991; Baker et al., *J. Biol. Chem.* 267:23364–23375, 1992), bovine (Papa and Hochstrasser, *Nature* 366:313–319, 1993), avian (Woo et al., *J. Biol. Chem.* 270:18766–18773, 1995), *Drosophila* (Zhang et al., *Dev. Biol.* 17:214, 1993) and human (Wilkinson et al., *Science* 246:670, 1989) cells.

Ubiquitination has been implicated in regulating numerous cellular processes including, for example, proliferation, differentiation, apoptosis (programmed cell death), transcription, signal-transduction, cell-cycle progression, receptor-mediated endocytosis, organelle biogenesis and others. The presence of abnormal amounts of ubiquitinated proteins in neuropathological conditions such as Alzheimer's and Pick's disease indicates that ubiquitination plays a role in various physiological disorders. Oncogenes (e.g., v-jun and v-fos) are often found to be resistant to ubiquitination in comparison to their normal cell counterparts, suggesting that a failure to degrade oncogene protein products accounts for some of their cell transformation capability. Combined with the observation that not all ubiquitinated proteins are degraded by the proteasome, these findings indicate that the process of ubiquitination and de-ubiquitination of particular substrates have important functional roles apart from recycling ubiquitin.

SUMMARY OF THE INVENTION

The present invention is based, in part, on the discovery of novel genes encoding ubiquitin carboxyl terminal hydrolase proteins, the genes being referred to herein as "57316 or 33338". The nucleotide sequence of the cDNA encoding 57316 or 33338 are shown in SEQ ID NO:1 and SEQ ID NO:6 respectively, and the amino acid sequence of the 57316 and 33338 polypeptide is shown in SEQ ID NO:2 and SEQ ID NO:7, respectively. In addition, the nucleotide sequence of the coding regions are depicted in SEQ ID NO:3 and SEQ ID NO:7, respectively.

Accordingly, in one aspect, the invention features a nucleic acid molecule that encodes a 57316 or 33338 protein or polypeptide, e.g., a biologically active portion of the 57316 or 33338 protein. In a preferred embodiment the isolated nucleic acid molecule encodes a polypeptide having the amino acid sequence SEQ ID NO:2 and SEQ ID NO:7. In other embodiments, the invention provides isolated 57316 or 33338 nucleic acid molecules having the nucleotide sequence of one of SEQ ID NO:1, SEQ ID NO:3, or SEQ ID NO:6, and SEQ ID NO:8.

In still other embodiments, the invention provides nucleic acid molecules that have sequences that are sufficiently or substantially identical (e.g., naturally occurring allelic variants) to the nucleotide sequence of one of SEQ ID NO:1, SEQ ID NO:3, or SEQ ID NO:6, SEQ ID NO:8, and the deposited nucleotide sequence. In other embodiments, the invention provides a nucleic acid molecule which hybridizes under stringent hybridization conditions with a nucleic acid molecule having a sequence comprising the nucleotide sequence of one of SEQ ID NO:1, SEQ ID NO:3, or SEQ ID NO:6:, SEQ ID NO:8 and the deposited nucleotide sequence, wherein the nucleic acid encodes a full length 57316 or 33338 protein or an active fragment thereof.

In a related aspect, the invention further provides nucleic acid constructs that include a 57316 or 33338 nucleic acid molecule described herein. In certain embodiments, the nucleic acid molecules of the invention are operatively linked to native or heterologous regulatory sequences. Also included are vectors and host cells containing the 57316 or 33338 nucleic acid molecules of the invention, e.g., vectors and host cells suitable for producing 57316 or 33338 polypeptides.

In another related aspect, the invention provides nucleic acid fragments suitable as primers or hybridization probes for detection of 57316 or 33338-encoding nucleic acids.

In still another related aspect, isolated nucleic acid molecules that are antisense to a 57316 or 33338-encoding nucleic acid molecule are provided.

In another aspect, the invention features 57316 or 33338 polypeptides, and biologically active or antigenic fragments thereof that are useful, e.g., as reagents or targets in assays applicable to treatment and diagnosis of 57316 or 33338-mediated or related disorders (e.g., ubiquitin carboxyl terminal hydrolase-mediated disorders such as those described herein). In another embodiment, the invention provides 57316 or 33338 polypeptides having ubiquitin carboxyl terminal hydrolase activity. Preferred polypeptides are 57316 or 33338 proteins including at least one ubiquitin carboxyl terminal hydrolase domain, and preferably having a 57316 or 33338 activity, e.g., a 57316 or 33338 activity as described herein. Preferred polypeptides are 57316 or 33338 proteins including at least one zinc-fingers in ubiquitin hydrolases domain, at least one ubiquitin carboxyl terminal hydrolase-1 domain and at least one ubiquitin carboxyl terminal hydrolase-2 domain.

In other embodiments, the invention provides 57316 or 33338 polypeptides, e.g., a 57316 or 33338 polypeptide having the amino acid sequence shown in SEQ ID NO:2 and SEQ NO:7; an amino acid sequence that is substantially identical to the amino acid sequence shown in SEQ ID NO:2 and SEQ ID NO:7; or an amino acid sequence encoded by a nucleic acid molecule having a nucleotide sequence which hybridizes under stringent hybridization conditions to a nucleic acid molecule comprising the nucleotide sequence of any of SEQ ID NO:1, SEQ ID NO:3 or SEQ ID:NO:6, SEQ ID:NO:8, and the deposited nucleotide sequence, wherein the nucleic acid encodes a full length 57316 or 33338 protein or an active fragment thereof.

In a related aspect, the invention further provides nucleic acid constructs that include a 57316 or 33338 nucleic acid molecule described herein.

In a related aspect, the invention provides 57316 or 33338 polypeptides or fragments operatively linked to non-57316 or 33338 polypeptides to form fusion proteins.

In another aspect, the invention features antibodies and antigen-binding fragments thereof, that react with, or more preferably, specifically or selectively bind, 57316 or 33338 polypeptides.

In another aspect, the invention provides methods of screening for compounds that modulate the expression or activity of the 57316 or 33338 polypeptides or nucleic acids.

In still another aspect, the invention provides a process for modulating 57316 or 33338 polypeptide or nucleic acid expression or activity, e.g., using the compounds identified in the screens. In certain embodiments, the methods involve treatment of conditions related to aberrant activity or expression of the 57316 or 33338 polypeptides or nucleic acids, such as conditions involving aberrant or deficient activity of ubiquitin, or other stress proteins that target the degradation of abnormal proteins characteristic of human neurodegenerative disease (Lowe et. al., (1990) *J. Pathology* 161(2): 153–60).

The invention also provides assays for determining the activity of or the presence or absence of 57316 or 33338 polypeptides or nucleic acid molecules in a biological sample, including for disease diagnosis.

In a further aspect the invention provides assays for determining the presence or absence of a genetic alteration in a 57316 or 33338 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 57316 and 33338 molecule. In one embodiment, the capture probe is a nucleic acid, e.g., a probe complementary to a 57316 and 33338 nucleic acid sequence. In another embodiment, the capture probe is a polypeptide, e.g., an antibody specific for 57316 and 33338 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIG. 1 depicts hydropathy plots of human 57316 and 33338 Relatively hydrophobic residues are shown above the dashed horizontal line, and relatively hydrophilic residues are below the dashed horizontal line. The cysteine residues (cys) are indicated by short vertical lines below the hydropathy trace. The numbers corresponding to the amino acid sequence of human 57316 and human 33338 are indicated on the x axis.

DETAILED DESCRIPTION OF THE INVENTION

A human 57316 cDNA sequence (SEQ ID NO:1), which is approximately 4541 a nucleotide residues long including un-translated regions, contains a predicted methionine-initiated coding sequence of about 4059 nucleotide residues, excluding termination codon (i.e., nucleotide residues 192–4250 of SEQ ID NO:1 (also shown in SEQ ID NO:3). The coding sequence encodes a 1354 amino acid protein having the amino acid sequence of SEQ ID NO:2.

The human 33338 cDNA sequence (SEQ ID NO:6), which is approximately 2736 nucleotide residues long including un-translated regions, contains a predicted methionine-initiated coding sequence of about 2442 nucleotide residues, excluding termination codon (i.e., nucleotide residues 50–2491 of SEQ ID NO:6 (also shown in SEQ ID NO:8). The coding sequence encodes a 815 amino acid protein having the amino acid sequence of SEQ ID NO:7.

The 57316 or 33338 protein contains a significant number of structural characteristics in common with members of the ubiquitin carboxyl terminal hydrolase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., ubiquitin carboxyl terminal hydrolase proteins for any species described in the art (e.g., Miller et al., supra, and references cited therein). Members of a family can also have common functional characteristics.

Members of the ubiquitin carboxyl terminal hydrolase family have the ability to cleave the bond between ubiquitin and a protein targeted for degradation. As the 57316 and 33338 protein have significant identity to ubiquitin carboxyl-terminal hydrolase proteins, 57316 and 33338 are also likely ubiquitin carboxyl terminal hydrolases. Ubiquitin carboxyl terminal hydrolases are important in modulating ubiquitination of proteins which are important in regulating numerous cellular processes including, for example, proliferation, differentiation, apoptosis (programmed cell death), transcription, signal-transduction, cell-cycle progression, receptor-mediated endocytosis, organelle biogenesis and others.

Members of the ubiquitin carboxyl-terminal hydrolase family play an important role in modulating ubiquitinated proteins. Ubiquitinated proteins are found in, for example, filamentous inclusions found in neurons in the major human neurodegenerative diseases, i.e., Alzheimer's disease, diffuse Lewy body disease, and motor neuron disease. Lowe et al., (1990) *J Pathol* 161(2):153–60.

A 57316 or 33338 polypeptide can include various domains or regions common to the family of ubiquitin carboxyl terminal hydrolase. Members of the ubiquitin carboxyl-terminal hydrolase family of proteins are characterized by "ubiquitin carboxyl-terminal hydrolase domains." As used herein, the term "ubiquitin carboxyl-terminal hydrolase domain" refers to an amino acid sequence that participates in the removal of one or more ubiquitin molecules from a protein that has one or more molecules of ubiquitin attached to it. The definition also includes cleavage of conjugated forms of ubiquitin (e.g., in a head to tail orientation linked via a peptide bond) whether or not the ubiquitin conjugate is attached to a protein. For example, a ubiquitin-ubiquitin conjugate (dimer) could be cleaved into monomers, a tri-ubiquitin conjugate could be cleaved into three monomers, or a dimer and a single monomer. In either of these particular examples, the monomer or dimer could remain attached to or be cleaved from the ubiquitinated protein. In addition, the zinc fingers in ubiquitin-hydrolases domain displays some similarities with the Zn binding domain of the insulinase family. It is found only in a small subfamily of ubiquitin C-terminal hydrolases (deubiquitinases). All members of this subfamily are isopeptidase-T that are known to cleave isopeptide bonds between ubiquitin moieties.

A ubiquitin carboxyl terminal hydrolase protein typically has at least two catalytic domains, refered to as ubiquitin carboxyl terminal hydrolase-1, and ubiquitin carboxyl terminal hydrolase-2. For example, a human 57316 or 33338 can include a ubiquitin carboxyl terminal hydrolase-1 domain. As used herein, the term "ubiquitin carboxyl terminal hydrolase-1 domain" refers to a 57316 protein domain having an amino acid sequence of about 5–60 amino acid residues in length, preferably about 10–50 amino acid residues, more preferably about 20–40 amino acid residues, and even more preferably about 30–35 amino acids, and has a bit score for the alignment of the sequence to the ubiquitin carboxyl terminal hydrolase domain-1 (HMM) of at least about 5, preferably about 10, or more preferably about 15 or greater, and an E-value of about 0.2 or less, more preferably about 0.02 or less, and most preferably about 0.002 or less.

As used herein, the term "ubiquitin carboxyl terminal hydrolase-1 domain" refers to a 33338 protein domain having an amino acid sequence of about 5–60 amino acid residues in length, preferably about 10–50 amino acid residues, more preferably about 20–40 amino acid residues, and even more preferably about 30–35 amino acids, and has a bit score for the alignment of the sequence to the ubiquitin carboxyl terminal hydrolase domain-1 (HMM) of at least about 20, preferably about 30, or more preferably about 40 or greater, and an E-value of about 4.9e–5 or less, more preferably about 4.9e–6 or less, and most preferably about 4.9e–7 or less.

The ubiquitin carboxyl terminal hydrolase-1 domain has been assigned the PFAM accession number PF00442. (http://genome.wustl.edu/Pfam/html). Alignments of portions of the 57316 and 33338 protein with a consensus ubiquitin carboxyl terminal hydrolase-1 amino acid sequence (SEQ ID NO:4 and SEQ ID NO:10 respectively) derived from a hidden Markov model in Pfam show that the ubiquitin carboxyl terminal hydrolase-1 domain of the 57316 and 33338 proteins have bit scores of about 16.6 and 40.1 respectively, and E values of 0.002 and 4.9e–08 respectively.

The ubiquitin carboxyl-terminal hydrolase-1 (UCH-1) domain of the 57316 and 33338 protein contains a conserved signature pattern as follows: G-[LIVMFY]-x(1,3)-[AGC]-[NASM]-x-C-[FYW]-[LIVMFC]-[NST]-[SACV]-x-[LIVMS]-Q (PROSITE pattern PDOC00750 available from the ExPASy (Expert Protein Analysis System) proteomics server of the Swiss Institute of Bioinformatics (SIB), Geneva, Switzerland) (SEQ ID NO:10), or an amino acid signature pattern similar to the UCH-1 signature pattern above.

In consensus sequence patterns described in this application, each element in the pattern is separated by a dash (–); square [ ] brackets indicate the particular residues that are accepted at that position; elaborate { } brackets indicate the residues that are not accepted at that position; x indicates any residue is accepted at that position; a whole number in parenthesis following an x indicates any amino acid repetition of a particular element is accepted for that specified number of residues i.e. x(4).

The 57316 protein contains an amino acid signature pattern similar to the UCH-1 conserved signature pattern above, except that it differs at amino acid residues 183 and 184 of SEQ ID NO:2, wherein a "C" is substituted for any of the "LIVMS" residues at amino acid residue 183 of SEQ ID NO:2, and a "K" is substituted for a "Q" at amino acid residue 184 of SEQ ID NO:2.

The 33338 protein does include the UCH-1 conserved signature pattern described above at about amino acid residues 191 to 206 of SEQ ID NO:7

In a preferred embodiment, a 57316 or 33338 polypeptide or protein has a ubiquitin carboxyl terminal hydrolase-1 domain or a region which includes at least about 5–60, more preferably about 10–50, 20–40, or 30–35 amino acid residues and has at least about 60%, 70%, 80%, 90%, 95%, 99%, or 100% identity with a ubiquitin carboxyl terminal hydrolase-1 domain, e.g., the ubiquitin carboxyl-terminal hydrolase-1-like domain of human 57316 (e.g., residues 168 to 198 of SEQ ID NO:2, and the ubiquitin carboxyl-terminal hydrolase-1 domain of human 33338 (e.g., residues 190 to 221 of SEQ ID NO:7 respectively).

To identify the presence of an ubiquitin carboxyl terminal hydrolase-1 domain profile in a 57316 or 33338 molecule, the amino acid sequence of the protein is searched against a database of HMMs (e.g., the Pfam database, release 2.1) using the default parameters see the Pfam website maintained in several locations, e g. by the Sanger Institute (pfam.sanger.ac,uk/Software/Pfam/HMM search). For example, the hmmsf program, which is available as part of the HMMER package of search programs, is a family specific default program for MILPAT0063 and score of 15 is the default threshold score for determining a hit.

A human 57316 or 33338 polypeptide can also contain one or more ubiquitin carboxyl-terminal hydrolase-2 domains or regions. As used herein, the term "ubiquitin carboxyl-terminal hydrolase-2 domain" refers to a protein domain of the human 57316 having an amino acid sequence of about 50–120 amino acid residues in length, preferably about 60–110 amino acid residues, more preferably about 70–100 amino acid residues, and even more preferably about 80–90 amino acid residues, and has a bit score for the alignment of the sequence to the ubiquitin carboxyl-terminal hydrolase-2 domain (HMM) of at least about 60, preferably about 70, or or more preferably about 80 or greater and an E-value of about 7.6e–22 or less, more preferably about 7.6e–23 or less, and most preferably about 7.6e–23 or less. The ubiquitin carboxyl-terminal hydrolase-2 domain has been assigned the PFAM accession number PF00443. (http://genome.wustl.edu/Pfam/html). Alignments of portions of the 57316 and 33338 proteins with a consensus ubiquitin carboxyl-terminal hydrolase-2 amino acid sequence (SEQ ID NO:5, and SEQ ID NO:11, respectively) derived from a hidden Markov model in Pfam show that the ubiquitin carboxyl-terminal hydrolase-2 domains of 57316 and 33338 have bit scores of about 96.0 and 65.8, and an E-value of about 7.6 e–25 and 9.6e–16, respectively.

As used herein, the term "ubiquitin carboxyl-terminal hydrolase-2 domain" refers to a protein domain of the human 33338 protein having an amino acid sequence of about 50–120 amino acid residues in length, preferably about 60–110 amino acid residues, more preferably about 70–100 amino acid residues, and even more preferably about 80–90 amino acids, and has a bit score for the alignment of the sequence to the ubiquitin carboxyl-terminal hydrolase-2 domain (HMM) of at least about 40, preferably about 50, or or more preferably about 60 or greater and an E-value of about 9–13 or less, more preferably about 9e–14 or less, and most preferably about 9e–15 or less. The ubiquitin carboxyl-terminal hydrolase-2 domain has been assigned the PFAM accession number PF00443. (http://genome.wustl.edu/Pfam/html).

The ubiquitin carboxyl-terminal hydrolase-2 (UCH-2) domain contains a conserved signature pattern as follows: Y-x-L-x-[SAG]-[LIVMFT]-x(2)-H-x-G-x(4,5)-G-H-Y (PROSITE pattern PDOC00750 available from the ExPASy (Expert Protein Analysis System) proteomics server of the Swiss Institute of Bioinformatics (SIB), Geneva, Switzerland) (SEQ ID NO:11).

The 57316 protein contains a UCH-2 conserved signature pattern at about amino acid residues 465 to 482 of SEQ ID NO:2.

The 33338 protein also contains a UCH-2 conserved signature pattern at about amino acid residues 730 to 747 of SEQ ID NO:7.

In a preferred embodiment, a 57316 or 33338 polypeptide or protein has a ubiquitin carboxyl-terminal hydrolase-2 domain or a region which includes at least about 50–120, more preferably about 60–110, 70–100, or 80–90 amino acid residues and has at least about 60%, 70%, 80%, 90%, 95%, 99%, or 100% identity with a ubiquitin carboxyl-terminal hydrolase-2 domain, e.g., the ubiquitin carboxyl-terminal hydrolase-2 domain of human 57316 or 33338 (e.g., residues 461 to 541 of SEQ ID NO:2, and residues 726to 812 of SEQ ID NO:7 respectively). To identify the presence of an ubiquitin carboxyl-terminal hydrolase-2 domain profile in a 57316 or 33338 molecule, the amino acid sequence of the protein is searched against a database of HMMs (e.g., the Pfam database, release 2.1) using the default parameters see the Pfam website maintained in several locations, e.g. by the Sanger Institute (pfam.sanger.ac.uk/Software/Pfam/HMM search). For example, the hmmsf program, which is available as part of the HMMER package of search programs, is a family specific default program for MILPAT0063 and score of 15 is the default threshold score for determining a hit.

A human 33338 polypeptide of the invention can also contain one or more zinc fingers in ubiquitin-hydrolase domains or regions. As used herein, the term "zinc fingers in ubiquitin-hydrolase domain" refers to a protein domain having an amino acid sequence of 40–140 amino acid residues in length, preferably about 60–120 amino acid residues, more preferably about 80–100 amino acid residues, and even more preferably about 85–90 amino acid residues, and has a bit score for the alignment of the sequence to the zinc fingers in ubiquitin-hydrolase-like domain (HMM) of at least about 10, preferably about 20, or or more preferably about 30 or greater and an E-value of about 4.3e–4 or less, more preferably about 4.3e–5 or less, and most preferably about 4.3e–6 or less. The zinc fingers in ubiquitin-hydrolase domain has been assigned the PFAM accession number PF02148. (http://genome.wustl.edu/Pfam/html). An alignment of the 33338 protein with a consensus zinc fingers in ubiquitin-hydrolase amino acid sequence (SEQ ID NO:9) derived from a hidden Markov model in Pfam shows that the zinc fingers in ubiquitin-hydrolase domain of 33338 has a bit score of about 30.3, and an E-value of about 4.3e–7.

In a preferred embodiment, a 33338 polypeptide or protein has a zinc fingers in ubiquitin-hydrolase domain or a region which includes at least about 40–140, more preferably about 60–120: 80–100, or 85–90 amino acid residues and has at least about 60%, 70%, 80%, 90% 95%, 99%, or 100% identity with a zinc fingers in ubiquitin-hydrolase domain, e.g., the zinc fingers in ubiquitin-hydrolase domain of human 33338 (e.g., residues 62 to 148 of SEQ ID NO:7). To identify the presence of a zinc fingers in ubiquitin-hydrolase domain profile in a 33338 molecule, the amino acid sequence of the protein is searched against a database of HMMs (e.g., the Pfam database, release 2.1) using the default parameters see the Pfam website maintained in several locations, e.g. by the Sanger Institute (pfam.sanger.ac.uk/Software/Pfam/HMM search). For example, the hmmsf program, which is available as part of the HMMER package of search programs, is a family specific default program for MLLPAT0063 and score of 15 is the default threshold score for determining a hit.

The 57316 protein has 5 predicted N-glycosylation sites (Prosite Pattern Number PS00001) at about amino acid residues 65–68, 161–164, 717–720, 1076–1079, and 1179–1182, of SEQ ID NO:2; one predicted glycosaminoglycan attachment sites (Prosite Pattern Number PS00002) at about amino acid residues 1023–1026 of SEQ ID NO:2; four predicted cAMP and cGMP dependent protein kinase phosphorylation sites (Prosite Pattern Number PS00004) at about amino acid residues 980–983, 1036–1039, 1157–1160, and 1315–1318, of SEQ ID NO:2; twenty seven predicted protein kinase C phosphorylation sites (Prosite Pattern Number PS00005) at about amino acid residues 88–90, 108–110, 223–225, 450–452, 584–586, 611–613, 677–679, 686–688, 711–713, 737–739, 755–757, 758–760, 767–769, 799–801, 815–817, 843–845, 855–857, 874–876, 970–972, 1000–1002, 1072–1074, 1089–1091, 1129–1131, 1160–1162, 1207–1209, 1318–1320, and 1331–1333, of SEQ ID NO:2; thirty five casein kinase II phosphorylation sites (Prosite Pattern Number PS00006) located at about amino acid residues 35–38, 91–94, 108–111, 123–126, 128–131, 145–148, 203–206, 301–304, 320–323, 388–391, 397–400, 411–414, 45–418, 433–436, 448–451, 456–459, 488–491, 496–499, 506–509, 611–614, 719–722, 881–884, 911–914, 922–925, 933–936, 986–989, 991–994, 995–998, 1003–1006, 1066–1069, 1081–1084, 1133–1136, 1228–1231, and 1262–1265 of SEQ ID NO:2; eight predicted tyrosine kinase phosphorylation sites (Prosite Pattern Number PS00007) located at about amino acid residues 288–294, 369–375, 487–495, 549–556, 613–620, 638–645, 739–746, and 1002–1009 of SEQ ID NO:2; fifteen predicted N-myristoylation sites (Prosite Pattern Number PS00008) at about amino acid residues 73–78, 141–146, 313–318, 421–426, 437–442, 457–462, 475–480, 515–520, 659–664, 824–829, 842–847, 1022–1027, 1052–1057, 1146–1151, and 1255–1260 of SEQ ID NO:2; two predicted amidation sites (Prosite Pattern Number PS00009) at about amino acid residues 99–101 and 978–981 of SEQ ID NO:2; and one ubiquitin carboxyl terminal hydrolases family 2 signature 2 sites (Prosite Pattern Number PS00973 at about amino acid residues 465–482 of SEQ ID NO:2.

The 33338 protein has seven predicted N-glycosylation sites (Prosite Pattern Number PS00001) at about amino acid residues 119–122, 186–189, 369–372, 415–418, 582–585, 643–646, and 721–724 of SEQ ID NO:7; one predicted glycosaminoglycan attachment site (Prosite Pattern Number PS00002) at about amino acid residues 524–527 of SEQ ID NO:7; four predicted cAMP and cGMP dependent protein kinase phosphorylation sites (Prosite Pattern Number PS00004) at about amino acid residues 18–21, 428–431, 447–450, and 758–761 of SEQ ID NO:7; twenty one predicted protein kinase C phosphorylation sites (Prosite Pattern Number PS00005) at about amino acid residues 17–19, 102–104, 108–110, 188–190, 225–227, 261–263, 265–267, 271–273, 310–312, 325–327, 333–335, 372–374, 403–405, 432–434, 490–492, 614–616, 695–697, 718–720, 741–743, 757–759, and 765–767 of SEQ ID NO:7; twenty one casein kinase II phosphorylation sites (Prosite Pattern Number PS00006) located at about amino acid residues 28–31, 109–112, 213–216, 236–239, 261–264, 328–331, 372–375, 403–406, 407–410, 432–435, 450–453, 485–488, 490–493, 495–498, 499–502, 508–511, 614–617, 628–631, 656–659, 723–726, and 741–744 of SEQ ID NO:7; two predicted tyrosine kinase phosphorylation sites (Prosite Pattern Number PS00007) located at about amino acid residues 405–412, and 660–666 of SEQ ID NO:7; five predicted N-myristoylation sites (Prosite Pattern Number PS00008) at about amino acid residues 92–97, 344–349, 518–523, 664–669, and 772–777 of SEQ ID NO:7; and one ubiquitin carboxyl terminal hydrolases family 2 signature 2 sites (Prosite Pattern Number PS00973 at about amino acid residues 730–747 of SEQ ID NO:7.

General information regarding PFAM identifiers, PS prefix and PF prefix domain identification numbers can be found at Sonnhammer et al. (1997) *Protein* 28:405–420 or the Pfam website maintained in several locations, e.g. by the Sanger Institute (pfam.sanger.ac.uk), Washington University (pfam.wustl.edu), the Karolinska Institute (pfam.cgr.kr.se) or Institut de ta National Recherche Agronomique (pfam.jouy.inra.fr)).

In one embodiment of the invention, a 57316 or 33338 polypeptide includes at least one ubiquitin carboxyl terminal hydrolase-1 domain.

In another embodiment of the invention, a 57316 or 33338 polypeptide includes at least one ubiquitin carboxyl terminal hydrolase-2 domain.

In yet another embodiment of the invention, a 33338 polypeptide includes at least one zinc fingers in ubiquitin hydrolases domain.

In still another embodiment, the 57316 and 33338 polypeptide includes at least one ubiquitin carboxyl terminal hydrolase-1 domain and at least one ubiquitin carboxyl-terminal hydrolase-2 domain.

In a further embodiment, the 33338 polypeptide includes at least one ubiquitin carboxyl terminal hydrolase-1 domain, at least one ubiquitin carboxyl-terminal hydrolase-2 domain, and at least one zinc fingers in ubiquitin hydrolases domain.

The 57316 or 33338 molecules of the present invention can further include one or more of the N-glycosylation, glycosaminoglycan attachment sites, cAMP and cGMP dependent protein kinase phophorylation, protein kinase C phosphorylation, casein kinase II phosphorylation, tyrosine kinase phophorylation sites, N-myristoylation, amidation, and ubiquitin carboxyl-terminal hydrolases family 2 signature 2 sites described herein.

As the 57316 or 33338 polypeptides of the invention can modulate 57316 or 33338 activities, they can be used to develop novel diagnostic and therapeutic agents for 57316 or 33338-mediated or related disorders, as described herein.

As used herein, a "57316 or 33338 activity", "biological activity of 57316 or 33338" or "functional activity of 57316 or 33338", refers to an activity exerted by a 57316 or 33338 protein, polypeptide or nucleic acid molecule on e.g., a 57316 or 33338-responsive cell or on a 57316 or 33338 substrate, e.g., a protein substrate such as a ubiquitinated protein, as determined in vivo or in vitro. In one embodiment, a 57316 or 33338 activity is a direct activity, such as an association with a 57316 or 33338 target molecule. A "target molecule" or "binding partner" is a molecule with which a 57316 or 33338 protein binds or interacts in nature, e.g., a complex of ubiquitin and a protein targeted for degradation. A 57316 or 33338 activity can also be an indirect activity, e.g., an activity mediated by a protein that is a target for de-ubiquitination by 57316 or 33338.

For example, the 57316 or 33338 proteins of the present invention can modulate (directly or indirectly) any one or more of the following functions: (1) de-ubiquitination of a substrate, e.g., a ubiquitinated protein targeted for degradation; (2) the processing of poly-ubiquitin precursors; (3) cellular proliferation and/or differentiation; (4) apoptosis; (5) transcription and/or cell-cycle progression; (6) signal-transduction; (7) antigen processing; (8) cell-cell adhesion; (9 receptor-mediated endocytosis; (10) organelle biogenesis and development; (11) neuropathological conditions; (12) oncogenesis, and (13) protein levels, e.g., cellular protein levels.

Other activities, as described herein, include the ability to modulate function, survival, morphology, proliferation and/or differentiation of cells of tissues in which 57316 or 33338 molecules are expressed. Thus, the 57316 or 33338 molecules can act as novel diagnostic targets and therapeutic agents for controlling disorders involving aberrant activities of these cells.

The 57316 or 33338 molecules find use in modulating ubiquitin carboxyl terminal hydrolase function, activity, or expression, or related responses to ubiquitin carboxyl terminal hydrolase function, activity or expression. As used herein, the term "modulate" or grammatical variations thereof means increasing or decreasing an activity, function, signal or response. That is, the 57316 or 33338 molecules of the invention affect the targeted activity in either a positive or negative fashion (e.g., increase or decrease activity, function, or signal). Accordingly, the 57316 or 33338 molecules can act as novel diagnostic targets and therapeutic agents for controlling ubiquitin carboxyl terminal hydrolase-associated disorders.

Thus, 57316 or 33338 molecules described herein can act as novel diagnostic targets and therapeutic agents for prognosticating, modulating, diagnosing, preventing, inhibiting, alleviating, or treating ubiquitin carboxyl terminal hydrolase-associated disorders.

As used herein, a "ubiquitin carboxyl terminal hydrolase-associated disorder" includes a disorder, disease or condition which is characterized by a misregulation of a ubiquitin carboxyl terminal hydrolase mediated-activity or by an abnormal ubiquitin carboxyl terminal hydrolase-mediated activity. The 57316 or 33338 molecules can act as novel diagnostic targets and therapeutic agents for controlling activities associated with aberrant degradation of neuropeptides such as learning and memory processes, grooming, stress, depression, stretching and yawning, social, sexual and rewarded behavior, neuronal death, aging, nerve regeneration, thermoregulation, pain, sensitivity to seizures, cardiovascular control, memory disturbances and schizophrenia.

The 57316 or 33338 molecules also find use in diagnosis of disorders involving an increase or decrease in 57316 or 33338 ubiquitin carboxyl terminal hydrolase expression relative to normal expression, such as a proliferative disorder, a differentiative disorder (e.g., cancer), cardiovascular disorders, reproduction, regulating blood pressure, endothelial function, and natriuresis.

Thus, where expression or activity of 57316 or 33338 ubiquitin carboxyl terminal hydrolase is greater or less than normal, this may indicate the presence of or a predisposition towards a 57316 or 33338 ubiquitin carboxyl terminal hydrolase associated disorder. The presence of 57316 or 33338 ubiquitin carboxyl terminal hydrolase RNA or protein, e.g., by hybridization of a 57316 or 33338 specific probe or with a 57316 or 33338 specific antibody, can be used to identify the amount of 57316 or 33338 present in a particular cell or tissue, or other biological sample. 57316 or 33338 activity (proliferation, differentiation, apoptosis (programmed cell death assays, etc.)) can be assessed using the various techniques described herein or otherwise known in the art. Thus, in another embodiment, the invention provides methods and compositions for detection of 57316 or 33338 ubiquitin carboxyl terminal hydrolase in tissues that normally or do not normally express 57316 or 33338 ubiquitin carboxyl terminal hydrolase.

The 57316 or 33338 molecules and modulators thereof can act as novel therapeutic agents for controlling one or more of cellular proliferative and/or differentiative disorders, hormonal disorders, immune and inflammatory, neurological, cardiovascular disorders, blood vessel disorders, platelet disorders, or viral diseases as described herein.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The 57316 or 33338 molecules of the invention can be used to monitor, treat and/or diagnose a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Typically, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L., (1991) *Crit. Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Ubiquitin carboxyl terminal hydrolase-associated disorders can include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

Ubiquitin carboxyl terminal hydrolase-associated disorders also include immune or inflammation disorders, such as autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency. Other examples of disorders include autoimmune diseases (including, for example, diabetes mellitus, arthritis (including rheumatoid arthritis, juvenile rheumatoid arthritis, osteoarthritis, psoriatic arthritis), multiple sclerosis, encephalomyclitis, myasthenia gravis, systemic lupus erythematosis, autoimmune thyroiditis, dermatitis (including atopic dermatitis and eczematous dermatitis), psoriasis, Sjögren's Syndrome, inflammatory bowel disease (e.g., Crohn's disease and ulcerative colitis), aphthous ulcer, iritis, conjunctivitis, keratoconjunctivitis, respiratory inflammation (e.g., asthma, allergic asthma, and chronic obstructive pulmonary disease), cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, respiratory inflammation (consisting of asthma and chronic obstructive pulmonary diseas) and allergy such as, atopic allergy.

Additional ubiquitin carboxyl terminal hydrolase-associated disorders are neurological disorders. Such neurological disorders include, for example, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyclia and hydromyelia; perinatal brain injury; cerebrovascular diseases, such as those related to hypoxia, ischemia, and infarction, including hypotension, hypoperfusion, and low-flow states, global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer's disease and Pick's disease, degenerative diseases of basal ganglia and brain stem, including Parkinsonism, idiopathic Parkinson's disease (paralysis agitans), progressive supranuclear palsy, corticobasal degenration, multiple system atrophy, including striatonigral degenration, Shy-Drager syndrome, and olivopontocerebellar atrophy, and Huntington's disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The 57316 or 33338 protein, fragments thereof, and derivatives and other variants of the sequence in SEQ ID NO:2 thereof are collectively referred to as "polypeptides or proteins of the invention" or "57316 or 33338 polypeptides or proteins". Nucleic acid molecules encoding such polypeptides or proteins are collectively referred to as "nucleic acids of the invention" or "57316 or 33338 nucleic acids."

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) John Wiley & Sons, N.Y., 6.3.1–6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 57316 or 33338 protein, preferably a mammalian 57316 or 33338 protein, and can further include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 57316 or 33338 protein having less than about 30%, 20%, 10% and more preferably 5% (by dry weight), of non-57316 or 33338 protein (also referred to herein as a "contaminating protein"), or of chemical precursors or non-57316 or 33338 chemicals. When the 57316 or 33338 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 57316 or 33338 (e.g., the protein or polypeptide sequence encoded by SEQ ID NO:1, SEQ ID NO:3, or SEQ ID NO:6, SEQ ID NO:8 or the deposited nucleotide sequence) without abolishing or, more preferably, without substantially altering a biological activity, whereas an "essential" amino acid residue results in such a change. For example, amino acid residues of the present invention that conform to a particular domain or consensus sequence described herein., e.g., those present in the ubiquitin carboxyl terminal hydrolase domains, or zinc fingers in ubiquitin hydrolase domains are particularly non-amenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 57316 or 33338 protein is preferably replaced with another amino acid residue from the same side chain family. Alternatively, in another embodiment, mutations can be introduced randomly along all or part of a 57316 or 33338 coding sequence, such as by saturation mutagenesis, and the resultant mutants can be screened for 57316 or 33338 biological activity to identify mutants that retain activity. Following mutagenesis of SEQ ID NO:1, SEQ ID NO:3, or SEQ ID NO:6, SEQ ID NO:8, or the deposited nucleotide sequence, the encoded protein can be expressed recombinantly and the activity of the protein can be determined.

Particular 57316 and 33338 polypeptides of the present invention have an amino acid sequence substantially identical to the amino acid sequence of SEQ ID NO:2. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1 or 3 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

As used herein, a "biologically active portion" of a 57316 or 33338 protein includes a fragment of a 57316 or 33338 protein that participates in an interaction between a 57316 or 33338 molecule and a non-57316 or 33338 molecule. Biologically active portions of a 57316 or 33338 protein include peptides comprising amino acid sequences sufficiently homologous to or derived from the amino acid sequence of the 57316 or 33338 protein, e.g., the amino acid sequence shown in SEQ ID NO:2 and SEQ ID NO:7, which include fewer amino acids than the full length 57316 or 33338 proteins, and exhibit at least one activity of a 57316 or 33338 protein. Typically, biologically active portions comprise a domain or motif with at least one activity of the 57316 or 33338 protein, e.g., a domain or motif capable of catalyzing an activity described herein, such as the ubiquitination and de-ubiquitination of substrates.

A biologically active portion of a 57316 or 33338 protein can be a polypeptide that is for example, 10, 25, 50, 100, 200, 300, or 400 or more amino acids in length. Biologically active portions of a 57316 or 33338 protein can be used as targets for developing agents that modulate a 57316 or 33338-mediated activity, e.g., a biological activity described herein.

Calculations of homology or sequence identity (the terms "homology" and "identity" are used interchangeably herein) between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 57316 amino acid sequence of SEQ ID NO:2 and having 1354 amino acid residues, at least 406, preferably at least 542, more preferably at least 677, even more preferably at least 812, and even more preferably at least 948, 1083, 1219, or 1354 amino acid residues when the 53176 or polypeptide is aligned.).

In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 33338 amino acid sequence SEQ ID NO:7 having 815 amino acid residues, at least 245, preferably at least 326, more preferably at least 408, even more preferably at least 489, and even more preferably at least 571, 652, 734, or 815 amino acid residues when the 33338 polypeptide is aligned.).

The amino acid residues or nucleotides at corresponding amino acid positions or nucleotide positions are then compared. When a position in the first sequence is occupied by the same amino acid residue or nucleotide as the corresponding position in the second sequence, the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444–453 algorithm which has been incorporated into the GAP program in the GCG software package (available at the bioinformatics page of the website maintained by Accelrys, Inc., San Diego, Calif. USA), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (which should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. (1989) *CABIOS*, 4:11–17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–410. BLAST nucleotide searches can be performed with the NBLAST program, score=100, wordlength=12 to obtain nucleotide sequences homologous to 57316 or 33338 nucleic acid molecules of the invention. BLAST protein searches can be performed with the XBLAST program, score=50, wordlength=3 to obtain amino acid sequences homologous to 57316 or 33338 protein molecules of the invention. To obtain gapped alignments for comparison purposes, gapped BLAST can be utilized as described in Altschul et al. (1997) *Nucl. Acids Res.* 25:3389–3402. When using BLAST and gapped BLAST programs, the default pammeters of the respective programs (e.g., XBLAST and NBLAST) can be used (accessible at the website maintained by National Center for Biotechnology Information. Bethesda, Md. USA).

Isolated Nucleic Acid Molecules

In one aspect, the invention provides an isolated or purified nucleic acid molecule that encodes a 57316 or 33338 polypeptide described herein, e.g., a full-length 57316 or 33338 protein or a fragment thereof, e.g., a biologically active portion of 57316 or 33338 protein. Also included is a nucleic acid fragment suitable for use as a hybridization probe, which can be used, e.g., to a identify nucleic acid molecule encoding a polypeptide of the invention, 57316 or 33338 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or the deposited nucleotide sequence, or a portion of either of these nucleotide sequences. In one embodiment, the nucleic acid molecule includes sequences encoding the human 57316 or 33338 protein (i.e., "the coding region," from nucleotides 192–4250 of SEQ ID NO:1 and from nucleotides 50–2491 of SEQ ID NO:6), as well as 5'-untranslated sequences (nucleotides 1–191 of SEQ ID NO:1 and nucleotides 1–49 of SEQ ID NO:6) or 3'-untranslated sequences (nucleotides 4251–4541 of SEQ ID NO:1 and nucleotides 2492–2736 of SEQ ID NO:6). Alternatively, the nucleic acid molecule can include only the coding region of SEQ ID NO:1 (e.g., nucleotides 192–4250 of SEQ ID NO:1 (SEQ ID NO:3) and 50–2491 of SEQ ID NO:6 (SEQ ID NO:8), and, e.g., no flanking sequences which normally accompany the subject sequence. In another embodiment, the nucleic acid molecule encodes a sequence corresponding to the 1354 amino acid residue protein of SEQ ID NO:2, and the nucleic acid sequence corresponding to the 815 amino acid residue protein of SEQ ID NO;7.

In another embodiment, an isolated nucleic acid molecule of the invention includes a nucleic acid molecule which is a complement of the nucleotide sequence shown in one of SEQ ID NO:1, SEQ ID NO:3, or SEQ ID NO:6, SEQ ID NO:8, the deposited nucleotide sequence, or a portion of any of these sequences. In other embodiments, the nucleic acid molecule of the invention is sufficiently complementary to the nucleotide sequence shown in one of SEQ ID NO:1, SEQ ID NO:3, or SEQ ID NO:6, SEQ ID NO:8, and the deposited nucleotide sequence that it can hybridize with a nucleic acid having that sequence, thereby forming a stable duplex.

In one embodiment, an isolated nucleic acid molecule of the invention includes a nucleotide sequence which is at least about 60%, 65%, 70%, 75%, 80%, 85%, 90%, 91%, 92%, 93%, 94%, 95%, 96%, 97%, 98%, or 99% or more homologous to the entire length of the nucleotide sequence shown in one of SEQ ID NO:1, SEQ ID NO:3, or SEQ ID NO:6, SEQ ID NO:8, the deposited nucleotide sequence, and a portion, preferably of the same length, of any of these nucleotide sequences.

57316 or 33338 Nucleic Acid Fragments

A nucleic acid molecule of the invention can include only a portion of the nucleic acid sequence of one of SEQ ID NOS:1 and 3 and the deposited nucleotide sequence. For example, such a nucleic acid molecule can include a fragment that can be used as a probe or primer or a fragment encoding a portion of a 57316 or 33338 protein, e.g., an immunogenic or biologically active portion of a 57316 or 33338 protein. For example, a fragment can comprise nucleotides encoding a fragment corresponding to residues 461–541of SEQ ID NO:2 or residues 726–812 of SEQ ID NO:7, which is a ubiquitin carboxyl terminal hydrolase-2 domain of human 57316 or 33338. The nucleotide sequence determined from the cloning of the 57316 or 33338 gene facilitates generation of probes and primers for use in identifying and/or cloning other 57316 or 33338 family members, or fragments thereof, as well as 57316 or 33338 homologues, or fragments thereof, from other species.

In another embodiment, a nucleic acid includes a nucleotide sequence that includes part, or all, of the coding region and extends into either (or both) the 5'- or 3'-non-coding region. Other embodiments include a fragment that includes a nucleotide sequence encoding an amino acid fragment described herein. Nucleic acid fragments can encode a specific domain or site described herein or fragments thereof, particularly fragments thereof that are at least about 250 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein.

57316 or 33338 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of one of SEQ ID NO:1, SEQ ID NO:3, or SEQ ID NO:6, SEQ ID NO:8, the deposited nucleotide sequence, and a naturally occurring allelic variant or mutant of SEQ ID NO:1, SEQ ID NO:3, or SEQ ID NO:6, SEQ ID NO:8, or the deposited nucleotide sequence.

In a preferred embodiment the nucleic acid is a probe which is at least 5 or 10, and less than 200, more preferably less than 100, or less than 50, base pairs in length. It should be identical, or differ by 1, or fewer than 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid that encodes, for example, a ubiquitin carboxyl terminal hydrolase-2 domain at about amino acid residues 461–541 of SEQ ID NO:2, or amino acid residues 726–812 of SEQ ID NO:7.

A probe or primer can be derived from the sense or anti-sense strand of a nucleic acid that encodes, for example, a ubiquitin carboxyl-terminal hydrolase-1 domain at about amino acid residues 168–198 of SEQ ID NO:2, or amino acid residues 190–221 of SEQ ID NO:7. A probe or primer can be derived from the sense or anti-sense strand of a nucleic acid that encodes, for example, a zinc finger in ubiquitin hydrolases domain at about amino acid residues 62–148 of SEQ ID NO:7.

In another embodiment a set of primers is provided, e.g., primers suitable for use in a PCR, which can be used to amplify a selected region of a 57316 or 33338 sequence. The primers should be at least 5, 10, or 50 base pairs in length and less than 100–200, base pairs in length. The primers should be identical, or differs by one base from a sequence disclosed herein or from a naturally occurring variant. Primers suitable for amplifying all or a portion of any of the following regions are provided: for example, a ubiquitin carboxyl-terminal hydrolase-1, a ubiquitin carboxyl-terminal hydrolase-2, or a zinc finger in ubiquitin-hydrolases domain.

A nucleic acid fragment can encode an epitope bearing region of a polypeptide described herein.

A nucleic acid fragment encoding a "biologically active portion of a 57316 or 33338 polypeptide" can be prepared by isolating a portion of the nucleotide sequence of one of SEQ ID NO:1, SEQ ID NO:3, or SEQ ID NO:6, SEQ ID NO:8, and the deposited nucleotide sequence, which encodes a polypeptide having a 57316 or 33338 biological activity (e.g., the biological activities of the 57316 or 33338 proteins as described herein), expressing the encoded portion of the 57316 or 33338 protein (e.g., by recombinant expression in vitro) and assessing the activity of the encoded portion of the 57316 or 33338 protein. For example, a nucleic acid fragment encoding a biologically active portion of 57316 or 33338 can include a ubiquitin carboxyl terminal hydrolase-2 domain, e.g., amino acid residues 461–541 of SEQ ID NO:2, and 726–812 of SEQ ID NO:7. A nucleic acid fragment encoding a biologically active portion of a 57316 or 33338 polypeptide can comprise a nucleotide sequence that is greater than 25 or more nucleotides in length.

In one embodiment, a nucleic acid includes a nucleotide sequence which is greater than 260, 300, 400, 600, 800, 1000, 1200, 1400, 1600, 1800, 2000, 2100, 2120, 2140, 2160, 2180, 2200, 2400, 2600, 2800, 3000, 3200, 3400, 3600, 3800, 4000, or 4200 or more nucleotides in length and that hybridizes under stringent hybridization conditions with a nucleic acid molecule having the sequence of one of SEQ ID NO:1, and the deposited nucleotide sequence.

In another embodiment, a nucleic acid includes a nucleotide sequence which is greater than 260, 300, 400, 600, 800, 810, 820, 830, 840, 850, 860, 870, 880, 890, 900, 1000, 1200, 1400, 1600, 1800, 2000, 2200, or 2400, or more nucleotides in length and that hybridizes under stringent hybridization conditions with a nucleic acid molecule having the sequence of one of SEQ ID NO:6, and the deposited nucleotide sequence.

57316 or 33338 Nucleic Acid Variants

The invention further encompasses nucleic acid molecules having a sequence that differs from the nucleotide sequence shown in one of SEQ ID NO:1, SEQ ID NO:3, or SEQ ID NO:6, SEQ ID NO:8, and the deposited nucleotide sequence. Such differences can be attributable to degeneracy of the genetic code (i.e., differences which result in a nucleic acid that encodes the same 57316 or 33338 proteins as those encoded by the nucleotide sequence disclosed herein). In another embodiment, an isolated nucleic acid molecule of the invention encodes a protein having an amino acid sequence which differs by at least 1, but by fewer than 5, 10, 20, 50, or 100, amino acid residues from SEQ ID NO:2 and SEQ ID NO:7. If alignment is needed for this comparison the sequences should be aligned for maximum homology. "Looped" out sequences from deletions or insertions, or mismatches, are considered differences.

Nucleic acids of the invention can be chosen for having codons, which are preferred, or non-preferred, for a particular expression system. For example, the nucleic acid can be one in which at least one codon, preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism), or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid has a sequence that differs from that of one of SEQ ID NO:1, SEQ ID NO:3, or SEQ ID NO:6, SEQ ID NO:8, and the deposited nucleotide sequence, e.g., as follows: by at least one, but fewer than 10, 20, 30, or 40, nucleotide residues; or by at least one but fewer than 1%, 5%, 10% or 20% of the nucleotide residues in the subject nucleic acid. If necessary for this analysis, the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in one of SEQ ID NO:1, SEQ ID NO:3, or SEQ ID NO:6, SEQ ID NO:8, the deposited nucleotide sequence, or a fragment of one of these sequences. Such nucleic acid molecules can readily be identified as being able to hybridize under stringent conditions to the nucleotide sequence of one of SEQ ID NO:1, SEQ ID NO:3, or SEQ ID NO:6, SEQ ID NO:8, the deposited nucleotide sequence, or a fragment of one of these sequences. Nucleic acid molecules corresponding to orthologs, homologs, and allelic variants of the 57316 or 33338 cDNAs of the invention can further be isolated by mapping to the same chromosome or locus as the 57316 or 33338 gene.

Preferred variants include those that are correlated with any of the 57316 or 33338 biological activities described herein, e.g., hydrolyzing amide derivatives of the ubiquitin carboxyl terminus, including those of lysine (epsilon-amino), glycine methyl ester, and spermidine.

Allelic variants of 57316 or 33338 (e.g., human 57316 or 33338) include both functional and non-functional proteins. Functional allelic variants are naturally occurring amino acid sequence variants of the 57316 or 33338 protein within a population that maintain the ability to mediate any of the 57316 or 33338 biological activities described herein.

Functional allelic variants will typically contain only conservative substitution of one or more amino acids of SEQ ID NO:2 and SEQ ID NO:7, or substitution, deletion or insertion of non-critical residues in non-critical regions of the protein. Non-functional allelic variants are naturally-occurring amino acid sequence variants of the 57316 or 33338 (e.g., human 57316 or 33338) protein within a population that do not have the ability to mediate any of the 57316 or 33338 biological activities described herein. Non-functional allelic variants will typically contain a non-conservative substitution, a deletion, or insertion, or premature truncation of the amino acid sequence of SEQ ID NO:2 and SEQ ID NO:7, or a substitution, insertion, or deletion in critical residues or critical regions of the protein.

Moreover, nucleic acid molecules encoding other 57316 or 33338 family members and, thus, which have a nucleotide sequence which differs from the 57316 or 33338 sequences of one of SEQ ID NO:1, SEQ ID NO:3, or SEQ ID NO:6, SEQ ID NO:8, and the deposited nucleotide sequence are within the scope of the invention.

Antisense Nucleic Acid Molecules, Ribozymes and Modified 57316 or 33338 Nucleic Acid Molecules In another aspect, the invention features an isolated nucleic acid molecule that is antisense to 57316 or 33338. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 57316 or 33338 coding strand, or to only a portion thereof (e.g., the coding region of human 57316 or 33338 corresponding to SEQ ID NO:3 or SEQ ID NO:7). In another embodiment, the antisense nucleic acid molecule is antisense to a "non-coding region" of the coding strand of a nucleotide sequence encoding 57316 or 33338 (e.g., the 5'- and 3'-untranslated regions).

An antisense nucleic acid can be designed such that it is complementary to the entire coding region of 57316 or 33338 mRNA, but more preferably is an oligonucleotide that is antisense to only a portion of the coding or non-coding region of 57316 or 33338 mRNA. For example, the antisense oligonucleotide can be complementary to the region surrounding the translation start site of 57316 or 33338 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, or 80 or more nucleotide residues in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 57316 or 33338 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al. (1987) *Nucl. Acids. Res.* 15:6625–6641). The antisense nucleic acid molecule can also comprise a 2'-o-methylribonucleotide (Inoue et al. (1987) *Nucl. Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 57316 or 33338-encoding nucleic acid can include one or more sequences complementary to the nucleotide sequence of a 57316 or 33338 cDNA disclosed herein (i.e., SEQ ID NO:1 or SEQ ID NO:3 and SEQ ID NO:6 or SEQ ID NO:8), and a sequence having known catalytic sequence responsible for mRNA cleavage (see, for example, U.S. Pat. No. 5,093,246 or Haselhoff et al. (1988, *Nature* 334:585–591). For example, a derivative of a Tetrahymena L-19 IVS RNA can be constructed in which the nucleotide sequence of the active site is complementary to the nucleotide sequence to be cleaved in a 57316 or 33338-encoding mRNA (e.g., U.S. Pat. No. 4,987,071; and U.S. Pat. No. 5,116,742). Alternatively, 57316 or 33338 mRNA can be used to select a catalytic RNA having a specific ribonuclease activity from a pool of RNA molecules (e.g., Bartel et al.(1993) *Science* 261:1411–1418).

57316 or 33338 gene expression can be inhibited by targeting nucleotide sequences complementary to the regulatory region of the 57316 or 33338 (e.g., the 57316 or 33338 promoter and/or enhancers) to form triple helical structures that prevent transcription of the 57316 or 33338 gene in target cells (Helene, 1991, Anticancer Drug Des. 6:569–584; Helene, et al.(1992) *Ann. N.Y. Acad. Sci.* 660:27–36; Maher(1992) *Bioassays* 14:807–815). The potential sequences that can be targeted for triple helix formation can be increased by creating a so-called "switchback" nucleic acid molecule. Switchback molecules are synthesized in an alternating 5' to 3', 3' to 5' manner, such that they hybridize with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 57316 or 33338 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (Hyrup et al.(1996) *Bioorg. Med. Chem.* 4:5–23). As used herein, the terms "peptide nucleic acid" (PNA) refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al., *Proc. Natl. Acad. Sci. USA* 93:14670–14675.

PNAs of 57316 or 33338 nucleic acid molecules can be used in therapeutic and diagnostic applications. For example, PNAs can be used as antisense or anti-gene agents for sequence-specific modulation of gene expression by, for example, inducing transcription or translation arrest or inhibiting replication. PNAs of 57316 or 33338 nucleic acid molecules can also be used in the analysis of single base pair mutations in a gene, (e.g., by PNA-directed PCR clamping); as 'artificial restriction enzymes' when used in combination with other enzymes, (e.g., S1 nucleases, as described in Hyrup et al. (1996) supra; or as probes or primers for DNA sequencing or hybridization (Hyrup et al(1996) supra; Perry-O'Keefe, supra).

In other embodiments, the oligonucleotide can include other appended groups such as peptides (e.g., for targeting host cell receptors in vivo), or agents facilitating transport across the cell membrane (e.g., Letsinger et al (1989) *Proc. Natl. Acad. Sci. USA* 86:6553–6556; Lemaitre et al., (1987) *Proc. Natl. Acad. Sci. USA* 84:648–652; PCT publication number WO 88/09810) or the blood-brain barrier (see, e.g., PCT publication number WO 89/10134). In addition, oligonucleotides can be modified with hybridization-triggered cleavage agents (e.g., Krol et al. (1988) *Bio-Techniques* 6:958–976) or intercalating agents (e.g., Zon, 1988, Pharm. Res. 5:539–549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 57316 or 33338 nucleic acid of the invention, two complementary regions, one having a fluorophore and the other having a quencher, such that the molecular beacon is useful for quantitating the presence of the 57316 or 33338 nucleic acid of the invention in a sample. Molecular beacon nucleic acids are described, for example, in U.S. Pat. No. 5,854,033, U.S. Pat. No. 5,866,336, and U.S. Pat. No. 5,876,930.

Isolated 57316 or 33338 Polypeptides

In another aspect, the invention features, an isolated 57316 or 33338 protein, or fragment, e.g., a biologically active portion, for use as immunogens or antigens to raise or test (or more generally to bind) anti-57316 or 33338 antibodies. 57316 or 33338 protein can be isolated from cells or tissue sources using standard protein purification techniques. 57316 or 33338 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present when expressed in a native cell.

In a preferred embodiment, a 57316 or 33338 polypeptide has one or more of the following characteristics: it has a molecular weight, amino acid composition or other physical characteristic of a 57316 protein of SEQ ID NO:2, or a 33338 protein of SEQ ID NO:7;

it has an overall sequence identity of at least 60–65%, preferably at least 70%, more preferably at least 75, 80, 85, 86, 87, 88, 89, 90, 91, 92, 93, 94, 95, 96, 97, 98, or 99% or more, with at least a portion of SEQ ID NO:2 and SEQ ID NO:7;

it has a ubiquitin carboxyl terminal hydrolase-1 domain which is preferably about 70%, 80%, 90%, 95%, 96%, 97%, 98%, 99% or more, identical with amino acid residues 168–198 of SEQ ID NO:2, and 190–221 of SEQ ID NO:7;

it has a ubiquitin carboxyl terminal hydrolase-2 domain which is preferably about 70%, 80%, 90%, 95%, 96%, 97%, 98%, 99% or more, identical with amino acid residues 461–541 of SEQ ID NO:2 and 726–812 of SEQ ID NO:7;

In a preferred embodiment, the 33338 polypeptide has one or more of the following characteristics described in the art (e.g., Miller et al., supra, and references cited therein).

the 33338 protein has a zinc fingers in ubiquitin hydrolases domain which is preferably about 70%, 80%, 90%, 95%, 96%, 97%, 98%, 99% or more, identical with amino acid residues 62–148 of SEQ ID NO:7.

In a preferred embodiment, the 57316 or 33338 protein or fragment thereof differs only insubstantially, if at all, from the corresponding sequence in SEQ ID NO:2 and SEQ ID NO:7. In one embodiment, it differs by at least one, but by fewer than 15, 10 or preferably 5 amino acid residues. In another, it differs from the corresponding sequence in SEQ ID NO:2 and SEQ ID NO:7 by at least one residue but fewer than 20%, 15%, 10% or 5% of the residues differ from the corresponding sequence in SEQ ID NO:2 and SEQ ID NO:7 (if this comparison requires alignment the sequences should be aligned for maximum homology). "Looped" out sequences from deletions or insertions, or mismatches, are considered differences). The differences are, preferably, differences or changes at a non-essential amino acid residues or involve a conservative substitution of one residue for another. In a preferred embodiment the differences are not in residues 168–198 or 461–541 of SEQ ID NO:2, or at residues 62–148 or 190–221, or 726–812 of SEQ ID NO:7.

Other embodiments include a protein that has one or more changes in amino acid sequence, relative to SEQ ID NO:2 and SEQ ID NO:7 (e.g., a change in an amino acid residue which is not essential for activity). Such 57316 or 33338 proteins differ in amino acid sequence from SEQ ID NO:2 and SEQ ID NO:7, yet retain biological activity.

In one embodiment, the protein includes an amino acid sequence at least about 60%, 65%, 70%, 75%, 80%, 85%, 90%, 95%, 98% or more homologous to SEQ ID NO:2 and SEQ ID NO:7.

A 57316 or 33338 protein or fragment is provided which has an amino acid sequence which varies from SEQ ID NO:2 and SEQ ID NO:7 in one or both of the regions corresponding to, for example residues 1–67 of SEQ ID NO:2, and residues 1–60 of SEQ ID NO:7, by at least one, but by fewer than 15, 10 or 5 amino acid residues, but which does not differ from SEQ ID NO:2 and SEQ ID NO:7 in the region corresponding to residues 168–198 and residues 461–541 of SEQ ID NO:2, and residues 62–148, and residues 190–221, and residues 726–812 of SEQ ID NO:7. (if this comparison requires alignment the sequences should be aligned for maximum homology. "Looped" out sequences from deletions or insertions, or mismatches, are considered differences). In some embodiments the difference is at a non-essential residue or is a conservative substitution, while in others the difference is at an essential residue or is a non-conservative substitution.

A biologically active portion of a 57316 or 33338 protein can include at least the 57316 or 33338 ubiquitin carboxyl terminal hydrolase-1 domain. Moreover, other biologically active portions, in which other regions of the protein are deleted, can be prepared by recombinant techniques and evaluated for one or more of the functional activities of a native 57316 or 33338 protein.

In a preferred embodiment, the 57316 or 33338 protein has the amino acid sequence SEQ ID NO:2 and SEQ ID NO:7. In other embodiments, the 57316 or 33338 protein is substantially identical to SEQ ID NO:2 and SEQ ID NO:7. In yet another embodiment, the 57316 or 33338 protein is substantially identical to SEQ ID NO:2 and SEQ ID NO:7 and retains the functional activity of the protein of SEQ ID NO:2 and SEQ ID NO:7.

57316or 33338 Chimeric or Fusion Proteins

In another aspect, the invention provides 57316 or 33338 chimeric or fusion proteins. As used herein, a 57316 or 33338 "chimeric protein" or "fusion protein" includes a 57316 or 33338 polypeptide linked to a non-57316 or 33338 polypeptide. A "non-57316 or 33338 polypeptide" refers to a polypeptide having an amino acid sequence corresponding to a protein which is not substantially homologous to the 57316 or 33338 protein, e.g., a protein which is different from the 57316 or 33338 protein and which is derived from the same or a different organism. The 57316 or 33338 polypeptide of the fusion protein can correspond to all or a portion e.g., a fragment described herein of a 57316 or 33338 amino acid sequence. In a preferred embodiment, a 57316 or 33338 fusion protein includes at least one or more biologically active portions of a 57316 or 33338 protein. The non-57316 or 33338 polypeptide can be fused to the amino or carboxyl terminus of the 57316 or 33338 polypeptide.

The fusion protein can include a moiety that has a high affinity for a ligand. For example, the fusion protein can be a GST-57316 or 33338 fusion protein in which the 57316 or 33338 sequences are fused to the carboxyl terminus of the GST sequences. Such fusion proteins can facilitate the purification of recombinant 57316 or 33338. Alternatively, the fusion protein can be a 57316 or 33338 protein containing a heterologous signal sequence at its amino terminus. In certain host cells (e.g., mammalian host cells), expression and/or secretion of 57316 or 33338 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge C1 and C2 sequences of an immunoglobulin or human serum albumin.

The 57316 or 33338 fusion proteins of the invention can be incorporated into pharmaceutical compositions and administered to a subject in vivo. The 57316 or 33338 fusion proteins can be used to affect the bioavailability of a 57316 or 33338 substrate. 57316 or 33338 fusion proteins can be useful therapeutically for the treatment of disorders caused by, for example, (i) aberrant modification or mutation of a gene encoding a 57316 or 33338 protein; (ii) mis-regulation of the 57316 or 33338 gene; and (iii) aberrant post-translational modification of a 57316 or 33338 protein.

Moreover, the 57316 or 33338-fusion proteins of the invention can be used as immunogens to produce anti-57316 or 33338 antibodies in a subject, to purify 57316 or 33338 ligands and in screening assays to identify molecules that inhibit the interaction of 57316 or 33338 with a 57316 or 33338 substrate.

Expression vectors are commercially available that already encode a fusion moiety (e.g., a GST polypeptide). A 57316 or 33338-encoding nucleic acid can be cloned into such an expression vector such that the fusion moiety is linked in-frame to the 57316 or 33338 protein.

Variants of 57316 or 33338 Proteins

In another aspect, the invention also features a variant of a 57316 or 33338 polypeptide, e.g., which functions as an agonist (mimetics) or as an antagonist. Variants of the 57316 or 33338 proteins can be generated by mutagenesis, e.g., discrete point mutation, the insertion or deletion of sequences or the truncation of a 57316 or 33338 protein. An agonist of the 57316 or 33338 proteins can retain substantially the same, or a subset, of the biological activities of the naturally occurring form of a 57316 or 33338 protein. An antagonist of a 57316 or 33338 protein can inhibit one or more of the activities of the naturally occurring form of the 57316 or 33338 protein by, for example, competitively modulating a 57316 or 33338-mediated activity of a 57316 or 33338 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 57316 or 33338 protein.

Variants of a 57316 or 33338 protein can be identified by screening combinatorial libraries of mutants, e.g., truncation mutants, of a 57316 or 33338 protein for agonist or antagonist activity.

Libraries of fragments e.g., amino-terminal, carboxyl-terminal, or internal fragments, of a 57316 or 33338 protein coding sequence can be used to generate a variegated population of fragments for screening and subsequent selection of variants of a 57316 or 33338 protein.

Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a technique which enhances the frequency of functional mutants in the libraries, can be used in combination with the screening assays to identify 57316 or 33338 variants (Arkin et al. (1992) *Proc. Natl. Acad. Sci. USA* 89:7811–7815; Delgrave et al. (1993) *Protein Engr.* 6:327–331).

Cell based assays can be exploited to analyze a variegated 57316 or 33338 library. For example, a library of expression vectors can be transfected into a cell line, e.g., a cell line, which ordinarily responds to 57316 or 33338 in a substrate-dependent manner. The transfected cells are then contacted with 57316 or 33338 and the effect of the expression of the mutant on signaling by the 57316 or 33338 substrate can be detected, e.g., by measuring changes in cell growth and/or enzymatic activity. Plasmid DNA can then be recovered from the cells that score for inhibition, or alternatively, potentiation of signaling by the 57316 or 33338 substrate, and the individual clones further characterized.

In another aspect, the invention features a method of making a 57316 or 33338 polypeptide, e.g., a peptide having a non-wild-type activity, e.g., an antagonist, agonist, or super agonist of a naturally-occurring 57316 or 33338 polypeptide, e.g., a naturally-occurring 57316 or 33338 polypeptide. The method includes: altering the sequence of a 57316 or 33338 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 57316 or 33338 polypeptide a biological activity of a naturally occurring 57316 or 33338 polypeptide. The method includes: altering the sequence, e.g., by substitution or deletion of one or more residues, of a 57316 or 33338 polypeptide, e.g., altering the sequence of a non-conserved region, or a domain or residue described herein, and testing the altered polypeptide for the desired activity.

Anti-57316 or 33338 Antibodies

In another aspect, the invention provides an anti-57316 or 33338 antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, F(ab) and F(ab')$^2$ fragments which can be generated by treating the antibody with an enzyme such as papain or pepsin respectively.

The antibody can be a polyclonal, monoclonal, recombinant, e.g., a chimeric, humanized, fully-human, non-human, e.g., murine, or single chain antibody. In a preferred embodiment, it has effector function and can fix complement. The antibody can be coupled to a toxin or imaging agent.

A full-length 57316 or 33338 protein or, antigenic peptide fragment of 57316 or 33338 can be used as an immunogen or can be used to identify anti-57316 or 33338 antibodies made with other immunogens, e.g., cells, membrane preparations, and the like. The antigenic peptide of 57316 or 33338 should include at least 8 amino acid residues of the amino acid sequence shown in SEQ ID NO:2 and SEQ ID NO:7 and encompasses an epitope of 57316 or 33338. Preferably, the antigenic peptide includes at least 10 amino acid residues, more preferably at least 15 amino acid residues, even more preferably at least 20 amino acid residues, and most preferably at least 30 amino acid residues.

Fragments of 57316 which include about residues 780–797 of SEQ ID NO:2 can be used to make antibodies, e.g., for use as immunogens or to characterize the specificity of an antibody, against domains described herein or hydrophobic regions of the 57316 protein. Similarly, a fragment of 57316 which include about residues 617–623 or 850–858 of SEQ ID NO:2 can be used to make an antibody against a hydrophilic region of the 57316 protein. FIG. 1 depicts a hydropathy plot of human 57316 which can be used to show areas of hydrophobicity or hydrophilicity, against which 57316 antibodies can be made.

Fragments of 33338 which include about residues 313 to 320 of SEQ ID NO:7 can be used to make antibodies, e.g., for use as immunogens or to characterize the specificity of an antibody, against domains as described herein, or hydrophobic regions of the 57316 or 33338 protein. Similarly, a fragment of 33338 which include about residues 206–211 or 485–493 of SEQ ID NO:7 can be used to make an antibody against a hydrophilic region of the 33338 protein. FIG. 1 depicts a hydropathy plot of human 33338 which can be used to show areas of hydrophobicity or hydrophilicity, against which 33338 antibodies can be made.

Antibodies reactive with, or specific or selective for, any of these regions, or other regions or domains described herein are provided.

Preferred epitopes encompassed by the antigenic peptide are regions of 57316 or 33338 are located on the surface of the protein, e.g., hydrophilic regions (see FIG. 1), as well as regions with high antigenicity. For example, an Emini surface probability analysis of the human 57316 or 33338 protein sequence can be used to indicate the regions that have a particularly high probability of being localized to the surface of the 57316 or 33338 protein and are thus likely to constitute surface residues useful for targeting antibody production. In a preferred embodiment the antibody binds an epitope on any domain or region on 57316 or 33338 proteins described herein.

In a preferred embodiment the antibody binds an epitope on any domain or region on 57316 or 33338 proteins described herein.

Chimeric, humanized, but most preferably, completely human antibodies are desirable for applications which include repeated administration, e.g., therapeutic treatment (and some diagnostic applications) of human patients.

The anti-57316 or 33338 antibody can be a single chain antibody. A single-chain antibody (scFV) can be engineered as described in for example, Colcher et al. (1999) *Ann. N.Y. Acad. Sci.* 880:263–280; and Reiter (1996) *Clin. Cancer Res.* 2:245–252. The single chain antibody can be dimerized or multimerized to generate multivalent antibodies having specificities for different epitopes of the same target 57316 or 33338 protein.

In a preferred embodiment, the antibody has reduced or no ability to bind an Fc receptor. For example, it can be an isotype, subtype, fragment or other mutant, which does not support binding to an Fc receptor, e.g., it can have a mutated or deleted Fc receptor binding region.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

An anti-57316 or 33338 antibody (e.g., monoclonal antibody) can be used to isolate 57316 or 33338 by standard techniques, such as affinity chromatography or immunoprecipitation. Moreover, an anti-57316 or 33338 antibody can be used to detect 57316 or 33338 protein (e.g., in a cellular lysate or cell supernatant) in order to evaluate the abundance and pattern of expression of the protein. Anti-57316 or 33338 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In preferred embodiments, an antibody can be made by immunizing with a purified 57316 and 33338 antigen, or a fragment thereof, e.g., a fragment described herein, a membrane associated antigen, tissues, e.g., crude tissue preparations, whole cells, preferably living cells, lysed cells, or cell fractions, e.g., membrane fractions.

Antibodies which bind only a native 57316 and 33338 protein, only denatured or otherwise non-native 57316 and 33338 protein, or which bind both, are within the invention. Antibodies with linear or conformational epitopes are within the invention. Conformational epitopes sometimes can be identified by identifying antibodies which bind to native but not denatured 57316 and 33338 protein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 57316 or 33338 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 57316 or 33338 proteins, mutant forms of 57316 or 33338 proteins, fusion proteins, and the like).

The recombinant expression vectors of the invention can be designed for expression of 57316 or 33338 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel (1990), Gene Expression Technology: Methods in Enzymology 185, Academic Press, San Diego). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith et al. (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 57316 or 33338 activity assays, (e.g., direct assays or competitive assays described in detail below), or to generate antibodies specific for 57316 or 33338 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six weeks).

To maximize recombinant protein expression in E. coli, the protein is expressed in a host bacterial strain with an impaired capacity to proteolytically cleave the recombinant protein (Gottesman, 1990, Gene Expression Technology: Methods in Enzymology 185, Academic Press, San Diego, 119–128). Another strategy is to alter the nucleic acid sequence of the nucleic acid to be inserted into an expression vector so that the individual codons for each amino acid are those preferentially utilized in E. coli (Wada et al. (1992) Nucl. Acids Res. 20:2111–2118). Such alteration of nucleic acid sequences of the invention can be carried out by standard DNA synthesis techniques.

The 57316 or 33338 expression vector can be a yeast expression vector, a vector for expression in insect cells, e.g., a baculovirus expression vector, or a vector suitable for expression in mammalian cells.

When used in mammalian cells, the expression vector's control functions are often provided by viral regulatory elements. For example, commonly used viral promoters are derived from polyoma, adenovirus 2, cytomegalovirus and simian virus 40 (SV40).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268–277), lymphoid-specific promoters (Calame et al. (1988) Adv. Immunol. 43:235–275), in particular promoters of T cell receptors (Winoto et al. (1989) EMBO J. 8:729–733) and immunoglobulins (Banerji et al. (1983) Cell 33:729–740; Queen et al. (1983) Cell 33:741–748), neuron-specific promoters (e.g., the neurofilament promoter; Byrne et al. (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Patent Application publication number 264,166). Developmentally-regulated promoters are also encompassed, for example, the murine hox promoters (Kessel et al. (1990) Science 249:374–379) and the alpha-fetoprotein promoter (Campes et al. (1989) Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of anti sense RNA in a variety of cell types. The antisense expression vector can be in the form of a recombinant plasmid, phagemid or attenuated virus. For a discussion of the regulation of gene expression using antisense genes, see Weintraub, H. et al. (1986) Trends Genet. 1:Review.

Another aspect the invention provides a host cell which includes a nucleic acid molecule described herein, e.g., a 57316 or 33338 nucleic acid molecule within a recombinant expression vector or a 57316 or 33338 nucleic acid molecule containing sequences which allow it to homologously recombine into a specific site of the host cell's genome. The terms "host cell" and "recombinant host cell" are used interchangeably herein. Such terms refer not only to the particular subject cell, but also to the progeny or potential progeny of such a cell. Because certain modifications can occur in succeeding generations due to either mutation or environmental influences, such progeny may not, in fact, be identical to the parent cell, but are included within the scope of the term as used herein.

A host cell can be any prokaryotic or eukaryotic cell. For example, a 57316 or 33338 protein can be expressed in bacterial cells such as E. coli, insect cells, yeast or mammalian cells (such as Chinese hamster ovary (CHO) cells) or COS cells. Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 57316 or 33338 protein. Accordingly, the invention further provides methods for producing a 57316 or 33338 protein using the host cells of the invention. In one embodiment, the method includes culturing the host cell of the invention (into which a recombinant expression vector encoding a 57316 or 33338 protein has been introduced) in a suitable medium such that a 57316 or 33338 protein is produced. In another embodiment, the method further includes isolating a 57316 or 33338 protein from the medium or the host cell.

In another aspect, the invention features, a cell or purified preparation of cells which include a 57316 or 33338 transgene, or which otherwise mis-express 57316 or 33338. The cell preparation can consist of human or non-human cells, e.g., rodent cells, e.g., mouse or rat cells, rabbit cells, or pig cells. In preferred embodiments, the cell or cells include a 57316 or 33338 transgene, e.g., a heterologous form of a 57316 or 33338, e.g., a gene derived from humans (in the case of a non-human cell). The 57316 or 33338 transgene can be mis-expressed, e.g., over-expressed or under-expressed. In other preferred embodiments, the cell or cells include a gene that mis-expresses an endogenous 57316 or 33338, e.g., a gene the expression of which is disrupted, e.g., a knockout. Such cells can serve as a model for studying disorders that are related to mutated or mis-expressed 57316 or 33338 alleles or for use in drug screening.

In another aspect, the invention includes, a human cell, e.g., a hematopoietic stem cell, transformed with nucleic acid that encodes a subject 57316 or 33338 polypeptide.

Also provided are cells, preferably human cells, e.g., human hematopoietic or fibroblast cells, in which an endogenous 57316 or 33338 is under the control of a regulatory sequence that does not normally control expression of the endogenous 57316 or 33338 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 57316 or 33338 gene. For example, an endogenous 57316 or 33338 gene that is "transcriptionally silent," e.g., not normally expressed, or expressed only at very low levels, can be activated by inserting a regulatory element that is capable of promoting the expression of a normally expressed gene product in that cell. Techniques such as targeted homologous recombination, can be used to insert the heterologous DNA as described (e.g., U.S. Pat. No. 5,272,071; PCT publication number WO 91/06667).

Transgenic Animals

The invention provides non-human transgenic animals. Such animals are useful for studying the function and/or activity of a 57316 or 33338 protein and for identifying and/or evaluating modulators of 57316 or 33338 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 57316 or 33338 gene has been altered, e.g., by homologous recombination between the endogenous gene and an exogenous DNA molecule introduced into a cell of the animal (e.g., an embryonic cell of the animal, prior to development of the animal).

Intronic sequences and polyadenylation signals can also be included in the transgene to increase the efficiency of expression of the transgene. A tissue-specific regulatory sequence(s) can be operably linked to a transgene of the invention to direct expression of a 57316 or 33338 protein to particular cells. A transgenic founder animal can be identified based upon the presence of a 57316 or 33338 transgene in its genome and/or expression of 57316 or 33338 mRNA in tissues or cells of the animals. A transgenic founder animal can then be used to breed additional animals carrying the transgene. Moreover, transgenic animals carrying a transgene encoding a 57316 or 33338 protein can further be bred to other transgenic animals carrying other transgenes.

57316 or 33338 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk- or egg-specific promoter, and recovered from the milk or eggs produced by the animal. Suitable animals are mice, pigs, cows, goats, and sheep.

The invention also includes a population of cells from a transgenic animal, as described herein.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 57316 or 33338 protein (e.g., via a recombinant expression vector in a host cell in gene therapy applications), to detect a 57316 or 33338 mRNA (e.g., in a biological sample), to detect a genetic alteration in a 57316 or 33338 gene and to modulate 57316 or 33338 activity, as described further below. The 57316 or 33338 proteins can be used to treat disorders characterized by insufficient or excessive production of a 57316 or 33338 substrate or production of 57316 or 33338 inhibitors. In addition, the 57316 or 33338 proteins can be used to screen for naturally occurring 57316 or 33338 substrates, to screen for drugs or compounds which modulate 57316 or 33338 activity, as well as to treat disorders characterized by insufficient or excessive production of 57316 or 33338 protein or production of 57316 or 33338 protein forms which have decreased, aberrant or unwanted activity compared to 57316 or 33338 wild-type protein. Exemplary disorders include those in which ubiquitin carboxyl terminal hydrolase activity is aberrant (e.g., Alzheimer's disease, diffuse Lewy body disease, motor neuron disease). Moreover, the anti-57316 or 33338 antibodies of the invention can be used to detect and isolate 57316 or 33338 proteins, regulate the bioavailability of 57316 or 33338 proteins, and modulate 57316 or 33338 activity.

A method of evaluating a compound for the ability to interact with, e.g., bind to, a subject 57316 or 33338 polypeptide is provided. The method includes: contacting the compound with the subject 57316 or 33338 polypeptide; and evaluating the ability of the compound to interact with, e.g., to bind or form a complex with, the subject 57316 or 33338 polypeptide. This method can be performed in vitro, e.g., in a cell free system, or in vivo, e.g., in a two-hybrid interaction trap assay. This method can be used to identify naturally-occurring molecules that interact with a subject 57316 or 33338 polypeptide. It can also be used to find natural or synthetic inhibitors of a subject 57316 or 33338 polypeptide. Screening methods are discussed in more detail below.

Screening Assays

The invention provides screening methods (also referred to herein as "assays") for identifying modulators, i.e., candidate or test compounds or agents (e.g., proteins, peptides, peptidomimetics, peptoids, small molecules or other drugs) which bind with 57316 or 33338 proteins, have a stimulatory or inhibitory effect on, for example, 57316 or 33338 expression or 57316 or 33338 activity, or have a stimulatory or inhibitory effect on, for example, the expression or activity of a 57316 or 33338 substrate. Compounds thus identified can be used to modulate the activity of target gene products (e.g., 57316 or 33338 genes) in a therapeutic protocol, to elaborate the biological function of the target gene product, or to identify compounds that disrupt normal target gene interactions.

In one embodiment, the invention provides assays for screening candidate or test compounds that are substrates of a 57316 or 33338 protein or polypeptide or a biologically active portion thereof. In another embodiment, the invention provides assays for screening candidate or test compounds that bind to or modulate the activity of a 57316 or 33338 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; e.g., Zuckermann et al. (1994) *J. Med. Chem.* 37:2678–2685); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries have been described (e.g., DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al, (1993) *Science* 261:1303; Carrell et al. (1994) Angew. *Chem. Int. Ed. Engl.* 33:2059; Carell et al. (1994) Angew. *Chem. Int. Ed. Engl.* 33:2061; and Gallop et al., (1994) *J. Med. Chem.* 37:1233).

Libraries of compounds can be presented in solution (e.g., Houghten, (1992) *Biotechniques* 13:412–421), or on beads Lam (1991) *Nature* 354:82–84), chips (Fodor, 1993, *Nature* 364:555–556), bacteria (U.S. Pat. No. 5,223,409), spores (U.S. Pat. No. 5,223,409), plasmids (Cull et al. (1992) *Proc. Natl. Acad. Sci. USA* 89:1865–1869), or on phage (Scott et al. (1990) *Science* 249:386–390; Devlin (1990) *Science* 249:404–406; Cwirla et al. (1990) *Proc. Natl. Acad. Sci. USA* 87:6378–6382; Felici (1991) *J. Mol. Biol.* 222:301–310; U.S. Pat. No. 5,223,409).

In one embodiment, an assay is a cell-based assay in which a cell which expresses a 57316 or 33338 protein or biologically active portion thereof is contacted with a test compound, and the ability of the test compound to modulate 57316 or 33338 activity is determined. Determining the ability of the test compound to modulate 57316 or 33338 activity can be accomplished by monitoring, for example, changes in enzymatic activity. The cell, for example, can be of mammalian origin.

The ability of the test compound to modulate 57316 or 33338 binding to a compound, e.g., a 57316 or 33338 substrate, or to bind to 57316 or 33338 can also be evaluated. This can be accomplished, for example, by coupling the compound, e.g., the substrate, with a radioisotope or enzymatic label such that binding of the compound, e.g., the substrate, to 57316 or 33338 can be determined by detecting the labeled compound, e.g., substrate, in a complex. Alternatively, 57316 or 33338 could be coupled with a radioisotope or enzymatic label to monitor the ability of a test compound to modulate 57316 or 33338 binding to a 57316 or 33338 substrate in a complex. For example, compounds (e.g., 57316 or 33338 substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 57316 or 33338 substrate) to interact with 57316 or 33338 with or without the labeling of any of the interactants can be evaluated. For example, a microphysiometer can be used to detect the interaction of a compound with 57316 or 33338 without the labeling of either the compound or the 57316 or 33338 (McConnell et al. (1992,) *Science* 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 57316 or 33338.

In yet another embodiment, a cell-free assay is provided in which a 57316 or 33338 protein or biologically active portion thereof is contacted with a test compound and the ability of the test compound to bind to the 57316 or 33338 protein or biologically active portion thereof is evaluated. Preferred biologically active portions of the 57316 or 33338 proteins to be used in assays of the present invention include fragments that participate in interactions with non-57316 or 33338 molecules, e.g., fragments with high surface probability scores.

Soluble and/or membrane-bound forms of isolated proteins (e.g., 57316 or 33338 proteins or biologically active portions thereof) can be used in the cell-free assays of the invention. When membrane-bound forms of the protein are used, it can be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-{(3-cholamidopropyl) dimethylamminio}-1-propane sulfonate (CHAPS), 3-{(3-cholamidopropyl) dimethylamminio}-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET; e.g., U.S. Pat. No. 5,631,169; U.S. Pat. No. 4,868,103). A fluorophore label is selected such that a first donor molecule's emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 57316 or 33338 protein to bind to a target molecule can be accomplished using real-time biomolecular interaction analysis (BIA; e.g., Sjolander et al. (1991) *Anal. Chem.* 63:2338–2345; Szabo et al. (1995) *Curr. Opin. Struct. Biol.* 5:699–705). "Surface plasmon resonance" (SPR) or "BIA" detects biospecific interactions in real time, without labeling any of the interactants (e.g., BIACORE™). Changes in the mass at the binding surface (indicative of a binding event) result in alterations of the refractive index of light near the surface (the optical phenomenon of SPR), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It can be desirable to immobilize either 57316 or 33338, an anti-57316 or 33338 antibody or its target molecule to facilitate separation of complexed from non-complexed forms of one or both of the proteins, as well as to accommodate automation of the assay. Binding of a test compound to a 57316 or 33338 protein, or interaction of a 57316 or 33338 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/57316 or 33338 fusion proteins or glutathione-S-transferase/target fusion proteins can be adsorbed onto glutathione SEPHAROSE™ beads (Sigma Chemical, St. Louis, Mo.) or glutathione-derivatized microtiter plates, which are then combined with the test compound or the test compound and either the non-adsorbed target protein or 57316 or 33338 protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 57316 or 33338 binding or activity determined using standard techniques.

Other techniques for immobilizing either a 57316 or 33338 protein or a target molecule on matrices include using conjugation of biotin and streptavidin. Biotinylated 57316 or 33338 protein or target molecules can be prepared from biotin-N-hydroxy-succinimide using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, non-reacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 57316 or 33338 protein or target molecules but which do not interfere with binding of the 57316 or 33338 protein to its target molecule. Such antibodies can be derivatized to the wells of the plate, and unbound target or 57316 or 33338 protein trapped in the wells by antibody conjugation. Methods for detecting such complexes, in addition to those described above for the GST-immobilized complexes, include immunodetection of complexes using antibodies reactive with the 57316 or 33338 protein or target molecule, as well as enzyme-linked assays which rely on detecting an enzymatic activity associated with the 57316 or 33338 protein or target molecule.

Alternatively, cell free assays can be conducted in a liquid phase. In such an assay, the reaction products are separated from non-reacted components, by any of a number of standard techniques, including, but not limited to: differential centrifugation (e.g., Rivas et al. (1993) *Trends Biochem. Sci.* 18:284–287); chromatography (e.g., gel filtration chromatography or ion-exchange chromatography); electrophoresis (e.g., Ausubel et al. eds. (1999) *Current Protocols in Molecular Biology*, J. Wiley, New York); and immunoprecipitation (e.g., Ausubel, supra). Such resins and chromatographic techniques are known to one skilled in the art (e.g., Heegaard, 1998, J. Mol. Recognit. 11:141–148; Hage et al. (1997) *J. Chromatogr. B Biomed. Sci. Appl.* 699:499–525). Further, fluorescence energy transfer can also be conveniently utilized, as described herein, to detect binding without further purification of the complex from solution.

In a preferred embodiment, the assay includes contacting the 57316 or 33338 protein or biologically active portion thereof with a known compound which binds 57316 or 33338 to form an assay mixture, contacting the assay mixture with a test compound, and determining the ability of the test compound to interact with a 57316 or 33338 protein, wherein determining the ability of the test compound to interact with a 57316 or 33338 protein includes determining the ability of the test compound to preferentially bind to 57316 or 33338 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 57316 or 33338 genes herein identified. In an alternative embodiment, the invention provides methods for determining the ability of the test compound to modulate the activity of a 57316 or 33338 protein through modulation of the activity of a downstream effector of a 57316 or 33338 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, non-reacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from non-reacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 57316 or 33338 proteins can be used as "bait proteins" in a two-hybrid assay or three-hybrid assay (e.g., U.S. Pat. No. 5,283,317; Zervos et al., (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; PCT publication number WO 94/10300), to identify other proteins, which bind to or interact with 57316 or 33338 ("57316 or 33338-binding proteins" or "57316 or 33338-bp") and are involved in 57316 or 33338 activity. Such 57316 or 33338-bps can be activators or inhibitors of signals by the 57316 or 33338 proteins or 57316 or 33338 targets as, for example, downstream elements of a 57316 or 33338-mediated signaling pathway.

The two-hybrid system is based on the modular nature of most transcription factors, which consist of separable DNA-binding and activation domains. Briefly, the assay utilizes two different DNA constructs. In one construct, the gene that codes for a 57316 or 33338 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively, the 57316 or 33338 protein can be fused to the activator domain). If the "bait" and the "prey" proteins are able to interact in vivo forming a 57316 or 33338-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the 57316 or 33338 protein.

In another embodiment, modulators of 57316 or 33338 expression are identified. For example, a cell or cell free mixture is contacted with a candidate compound and the expression of 57316 or 33338 mRNA or protein evaluated relative to the level of expression of 57316 or 33338 mRNA or protein in the absence of the candidate compound. When expression of 57316 or 33338 mRNA or protein is greater in the presence of the candidate compound than in its absence, the candidate compound is identified as a stimulator of 57316 or 33338 mRNA or protein expression. Alternatively, when expression of 57316 or 33338 mRNA or protein is less (i.e., statistically significantly less) in the presence of the candidate compound than in its absence, the candidate compound is identified as an inhibitor of 57316 or 33338 mRNA or protein expression. The level of 57316 or 33338 mRNA or protein expression can be determined by methods described herein for detecting 57316 or 33338 mRNA or protein.

In another aspect, the invention pertains to a combination of two or more of the assays described herein. For example, a modulating agent can be identified using a cell-based or a cell free assay, and the ability of the agent to modulate the activity of a 57316 or 33338 protein can be confirmed in vivo, e.g., in an animal such as an animal model for a disease.

This invention further pertains to novel agents identified by the above-described screening assays. Accordingly, it is within the scope of this invention to further use an agent identified as described herein (e.g., a 57316 or 33338 modulating agent, an antisense 57316 or 33338 nucleic acid molecule, a 57316 or 33338-specific antibody, or a 57316 or 33338-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome, e.g., to locate gene regions associated with genetic disease or to associate 57316 or 33338 with a disease; (ii) identify an individual from a minute biological sample (tissue typing); and (iii) aid in forensic identification of a biological sample. These applications are described in the subsections below.

Chromosome Mapping

The 57316 or 33338 nucleotide sequences or portions thereof can be used to map the location of the 57316 or 33338 genes on a chromosome. This process is called chromosome mapping. Chromosome mapping is useful in correlating the 57316 or 33338 sequences with genes associated with disease.

Briefly, 57316 or 33338 genes can be mapped to chromosomes by preparing PCR primers (preferably 15–25 base pairs in length) from the 57316 or 33338 nucleotide sequence (e.g., SEQ ID NO:1 or SEQ ID NO:3, and SEQ ID NO:6 or SEQ ID NO:8). These primers can then be used for PCR screening of somatic cell hybrids containing individual human chromosomes. Only those hybrids containing the human gene corresponding to the 57316 or 33338 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes (D'Eustachio et al. (1983) *Science* 220:919–924).

Other mapping strategies e.g., in situ hybridization as described (Fan et al., (1990) *Proc. Natl. Acad. Sci. USA* 87:6223–6227), pre-screening with labeled flow-sorted chromosomes, and pre-selection by hybridization to chromosome specific cDNA libraries can be used to map 57316 or 33338 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of FISH, (see Verma et al. (1988) *Human Chromosomes: A Manual of Basic Techniques*, Pergamon Press, New York).

Reagents for chromosome mapping can be used individually to mark a single chromosome or a single site on that chromosome, or panels of reagents can be used for marking multiple sites and/or multiple chromosomes. Reagents corresponding to non-coding regions of the genes are typically preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), as described (e.g., Egeland et al., 1987, Nature, 325:783–787).

Moreover, differences in the DNA sequences between individuals affected and unaffected with a disease associated with the 57316 or 33338 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 57316 or 33338 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 57316 or 33338 nucleotide sequence described herein can be used to prepare PCR primers homologous to the 5'- and 3'-ends of the sequence. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the non-coding regions. Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences of SEQ ID NO:1 and SEQ ID NO:6 can provide positive individual identification with a panel of perhaps 10 to 1,000 primers which each yield a non-coding amplified sequence of 100 bases. If predicted coding sequences are used, such as those in SEQ ID NO:3 and SEQ ID NO:8 a more appropriate number of primers for positive individual identification would be 500–2,000.

If a panel of reagents from 57316 or 33338 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 57316 or 33338 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual nucleotide sequence information can be used for identification as an accurate alternative to patterns formed by restriction enzyme generated fragments. Sequences targeted to non-coding regions of SEQ ID NO:1 and SEQ ID NO:6 (e.g., fragments having a length of at least 20 nucleotide residues, preferably at least 30 nucleotide residues) are particularly appropriate for this use.

The 57316 or 33338 nucleotide sequences described herein can further be used to provide polynucleotide reagents, e.g., labeled or label-able probes which can be used in, for example, an in situ hybridization technique, to identify a specific tissue, e.g., a tissue containing hematopoietic cells. This can be very useful in cases where a forensic pathologist is presented with a tissue of unknown origin. Panels of such 57316 or 33338 probes can be used to identify tissue by species and/or by organ type.

In a similar fashion, these reagents, e.g., 57316 or 33338 primers or probes can be used to screen tissue culture for contamination (i.e., to screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides a method of determining if a subject is at risk for a disorder related to a lesion in, or the malexpression of, a gene that encodes a 57316 or 33338 polypeptide.

Such disorders include, e.g., a disorder associated with the malexpression of a 57316 or 33338 polypeptide, e.g., an immune disorder or a neoplastic disorder.

The method includes one or more of the following:

detecting, in a tissue of the subject, the presence or absence of a mutation which affects the expression of the 57316 or 33338 gene, or detecting the presence or absence of a mutation in a region which controls the expression of the gene, e.g., a mutation in the 5'-control region;

detecting, in a tissue of the subject, the presence or absence of a mutation which alters the structure of the 57316 or 33338 gene;

detecting, in a tissue of the subject, the malexpression of the 57316 or 33338 gene at the mRNA level, e.g., detecting a non-wild-type level of a mRNA; and detecting, in a tissue of the subject, the malexpression of the gene at the protein level, e.g., detecting a non-wild-type level of a 57316 or 33338 polypeptide.

In preferred embodiments the method includes: ascertaining the existence of at least one of: a deletion of one or more nucleotides from the 57316 or 33338 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1 or SEQ ID NO:6, or naturally occurring mutants thereof, or 5'- or 3'-flanking sequences naturally associated with the 57316 or 33338 gene; (ii) exposing the probe/primer to nucleic acid of the tissue; and detecting the presence or absence of the genetic lesion by hybridization of the probe/primer to the nucleic acid, e.g., by in situ hybridization.

In preferred embodiments, detecting the malexpression includes ascertaining the existence of at least one of: an alteration in the level of a messenger RNA transcript of the 57316 or 33338 gene; the presence of a non-wild-type splicing pattern of a messenger RNA transcript of the gene; or a non-wild-type level of 57316 or 33338 RNA or protein.

Methods of the invention can be used for prenatal screening or to determine if a subject's offspring will be at risk for a disorder.

In preferred embodiments the method includes determining the structure of a 57316 or 33338 gene, an abnormal structure being indicative of risk for the disorder.

In preferred embodiments the method includes contacting a sample form the subject with an antibody to the 57316 or 33338 protein or a nucleic acid, which hybridizes specifically with the gene. These and other embodiments are discussed below.

Diagnostic and Prognostic Assays

The presence, level, or absence of 57316 or 33338 protein or nucleic acid in a biological sample can be evaluated by obtaining a biological sample from a test subject and contacting the biological sample with a compound or an agent capable of detecting 57316 or 33338 protein or nucleic acid (e.g., mRNA, genomic DNA) that encodes 57316 or 33338 protein such that the presence of 57316 or 33338 protein or nucleic acid is detected in the biological sample. The term "biological sample" includes tissues, cells and biological fluids isolated from a subject, as well as tissues, cells and fluids present within a subject. A preferred biological sample is serum. The level of expression of the 57316 or 33338 gene can be measured in a number of ways, including, but not limited to: measuring the mRNA encoded by the 57316 or 33338 genes; measuring the amount of protein encoded by the 57316 or 33338 genes; or measuring the activity of the protein encoded by the 57316 or 33338 genes.

The level of mRNA corresponding to the 57316 or 33338 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 57316 or 33338 nucleic acid, such as the nucleic acid of SEQ ID NO:1 or SEQ ID NO:6, the deposited nucleotide sequence, or a portion thereof, such as an oligonucleotide of at least 7, 15, 30, 50, 100, 250 or 500 nucleotides in length and sufficient to specifically hybridize under stringent conditions to 57316 or 33338 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 57316 or 33338 genes.

The level of mRNA in a sample that is encoded by 57316 or 33338 can be evaluated with nucleic acid amplification, e.g., by RT-PCR (U.S. Pat. No. 4,683,202), ligase chain reaction (Barany, (1991), Proc. Natl. Acad. Sci. USA 88:189–193), self-sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), rolling circle replication (U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5'- or 3'-regions of a 57316 or 33338 gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence between the primers.

For in situ methods, a cell or tissue sample can be prepared/processed and immobilized on a support, typically a glass slide, and then contacted with a probe that can hybridize to mRNA that encodes the 57316 or 33338 gene being analyzed.

In another embodiment, the methods include further contacting a control sample with a compound or agent capable of detecting 57316 or 33338 mRNA, or genomic DNA, and comparing the presence of 57316 or 33338 mRNA or genomic DNA in the control sample with the presence of 57316 or 33338 mRNA or genomic DNA in the test sample.

A variety of methods can be used to determine the level of protein encoded by 57316 or 33338. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 57316 or 33338 protein in a biological sample in vitro as well as in vivo. In vitro techniques for detection of 57316 or 33338 protein include enzyme linked immunosorbent assays (ELISAs), immunoprecipitation, immunofluorescence, enzyme immunoassay (EIA), radioimmunoassay (RIA), and Western blot analysis. In vivo techniques for detection of 57316 or 33338 protein include introducing into a subject a labeled anti-57316 or 33338 antibody. For example, the antibody can be labeled with a radioactive marker whose presence and location in a subject can be detected by standard imaging techniques.

In another embodiment, the methods further include contacting the control sample with a compound or agent capable of detecting 57316 or 33338 protein, and comparing the presence of 57316 or 33338 protein in the control sample with the presence of 57316 or 33338 protein in the test sample.

The invention also includes kits for detecting the presence of 57316 or 33338 in a biological sample. For example, the kit can include a compound or agent capable of detecting 57316 or 33338 protein or mRNA in a biological sample, and a standard. The compound or agent can be packaged in a suitable container. The kit can further comprise instructions for using the kit to detect 57316 or 33338 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably-labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with malexpressed, aberrant or unwanted 57316 or 33338 expression or activity. As used herein, the term "unwanted" includes an unwanted phenomenon involved in a biological response such as pain or deregulated cell proliferation.

In one embodiment, a disease or disorder associated with aberrant or unwanted 57316 or 33338 expression or activity is identified. A test sample is obtained from a subject and 57316 or 33338 protein or nucleic acid (e.g., mRNA or genomic DNA) is evaluated, wherein the level, e.g., the presence or absence, of 57316 or 33338 protein or nucleic acid is diagnostic for a subject having or at risk of developing a disease or disorder associated with aberrant or unwanted 57316 or 33338 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 57316 or 33338 expression or activity. For example, such methods can be used to determine whether a subject can be effectively treated with an agent that modulates 57316 or 33338 expression or activity.

The methods of the invention can also be used to detect genetic alterations in a 57316 or 33338 gene, thereby determining if a subject with the altered gene is at risk for a disorder characterized by misregulation in 57316 or 33338 protein activity or nucleic acid expression, such as a disorder associated with Alzheimer's disease, diffuse Lewy body disease, or motor neuron disease. In preferred embodiments, the methods include detecting, in a sample from the subject, the presence or absence of a genetic alteration characterized by at least one of an alteration affecting the integrity of a gene encoding a 57316 or 33338 protein, or the malexpression of the 57316 or 33338 gene. For example, such genetic alterations can be detected by ascertaining the existence of at least one of 1) a deletion of one or more nucleotides from a 57316 or 33338 gene; 2) an addition of one or more nucleotides to a 57316 or 33338 gene; 3) a substitution of one or more nucleotides of a 57316 or 33338 gene, 4) a chromosomal rearrangement of a 57316 or 33338 gene; 5) an alteration in the level of a messenger RNA transcript of a 57316 or 33338 gene, 6) aberrant modification of a 57316 or 33338 gene, such as of the methylation pattern of the genomic DNA, 7) the presence of a non-wild-type splicing pattern of a messenger RNA transcript of a 57316 or 33338 gene, 8) a non-wild-type level of a 57316 or 33338 protein, 9) allelic loss of a 57316 or 33338 gene, and 10) inappropriate post-translational modification of a 57316 or 33338 protein.

An alteration can be detected without a probe/primer in a polymerase chain reaction, such as anchor PCR or RACE-PCR, or, alternatively, in a ligation chain reaction (LCR), the latter of which can be particularly useful for detecting point mutations in the 57316 or 33338 gene. This method can include the steps of collecting a sample of cells from a subject, isolating nucleic acid (e.g., genomic, mRNA or both) from the sample, contacting the nucleic acid sample with one or more primers which specifically hybridize to a 57316 or 33338 gene under conditions such that hybridization and amplification of the 57316 or 33338 gene occurs (if present), and detecting the presence or absence of an amplification product, or detecting the size of the amplification product and comparing the length to a control sample. It is anticipated that PCR and/or LCR can be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al (1989) *Proc. Natl. Acad. Sci. USA* 86:1173–1177), Q-Beta Replicase (Lizardi et al. (1988) *Bio/Technology* 6:1197), or other nucleic acid amplification methods, followed by the detection of the amplified molecules using techniques known to those of skill in the art.

In another embodiment, mutations in a 57316 or 33338 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis, and compared. Differences in fragment length sizes between sample and control DNA indicates mutations in the sample DNA. Moreover, the use of sequence specific ribozymes (e.g., U.S. Pat. No. 5,498, 531) can be used to score for the presence of specific mutations by development or loss of a ribozyme cleavage site.

In other embodiments, genetic mutations in 57316 or 33338 can be identified by hybridizing a sample to control nucleic acids, e.g., DNA or RNA, by, e.g., two-dimensional arrays, or, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al. (1996) *Hum. Mutat.* 7:244–255; Kozal et al. (1996) *Nature Med.* 2:753–759). For example, genetic mutations in 57316 or 33338 can be identified in two-dimensional arrays containing light-generated DNA probes as described (Cronin et al.supra). Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 57316 or 33338 gene and detect mutations by comparing the sequence of the sample 57316 or 33338 with the corresponding wild-type (control) sequence. Automated sequencing procedures can be utilized when performing the diagnostic assays (1995, Biotechniques 19:448), including sequencing by mass spectrometry.

Other methods for detecting mutations in the 57316 or 33338 gene include methods in which protection from cleavage agents is used to detect mismatched bases in RNA/RNA or RNA/DNA heteroduplexes (Myers et al. (1985) *Science* 230:1242; Cotton et al., (1988) *Proc. Natl. Acad. Sci. USA* 85:4397; Saleeba et al, (1992) *Meth. Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 57316 or 33338 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 57316 or 33338 genes. For example, single strand conformation polymorphism (SSCP) can be used to detect differences in electrophoretic mobility between mutant and wild-type nucleic acids (Orita et al. (1989) *Proc. Natl. Acad. Sci. USA* 86:2766; Cotton (1993) *Mutat. Res.* 285:125–144; Hayashi (1992) *Genet. Anal. Tech. Appl.* 9:73–79). Single-stranded DNA fragments of sample and control 57316 or 33338 nucleic acids will be denatured and allowed to re-nature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 base pairs of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension (Saiki et al (1986) *Nature* 324:163; Saiki et al. (1989) *Proc. Natl. Acad. Sci. USA* 86:6230).

Alternatively, allele specific amplification technology that depends on selective PCR amplification can be used in conjunction with the instant invention. Oligonucleotides used as primers for specific amplification can carry the mutation of interest in the center of the molecule (so that amplification depends on differential hybridization; Gibbs et al. (1989) *Nucl. Acids Res.* 17:2437–2448) or at the extreme 3'-end of one primer where, under appropriate conditions, mismatch can prevent, or reduce polymerase extension (Prossner, 1993, Tibtech 11:238). In addition, it can be desirable to introduce a novel restriction site in the region of the mutation to create cleavage-based detection (Gasparini et al. (1992) *Mol. Cell Probes* 6:1). It is anticipated that in certain embodiments, amplification can also be performed using Taq ligase for amplification (Barany, 1991, Proc. Natl. Acad. Sci. USA 88:189). In such cases, ligation will occur only if there is a perfect match at the 3'-end of the 5'-sequence making it possible to detect the presence of a known mutation at a specific site by looking for the presence or absence of amplification.

The methods described herein can be performed, for example, using pre-packaged diagnostic kits comprising at least one probe nucleic acid or antibody reagent described herein, which can be conveniently used, e.g., in clinical settings to diagnose patients exhibiting symptoms or family history of a disease or illness involving a 57316 or 33338 gene.

Use of 57316 or 33338 Molecules as Surrogate Markers

The 57316 or 33338 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 57316 or 33338 molecules of the invention can be detected, and can be correlated with one or more biological states in vivo. For example, the 57316 or 33338 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers have been described (e.g., Koomen et al. (2000) *J. Mass. Spectrom.* 35:258–264; James (1994) *AIDS Treat. News Arch.* 209).

The 57316 or 33338 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 57316 or 33338 marker) transcription or expression, the amplified marker can be in a quantity which is more readily detectable than the drug itself. Also, the marker can be more easily detected due to the nature of the marker itself; for example, using the methods described herein, anti-57316 or 33338 antibodies can be employed in an immune-based detection system for a 57316 or 33338 protein marker, or 57316 or 33338-specific radiolabeled probes can be used to detect a 57316 or 33338 mRNA marker. Furthermore, the use of a pharmacodynamic marker can offer mechanism-based prediction of risk due to drug treatment beyond the range of possible direct observations. Examples of the use of pharmacodynamic markers have been described (e.g., U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; Nicolau (1999) *Am, J. Health-Syst. Pharm.* 56 Suppl. 3: S16–S20).

The 57316 or 33338 molecules of the invention are also useful as pharmacogenomic markers. As used herein, a "pharmacogenomic marker" is an objective biochemical marker which correlates with a specific clinical drug response or susceptibility in a subject (e.g., McLeod et al. (1999) *Eur. J. Cancer* 35: 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 57316 or 33338 protein or RNA) for specific tumor markers in a subject, a drug or course of treatment can be selected that is optimized for the treatment of the specific tumor likely to be present in the subject. Similarly, the presence or absence of a specific sequence mutation in 57316 or 33338 DNA can correlate 57316 or 33338 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-57316 or 33338 antibodies and small molecule modulators of 57316 or 33338 (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizer (BASF; Florham Park, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including an agent in the composition that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents and/or adjuvant materials can be included as part of the composition. The tablets, pills, capsules, troches and the like can contain any of the following ingredients, or compounds of a similar nature: a binder, such as microcrystalline cellulose, gum tragacanth or gelatin; an excipient, such as starch or lactose; a disintegrating agent, such as alginic acid, Primogel™, or corn starch; a lubricant, such as magnesium stearate or Sterotes™; a glidant, such as colloidal silicon dioxide; a sweetening agent, such as sucrose or saccharin; or a flavoring agent, such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells using monoclonal antibodies directed towards viral antigens) can also be used as pharmaceutically acceptable carriers. These can be prepared according to described methods (e.g., U.S. Pat. No. 4,522, 811).

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 milligrams per kilogram body weight, preferably about 0.01 to 25 milligrams per kilogram body weight, more preferably about 0.1 to 20 milligrams per kilogram body weight, and even more preferably about 1 to 10 milligrams per kilogram, 2 to 9 milligrams per kilogram, 3 to 8 milligrams per kilogram, 4 to 7 milligrams per kilogram, or 5 to 6 milligrams per kilogram body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 milligrams per kilogram of body weight (generally 10 to 20 milligrams per kilogram). If the antibody is to act in the brain, a dosage of 50 to 100 milligrams per kilogram is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for the lipidation of antibodies is described by Cruikshank et al. (1997) *J. AIDS Hum. Retrovir.* 14:193.

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including hetero-organic and organo-metallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, and the drug moiety is not to be construed as limited to classical chemical therapeutic agents. For example, the drug moiety can be a protein or polypeptide possessing a desired biological activity. Such proteins can include, for example, a toxin such as abrin, ricin A, gelonin, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukins-1, -2, and -6, granulocyte macrophage colony stimulating factor, granulocyte colony stimulating factor, or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 57316 or 33338 expression or activity. With regards to both prophylactic and therapeutic methods of treatment, such treatments can be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype".) Thus, another aspect of the invention provides methods for tailoring an individual's prophylactic or therapeutic treatment with either the 57316 or 33338 molecules of the present invention or 57316 or 33338 modulators according to that individual's drug response genotype.

Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

A therapeutic agent includes, but is not limited to, small molecules, peptides, antibodies, ribozymes and antisense oligonucleotides.

Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing a disease or condition in a subject associated with an aberrant or unwanted 57316 or 33338 expression or activity, by administering to the subject a 57316 or 33338 or an agent which modulates 57316 or 33338 expression, or at least one 57316 or 33338 activity. Subjects at risk for a disease which is caused or contributed to by aberrant or unwanted 57316 or 33338 expression or activity can be identified by, for example, any or a combination of diagnostic or prognostic assays as described herein. Administration of a prophylactic agent can occur prior to the manifestation of symptoms characteristic of the 57316 or 33338 aberrance, such that a disease or disorder is prevented or, alternatively, delayed in its progression. Depending on the type of 57316 or 33338 aberrance, for example, a 57316 or 33338 agonist or 57316 or 33338 antagonist agent can be used for treating the subject. The appropriate agent can be determined based on screening assays described herein.

It is possible that some 57316 or 33338 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 57316 or 33338 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 57316 or 33338 disorders. Such molecules can include, but are not limited to peptides, phosphopeptides, small organic or inorganic molecules, or antibodies (including, for example, polyclonal, monoclonal, human, humanized, anti-idiotypic, chimeric or single chain antibodies, and Fab, F(ab')$^2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 57316 or 33338 expression is through the use of aptamer molecules specific for 57316 or 33338 protein. Aptamers are nucleic acid molecules having a tertiary structure that permits them to specifically bind to protein ligands (e.g., Osborne et al., (1997) *Curr. Opin. Chem. Biol.* 1:5–9; Patel (1997) *Curr. Opin. Chem. Biol.* 1:32–46). Since nucleic acid molecules can in many cases be more conveniently introduced into target cells than therapeutic protein molecules can be, aptamers offer a method by which 57316 or 33338 protein activity can be specifically decreased without the introduction of drugs or other molecules which can have pluripotent effects.

Antibodies can be generated that are both specific for target gene product and that reduce target gene product activity. Such antibodies may, therefore, by administered in instances whereby negative modulatory techniques are appropriate for the treatment of 57316 or 33338 disorders.

In circumstances wherein injection of an animal or a human subject with a 57316 or 33338 protein or epitope for stimulating antibody production is harmful to the subject, it is possible to generate an immune response against 57316 or 33338 through the use of anti-idiotypic antibodies (e.g., Herlyn (1999) *Ann. Med.* 31:66–78; Bhattacharya-Chatterjee et al. (1998) *Cancer Treat. Res.* 94:51–68. If an anti-idiotypic antibody is introduced into a mammal or human subject, it should stimulate the production of anti-anti-idiotypic antibodies, which should be specific to the 57316 or 33338 protein. Vaccines directed to a disease characterized by 57316 or 33338 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (e.g., Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate 57316 or 33338 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 57316 or 33338 activity is used as a template, or "imprinting molecule," to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. Detailed reviews of this technique appear in the art (Ansell et al. (1996) *Curr. Opin. Biotechnol.* 7:89–94; Shea (1994) Trends Polymer Sci. 2:166–173). Such "imprinted" affinity matrixes are amenable to ligand-binding assays, whereby the immobilized monoclonal antibody component is replaced by an appropriately imprinted matrix (e.g., a matrix described in Vlatakis et al. (1993) *Nature* 361:645–647. Through the use of isotope-labeling, the "free" concentration of compound which modulates the expression or activity of 57316 or 33338 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiber optic devices, in turn allowing the dose in a test subject to be quickly optimized based on its individual $IC_{50}$. A rudimentary example of such a "biosensor" is discussed in Kriz et al. (1995) *Anal. Chem.* 67:2142–2144.

Another aspect of the invention pertains to methods of modulating 57316 or 33338 expression or activity for therapeutic purposes. Accordingly, in an exemplary embodiment, the modulatory method of the invention involves contacting a cell with a 57316 or 33338 or agent that modulates one or more of the activities of 57316 or 33338 protein activity associated with the cell. An agent that modulates 57316 or 33338 protein activity can be an agent as described herein, such as a nucleic acid or a protein, a naturally-occurring target molecule of a 57316 or 33338 protein (e.g., a 57316 or 33338 substrate or receptor), a 57316 or 33338 antibody, a 57316 or 33338 agonist or antagonist, a peptidomimetic of a 57316 or 33338 agonist or antagonist, or other small molecule.

In one embodiment, the agent stimulates one or 57316 or 33338 activities. Examples of such stimulatory agents include active 57316 or 33338 protein and a nucleic acid molecule encoding 57316 or 33338. In another embodiment, the agent inhibits one or more 57316 or 33338 activities. Examples of such inhibitory agents include antisense 57316 or 33338 nucleic acid molecules, anti-57316 or 33338 antibodies, and 57316 or 33338 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 57316 or 33338 protein or nucleic acid molecule. In one embodiment, the method involves administering an agent (e.g., an agent identified by a screening assay described herein), or combination of agents that modulates (e.g., up-regulates or down-regulates) 57316 or 33338 expression or activity. In another embodiment, the method involves administering a 57316 or 33338 protein or nucleic acid molecule as therapy to compensate for reduced, aberrant, or unwanted 57316 or 33338 expression or activity.

Stimulation of 57316 or 33338 activity is desirable in situations in which 57316 or 33338 is abnormally down-regulated and/or in which increased 57316 or 33338 activity is likely to have a beneficial effect. For example, stimulation of 57316 or 33338 activity is desirable in situations in which a 57316 or 33338 is down-regulated and/or in which increased 57316 or 33338 activity is likely to have a beneficial effect. Likewise, inhibition of 57316 or 33338 activity is desirable in situations in which 57316 or 33338 is abnormally up-regulated and/or in which decreased 57316 or 33338 activity is likely to have a beneficial effect. The 57316 or 33338 molecules can act as novel diagnostic targets and therapeutic agents for controlling one or more of cellular proliferative and/or differentiative disorders, hormonal disorders, immune and inflammatory disorders, or neurological disorders as described above as well as, cardiovascular disorders, blood vessel disorders, platelet disorders, viral diseases, hepatic disorders, and pain and metabolic disorders, or skeletal or bone metabolism disorders described below.

Cardiovascular disorders include, but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, disorders involving cardiac transplantation, and congestive heart failure.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi's sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Blood platelet disorders include, but are not limited to, thrombocytopenia due to a reduced number of megakaryocytes in the bone marrow, for example, as a result of chemotherapy; invasive disorders, such as leukemia, idiopathic or drug- or toxin-induced aplasia of the marrow, or rare hereditary amegakaryocytic thrombocytopenias; ineffective thrombopoiesis, for example, as a result of megaloblastic anemia, alcohol toxicity, vitamin B12 or folate deficiency, myelodysplastic disorders, or rare hereditary disorders (e.g., Wiskott-Aldrich syndrome and May-hegglin anomaly); a reduction in platelet distribution, for example, as a result of cirrhosis, a splenic invasive disease (e.g., Gaucher's disease), or myelofibrosis with extramedullary myeloid metaplasia; increased platelet destruction, for example, as a result of removal of IgG-coated platelets by the mononuclear phagocytic system (e.g., idiopathic thrombocytopenic purpura (ITP), secondary immune thrombocytopenia (e.g., systemic lupus erythematosus, lymphoma, or chronic lymphocytic leukemia), drug-related immune thrombocytopenias (e.g., as with quinidine, aspirin, and heparin), post-transfusion purpura, and neonatal thrombocytopenia as a result of maternal platelet autoantibodies or maternal platelet alloantibodies). Also included are thrombocytopenia secondary to intravascular clotting and thrombin induced damage to platelets as a result of, for example, obstetric complications, metastatic tumors, severe gram-negative bacteremia, thrombotic thrombocytopenic purpura, or severe illness. Also included is dilutional thrombocytopenia, for example, due to massive hemorrhage. Blood platelet disorders also include, but are not limited to, essential thrombocytosis and thrombocytosis associated with, for example, splenectomy, acute or chronic inflammatory diseases, hemolytic anemia, carcinoma, Hodgkin's disease, lymphoproliferative disorders, and malignant lymphomas.

Additionally, 57316 or 33338 molecules can play an important role in the etiology of certain viral diseases, including but not limited to Hepatitis B, Hepatitis C and Herpes Simplex Virus (HSV). Modulators of 57316 or 33338 activity can be used to control viral diseases. For example, the 57316 or 33338 molecules can play a role in mediating viral protease activities important for viral infection. The modulators can be used in the treatment and/or diagnosis of viral infected tissue or virus-associated tissue fibrosis, especially liver and liver fibrosis. Also, 57316 or 33338 modulators can be used in the treatment and/or diagnosis of virus-associated carcinoma, especially hepatocellular cancer.

Aberrant expression and/or activity of 57316 or 33338 molecules can mediate disorders associated with skeletal integrity or bone metabolism. "Skeletal integrity" refers to direct or indirect effects on the formation or maintenance of bones or joints and the tissues, such as ligaments, tendons or muscles which connect and control movement of those structures. "Bone metabolism" refers to direct or indirect effects in the formation or degeneration of bone structures, e.g., bone formation, bone resorption, etc., which may ultimately affect the structural integrity of bones or the concentrations in serum of calcium and phosphate. This term also includes activities mediated by 57316 or 33338 molecule effects in bone cells, e.g. osteoclasts and osteoblasts, that may in turn result in bone formation and degeneration. These cells are responsible for the synthesis and remodeling of the collagenous bone matrix, among other activities. Collagen is the main structural component of bone and bone-associated skeletal structures beside calcium phosphate, so collagen synthesis and processing arc integral to bone or skeletal structure. 57316 or 33338 molecules can be involved in one or more of the steps which result in the correct collagen matrix for bone. In another example, 57316 or 33338 molecules can support different activities of bone resorbing osteoclasts such as the stimulation of differentiation of monocytes and mononuclear phagocytes into osteoclasts. Accordingly, 57316 or 33338 molecules that modulate the production of bone cells can influence bone formation and degeneration, and thus can be used to treat skeletal or bone disorders. Examples of such disorders include, but are not limited to, osteogenesis imperfecta, osteoporosis, osteodystrophy, osteomalacia, rickets, osteitis fibrosa cystica, Ehlers-Danlos syndrome, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Hepatic disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 57316 or 33338 may play an important role in the regulation of metabolism or pain disorders. Diseases of metabolic imbalance include, but are not limited to, obesity, anorexia nervosa, bullemia, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L., (1987) *Pain*, New York:McGraw-Hill); pain associated with muscoloskeletal disorders, e.g., joint pain; tooth pain; headaches; pain associated with surgery; pain related to irritable bowel syndrome; and chest pain.

Pharmacogenomics

The 57316 or 33338 molecules of the present invention, as well as agents, or modulators which have a stimulatory or inhibitory effect on 57316 or 33338 activity (e.g., 57316 or 33338 gene expression) as identified by a screening assay described herein can be administered to individuals to treat (prophylactically or therapeutically) 57316 or 33338-associated disorders associated with aberrant or unwanted 57316 or 33338 activity (e.g., disorders associated with hematopoiesis and immune disorders). In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 57316 or 33338 molecule or 57316 or 33338 modulator as well as tailoring the dosage and/or therapeutic regimen of treatment with a 57316 or 33338 molecule or 57316 or 33338 modulator.

Pharmacogenomics deals with clinically significant hereditary variations in the response to drugs due to altered drug disposition and abnormal action in affected persons (e.g., Eichelbaum et al. (1996) *Clin. Exp. Pharmacol. Physiol.* 23:983–985; Linder et al., (1997) *Clin. Chem.* 43:254–266). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is hemolysis after ingestion of oxidant drugs (antimalarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP can be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach" can be utilized to identify genes that predict drug response. According to this method, if a gene that encodes a drug's target is known (e.g., a 57316 or 33338 protein of the present invention), all common variants of that gene can be fairly easily identified in the population and it can be determined if having one version of the gene versus another is associated with a particular drug response.

Alternatively, a method termed "gene expression profiling," can be utilized to identify genes that predict drug response. For example, the gene expression of an animal dosed with a drug (e.g., a 57316 or 33338 molecule or 57316 or 33338 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 57316 or 33338 molecule or 57316 or 33338 modulator, such as a modulator identified by one of the exemplary screening assays described herein.

The present invention further provides methods for identifying new agents, or combinations, that are based on identifying agents that modulate the activity of one or more of the gene products encoded by one or more of the 57316 or 33338 genes of the present invention, wherein these products can be associated with resistance of the cells to a therapeutic agent. Specifically, the activity of the proteins encoded by the 57316 or 33338 genes of the present invention can be used as a basis for identifying agents for overcoming agent resistance. By blocking the activity of one or more of the resistance proteins, target cells, e.g., hematopoietic cells, will become sensitive to treatment with an agent that the unmodified target cells were resistant to.

Monitoring the influence of agents (e.g., drugs) on the expression or activity of a 57316 or 33338 protein can be applied in clinical trials. For example, the effectiveness of an agent determined by a screening assay as described herein to increase 57316 or 33338 gene expression, protein levels, or up-regulate 57316 or 33338 activity, can be monitored in clinical trials of subjects exhibiting decreased 57316 or 33338 gene expression, protein levels, or down-regulated 57316 or 33338 activity. Alternatively, the effectiveness of an agent determined by a screening assay to decrease 57316 or 33338 gene expression, protein levels, or down-regulate 57316 or 33338 activity, can be monitored in clinical trials of subjects exhibiting increased 57316 or 33338 gene expression, protein levels, or up-regulated 57316 or 33338 activity. In such clinical trials, the expression or activity of a 57316 or 33338 gene, and preferably, other genes that have been implicated in, for example, a 57316 or 33338-associated disorder can be used as a "read out" or markers of the phenotype of a particular cell.

Other Embodiments

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses 57316 or 33338 or from a cell or subject in which a 57316 or 33338 mediated response has been elicited; contacting the array with a 57316 or 33338 nucleic acid (preferably purified), a 57316 or 33338 polypeptide (preferably purified), or an anti-57316 or 33338 antibody, and thereby evaluating the plurality of capture probes. Binding, e.g., in the case of a nucleic acid, hybridization with a capture probe at an address of the plurality, is detected, e.g., by a signal generated from a label attached to the 57316 or 33338 nucleic acid, polypeptide, or antibody.

The capture probes can be a set of nucleic acids from a selected sample, e.g., a sample of nucleic acids derived from a control or non-stimulated tissue or cell.

The method can include contacting the 57316 or 33338 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 57316 or 33338. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing 57316 or 33338, e.g., analyzing structure, function, or relatedness to other nucleic acid or amino acid sequences. The method includes: providing a 57316 or 33338 nucleic acid or amino acid sequence; comparing the 57316 or 33338 sequence with one or more preferably a plurality of sequences from a collection of sequences, e.g., a nucleic acid or protein sequence database; to thereby analyze 57316 or 33338.

The method can include evaluating the sequence identity between a 57316 or 33338 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of 57316 or 33338. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

The sequence of a 57316 or 33338 molecules is provided in a variety of mediums to facilitate use thereof. A sequence can be provided as a manufacture, other than an isolated nucleic acid or amino acid molecule, which contains a 57316 or 33338 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form.

A 57316 or 33338 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon 57316 or 33338 sequence information of the present invention.

As used herein, the term "electronic apparatus" is intended to include any suitable computing or processing apparatus of other device configured or adapted for storing data or information. Examples of electronic apparatus, suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 57316 or 33338 sequence information.

A variety of data storage structures are available to a skilled artisan for creating a computer readable medium having recorded thereon a 57316 or 33338 nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the 57316 or 33338 nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

The present invention therefore provides a medium for holding instructions for performing a method for determining whether a subject has a 57316 or 33338-associated disease or disorder or a pre-disposition to a 57316 or 33338-associated disease or disorder, wherein the method comprises the steps of determining 57316 or 33338 sequence information associated with the subject and based on the 57316 or 33338 sequence information, determining whether the subject has a 57316 or 33338-associated disease or disorder and/or recommending a particular treatment for the disease, disorder, or pre-disease condition.

The present invention further provides in an electronic system and/or in a network, a method for determining whether a subject has a 57316 or 33338 or ubiquitin carboxyl terminal hydrolase-associated disease or disorder or a pre-disposition to a disease associated with 57316 or 33338, wherein the method comprises the steps of determining 57316 or 33338 sequence information associated with the subject, and based on the 57316 or 33338 sequence information, determining whether the subject has a 57316 or 33338-associated disease or disorder or a pre-disposition to a 57316 or 33338-associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a 57316 or 33338-associated disease or disorder or a pre-disposition to a 57316 or 33338-associated disease or disorder, said method comprising the steps of receiving 57316 or 33338 sequence information from the subject and/or information related thereto, receiving phenotypic information associated with the subject, acquiring information from the network corresponding to 57316 or 33338 and/or corresponding to a 57316 or 33338-associated disease or disorder, and based on one or more of the phenotypic information, the 57316 or 33338 information (e.g., sequence information and/or information related thereto), and the acquired information, determining whether the subject has a 57316 or 33338-associated disease or disorder or a pre-disposition to a 57316 or 33338-associated disease or disorder. The method may further comprise the step of recommending a particular treatment for the disease, disorder, or pre-disease condition.

The present invention also provides a business method for determining whether a subject has a 57316 or 33338-associated disease or disorder or a pre-disposition to a 57316 or 33338-associated disease or disorder, said method comprising the steps of receiving information related to 57316 or 33338 (e.g., sequence information and/or information related thereto), receiving phenotypic information associated with the subject, acquiring information from the network related to 57316 or 33338 and/or related to a 57316 or 33338-associated disease or disorder, and based on one or more of the phenotypic information, the 57316 or 33338 information, and the acquired information, determining whether the subject has a 57316 or 33338-associated disease or disorder or a pre-disposition to a 57316 or 33338-associated disease or disorder. The method may further comprise the step of recommending a particular treatment for the disease, disorder, or pre-disease condition.

The invention also includes an array comprising a 57316 or 33338 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be 57316 or 33338. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of ubiquitin carboxyl terminal hydrolase-associated disorders as described herein.

The array is also useful for ascertaining the effect of the expression of a gene on the expression of other genes in the same cell or in different cells (e.g., acertaining the effect of 57316 or 33338 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 57316 or 33338) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 57316 or 33338 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 57316 or 33338 sequence, or record, in computer readable form; comparing a second sequence to the 57316 or 33338 sequence; thereby analyzing a sequence. Comparison can include comparing to sequences for sequence identity or determining if one sequence is included within the other, e.g., determining if the 57316 or 33338 sequence includes a sequence being compared. In a preferred embodiment the 57316 or 33338 or second sequence is stored on a first computer, e.g., at a first site and the comparison is performed, read, or recorded on a second computer, e.g., at a second site. E.g., the 57316 or 33338 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

The contents of all references, patents and published patent applications cited throughout this application are incorporated herein by reference.

Equivalents

Those skilled in the art will recognize, or be able to ascertain using no more than routine experimentation, many equivalents to the specific embodiments of the invention described herein.

What is claimed is:

1. An isolated nucleic acid molecule selected from the group consisting of:
   a. a nucleic acid molecule comprising the nucleotide sequence of SEQ ID NO:1, the nucleotide sequence of SEQ ID NO:3, the complement of SEQ ID NO:1 or the complement of SEQ ID NO:3; and
   b. a nucleic acid molecule comprising a nucleotide sequence which encodes a polypeptide comprising the amino acid sequence of SEQ ID NO:2.

2. The nucleic acid molecule of claim 1 further comprising vector nucleic acid sequences.

3. The nucleic acid molecule of claim 1 further comprising nucleic acid sequences encoding a heterologous polypeptide.

4. A host cell which contains the nucleic acid molecule of claim 1.

5. The host cell of claim 4 which is a mammalian host cell.

6. A host cell which expresses the nucleic acid molecule of claim 1.

7. The host cell of claim 6 which is a mammalian host cell.

8. A non-human mammalian host cell containing the nucleic acid molecule of claim 1.

9. An isolated nucleic acid molecule, consisting of a nucleic acid sequence selected from the group consisting of:

a) SEQ ID NO:1;
b) SEQ ID NO:3; and
c) a nucleic acid molecule which encodes a polypeptide having an amino acid sequence consisting of SEQ ID NO:2.

10. A method for producing a polypeptide comprising the amino acid sequence of SEQ ID NO:2 comprising culturing the host cell of claim 4 under conditions in which the nucleic acid molecule is expressed.

11. A method for detecting the presence of a nucleic acid molecule of claim 1 in a sample, comprising the steps of:
   contacting the sample with a nucleic acid probe or primer which selectively hybridizes to the nucleic acid molecule; and determining whether the nucleic acid probe or pruner binds to a nucleic acid molecule in the sample.

12. The method of claim 11, wherein the sample comprises mRNA molecules and is contacted with a nucleic acid probe.

13. A kit comprising a compound which selectively hybridizes to a nucleic acid molecule of claim 1 and instructions for use.

* * * * *